United States Patent
Yoshimura et al.

(10) Patent No.: US 11,687,001 B2
(45) Date of Patent: Jun. 27, 2023

(54) ACTINIC RAY-SENSITIVE OR RADIATION-SENSITIVE RESIN COMPOSITION, RESIST FILM, PATTERN FORMING METHOD, AND METHOD FOR MANUFACTURING ELECTRONIC DEVICE

(71) Applicant: FUJIFILM Corporation, Tokyo (JP)

(72) Inventors: Tsutomu Yoshimura, Shizuoka (JP); Yasunori Yonekuta, Shizuoka (JP); Naoya Hatakeyama, Shizuoka (JP); Kohei Higashi, Shizuoka (JP); Yoichi Nishida, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 403 days.

(21) Appl. No.: 16/807,496

(22) Filed: Mar. 3, 2020

(65) Prior Publication Data

US 2021/0055653 A1 Feb. 25, 2021

Related U.S. Application Data

(63) Continuation of application No. PCT/JP2018/033328, filed on Sep. 7, 2018.

(30) Foreign Application Priority Data

Sep. 13, 2017 (JP) .............................. JP2017-176147
Jan. 31, 2018 (JP) .............................. JP2018-015424

(51) Int. Cl.
| | | |
|---|---|---|
| *G03F 7/039* | (2006.01) | |
| *C08F 220/18* | (2006.01) | |
| *C08F 212/14* | (2006.01) | |
| *C08F 212/08* | (2006.01) | |
| *G03F 7/004* | (2006.01) | |
| *G03F 7/038* | (2006.01) | |
| *C07C 381/12* | (2006.01) | |

(52) U.S. Cl.
CPC ............ *G03F 7/039* (2013.01); *C07C 381/12* (2013.01); *C08F 212/08* (2013.01); *C08F 212/24* (2020.02); *C08F 212/30* (2020.02); *C08F 220/1804* (2020.02); *C08F 220/1809* (2020.02); *G03F 7/0045* (2013.01); *G03F 7/038* (2013.01)

(58) Field of Classification Search
CPC .... C08F 220/26; C08F 220/30; C08F 220/18; C08F 220/1804; C08F 220/1809; G03F 7/039
See application file for complete search history.

(56) References Cited

U.S. PATENT DOCUMENTS

| | | | | |
|---|---|---|---|---|
| 5,861,231 A | * | 1/1999 | Barclay ................. | G03F 7/0045 430/270.1 |
| 6,042,997 A | * | 3/2000 | Barclay ................. | C08F 212/24 430/326 |
| 6,235,446 B1 | * | 5/2001 | Ikemura ................ | G03F 7/0045 430/905 |
| 6,340,553 B1 | | 1/2002 | Oomori et al. | |
| 2002/0031722 A1 | | 3/2002 | Oomori et al. | |
| 2004/0242798 A1 | | 12/2004 | Sounik et al. | |
| 2005/0032373 A1 | | 2/2005 | Cameron et al. | |
| 2008/0114139 A1 | | 5/2008 | Yamagishi et al. | |
| 2009/0023102 A1 | | 1/2009 | Shimbori et al. | |
| 2010/0216071 A1 | | 8/2010 | Goldfarb et al. | |
| 2011/0081612 A1 | | 4/2011 | Fujii et al. | |
| 2015/0268553 A1 | | 9/2015 | Katayama et al. | |
| 2015/0268557 A1 | | 9/2015 | Irie et al. | |
| 2017/0115569 A1 | | 4/2017 | Goto et al. | |
| 2018/0217497 A1 | | 8/2018 | Yoshino et al. | |
| 2018/0246406 A1 | | 8/2018 | Yoshino | |
| 2020/0142306 A1 | | 5/2020 | Higashi et al. | |

FOREIGN PATENT DOCUMENTS

| | | | | |
|---|---|---|---|---|
| CN | 102156384 A | | 8/2011 | |
| CN | 110914757 A | | 3/2020 | |
| EP | 1479700 A1 | * | 11/2004 | ............ C08F 212/08 |
| EP | 1517182 A1 | * | 3/2005 | ........... G03F 7/0397 |
| EP | 1959300 A1 | * | 8/2008 | ........... G03F 7/0392 |
| JP | 2000-347405 A | | 12/2000 | |
| JP | 2005099856 A | * | 4/2005 | ........... G03F 7/0046 |

(Continued)

OTHER PUBLICATIONS

Machine translation of WO 2017/078031 (no date).*
Machine translation of JP 2005-099856 (no date).*
Communication dated Dec. 20, 2021 issued by the Taiwan Intellectual Property Office in counterpart Taiwan Application No. 107132037.

(Continued)

*Primary Examiner* — Amanda C. Walke
(74) *Attorney, Agent, or Firm* — Sughrue Mion, PLLC

(57) ABSTRACT

Provided are an actinic ray-sensitive or radiation-sensitive resin composition containing a resin (A), in which the resin (A) includes a repeating unit having an acidic group and a repeating unit having an acid-decomposable group, a content of the repeating unit having an acidic group is 15% by mole or more with respect to all the repeating units in the resin (A), a content of the repeating unit having an acid-decomposable group is more than 20% by mole with respect to all the repeating units in the resin (A), a glass transition temperature of the resin (A) is 145° C. or lower, and the actinic ray-sensitive or radiation-sensitive resin composition is used for formation of a film having a film thickness of 2 μm or more; and a resist film, a pattern forming method, and a method for manufacturing an electronic device, each using the actinic ray-sensitive or radiation-sensitive resin composition.

24 Claims, No Drawings

(56) References Cited

FOREIGN PATENT DOCUMENTS

| | | | |
|---|---|---|---|
| JP | 2005257884 A | * | 9/2005 |
| JP | 2007-206425 A | | 8/2007 |
| JP | 2008-191218 A | | 8/2008 |
| JP | 2009-265609 A | | 11/2009 |
| JP | 2012-518692 A | | 8/2012 |
| JP | 2013-210619 A | | 10/2013 |
| JP | 2014-106306 A | | 6/2014 |
| JP | 2015-184389 A | | 10/2015 |
| JP | 2015-194715 A | | 11/2015 |
| KR | 10-2017-0012553 A | | 2/2017 |
| WO | 2005/105869 A1 | | 11/2005 |
| WO | 2017057226 A1 | | 4/2017 |
| WO | 2017078031 A1 | | 5/2017 |
| WO | 2018163602 A1 | | 9/2018 |
| WO | 2018168258 A1 | | 9/2018 |

OTHER PUBLICATIONS

Office Action dated Oct. 5, 2021, issued by the Korean Patent and Trademark Office in counterpart KR Patent Application No. 10-2020-7006382.

Communication dated Oct. 20, 2020, from the Japanese Patent Office in counterpart application No. 2019-542036.

International Search Report (PCT/ISA/210), issued by International Searching Authority in corresponding International Application No. PCT/JP2018/033328, dated Nov. 13, 2018.

Written Opinion (PCT/ISA/237) issued by the International Searching Authority in corresponding International Application No. PCT/JP2018/033328, dated Nov. 13, 2018.

Communication dated Mar. 28, 2022 by the Taiwanese Patent Office in counterpart Taiwanese Patent Application No. 107132037.

Office Action dated Jul. 18, 2022, issued by the Korean Intellectual Property Office in Korean Patent Application No. 10-2022-7019677.

Notice of Reasons for Revocation dated May 16, 2022 by the Japan Patent Office in counterpart Japanese Patent Application No. P2019-542036.

Brandrup et al., "Polymer Handbook" Fourth Edition, John Wiley & Sons, Inc., 1999, pp. 198 and 200, Total 4 pages.

Hitachi Chemical Co., Ltd., EnplaNet.com Fine Chemical: "Functional acrylate/methacrylate FANCRYL," <Monofunctional methacrylate> [on line], Jan. 23, 2003 printing, Mar. 3, 2022 search, Refer to Internet "dicyclopentanil methacrylate" <URL: https://www.enplanet.com/Company/00000143/Ja/Data/p001-lf.html>, Total 5 pages.

Komiya et al, "The photopolymerization reaction of N-28 acrylic-acid t-butyl," Heisei 24, Nihon University, Department of Science and Engineering, Academic Lecture Meeting Collected Papers, 2013, pp. 1213-1214, Total 2 pages.

Notification of Reasons for Revocation dated Oct. 24, 2022 by the Japan Patent Office in Machine English counterpart Japanese Patent Application No. 2019-542036.

Office Action dated Dec. 27, 2022, issued by the China National Intellectual Property Administration English in counterpart Chinese Patent Application No. 201880059342.7.

Office Action dated Mar. 29, 2023, issued by the Korean Intellectual Property Office in Korean Patent Application No. 10-2023-7008647.

Notice of Dispatch of Written Opinion dated Apr. 21, 2023 in the corresponding Japanese Patent Application 2019-542036, on JP Patent Opposition No. 2022-700195 in the Japanese Patent Office, with accompanying Written Opinion; 15 pages.

* cited by examiner

ACTINIC RAY-SENSITIVE OR RADIATION-SENSITIVE RESIN COMPOSITION, RESIST FILM, PATTERN FORMING METHOD, AND METHOD FOR MANUFACTURING ELECTRONIC DEVICE

CROSS REFERENCE TO RELATED APPLICATION

This is a continuation of International Application No. PCT/JP2018/033328 filed on Sep. 7, 2018, and claims priorities from Japanese Patent Application No. 2017-176147 filed on Sep. 13, 2017 and from Japanese Patent Application No. 2018-015424 filed on Jan. 31, 2018, the entire contents of which are incorporated herein by reference.

BACKGROUND OF THE INVENTION

1. Field of the Invention

The present invention relates to an actinic ray-sensitive or radiation-sensitive resin composition, a resist film, a pattern forming method, and a method for manufacturing an electronic device.

2. Description of the Related Art

An image forming method called chemical amplification has been used as an image forming method for a resist in order to compensate for a reduction in sensitivity caused by light absorption since a resist for a KrF excimer laser (248 nm). For example, examples of a chemically amplified positive-tone image forming method include an image forming method in which a photoacid generator in an exposed area decomposes upon exposure with an excimer laser, electron beams, extreme ultraviolet light, or the like to produce an acid, an alkali-insoluble group is converted to an alkali-soluble group using an acid thus generated as a reaction catalyst by post-exposure baking (PEB), and the exposed area is removed with an alkali developer.

On the other hand, miniaturization using a wavelength of an exposure light source has recently faced limits, and in particular, in process applications in an ion implantation process and a NAND memory (NOT AND memory), it has become a mainstream to make memory layers in a three-dimensional form for the purpose of achieving a large capacity. Since it is necessary to increase the number of processing stages in a vertical direction in making memory layers in a three-dimensional form, it has been required to increase the thickness of a resist film from a nano dimension to a micron dimension in the related art.

For example, JP2008-191218A describes a chemically amplified positive-tone photoresist composition for a thick film, which is used to form a thick-film photoresist layer having a film thickness of 5 to 150 μm.

Furthermore, JP2009-265609A also describes that a resist film having an average film thickness of 2.0 μm is formed with a resist composition including a resin having a specific structure.

In addition, JP2000-347405A describes a resist composition including a resin formed of 67% by mole of a hydroxystyrene unit, 22% by mole of a styrene unit, and 11% by mole of a 1-ethylcyclohexyl methacrylate unit, and also describes that a resist layer having a film thickness of 0.45 μm is formed with the resist composition.

SUMMARY OF THE INVENTION

While the present inventors have examined a composition for forming an actinic ray-sensitive or radiation-sensitive thick film (having a film thickness of 2 μm or more), they could see that it is difficult for the cross-sectional shape of a pattern of a thick film formed by lithography from a chemically amplified positive-tone photoresist composition for a thick film, described in JP2008-191218A to be rectangular, that is, the rectangularity is deteriorated. Therefore, the present inventors have also examined a resist composition including the resin described in JP2009-265609A or the resin described in JP2000-347405A, instead of the resin described in JP2008-191218A, and thus, they could see that the rectangularity is improved but a reduction in resolution or occurrence of film peeling after a vacuum treatment becomes manifest.

Therefore, an object of the present invention is to provide an actinic ray-sensitive or radiation-sensitive resin composition, which is used for formation of a film having a film thickness of 2 μm or more, and has excellent cross-sectional rectangularity of a pattern, suppressed film peeling after a vacuum treatment, and excellent resolution; a resist film formed with the actinic ray-sensitive or radiation-sensitive resin composition; and a pattern forming method and a method for manufacturing an electronic device, each using the actinic ray-sensitive or radiation-sensitive resin composition.

According to the examinations conducted by the present inventors, it is presumed that it is the content of repeating units having an acidic group reaching a certain value or higher that improves the cross-sectional rectangularity of a pattern by using the resin of JP2009-265609A or JP2000-347405A instead of the resin of JP2008-191218A. Furthermore, the present inventors have found that the resolution is reduced or the film peeling after a vacuum treatment occurs by using the resin of JP2009-265609A or JP2000-347405A, whereas it is possible to improve the resolution and suppress the film peeling after a vacuum treatment while maintaining the cross-sectional rectangularity of a pattern, by further increasing the content of the repeating unit having an acid-decomposable group in the resin and setting the glass transition temperature (Tg) of the resin to a certain value or less. It is presumed by the present inventors that the dissolution contrast was improved and the resolution was also improved by further increasing the content of the repeating unit having an acid-decomposable group in the resin. In addition, the fluidity of a film formed with the actinic ray-sensitive or radiation-sensitive resin composition was increased and the volatility of the solvent was improved by setting the Tg of the resin to a certain value or less, and as a result, the amount of the residual solvent in the film that causes the film peeling was decreased and the film peeling after a vacuum treatment was suppressed.

That is, the present inventors have found that the objects can be accomplished by the following configurations.

[1] An actinic ray-sensitive or radiation-sensitive resin composition comprising a resin (A), in which the resin (A) includes a repeating unit having an acidic group and a repeating unit having an acid-decomposable group, a content of the repeating unit having an acidic group is 15% by mole or more with respect to all the repeating units in the resin (A), a content of the repeating unit having an acid-decomposable group is more than 20% by mole with respect to all the repeating units in the resin (A), a glass transition temperature of the resin (A) is 145° C. or lower, and the actinic ray-sensitive or radiation-sensitive resin composition is used for formation of a film having a film thickness of 2 μm or more.

[2] The actinic ray-sensitive or radiation-sensitive resin composition as described in [1], in which the acidic group is a carboxyl group, a phenolic hydroxyl group, or a sulfo group.

[3] The actinic ray-sensitive or radiation-sensitive resin composition as described in [1] or [2], in which at least one of the repeating units contained in the resin (A) has an aromatic ring.

[4] The actinic ray-sensitive or radiation-sensitive resin composition as described in any one of [1] to [3], in which a content of the repeating unit having an acidic group is 45% by mole or more with respect to all the repeating units in the resin (A).

[5] The actinic ray-sensitive or radiation-sensitive resin composition as described in any one of [1] to [4], in which a Hansen solubility parameter of the resin (A) is 20.5 $(J/cm^3)^{0.5}$ or less.

[6] The actinic ray-sensitive or radiation-sensitive resin composition as described in any one of [1] to [5], in which the resin (A) has a repeating unit B1 derived from a monomer allowing a homopolymer formed therefrom to have a glass transition temperature of 50° C. or lower.

[7] The actinic ray-sensitive or radiation-sensitive resin composition as described in any one of [1] to [5], in which the resin (A) has a repeating unit C1 having a Hansen solubility parameter of 19.5 $(J/cm^3)^{0.5}$ or less.

[8] The actinic ray-sensitive or radiation-sensitive resin composition as described in any one of [1] to [5], in which the resin (A) has a repeating unit BC1 having a Hansen solubility parameter of 19.5 $(J/cm^3)^{0.5}$ or less and derived from a monomer allowing a homopolymer formed therefrom to have a glass transition temperature of 50° C. or lower.

[9] The actinic ray-sensitive or radiation-sensitive resin composition as described in any one of [6] to [8], in which the repeating unit B1, C1, or BC1 is a repeating unit derived from a monomer allowing a homopolymer formed therefrom to have a glass transition temperature of −20° C. or lower.

[10] The actinic ray-sensitive or radiation-sensitive resin composition as described in any one of [6] to [9], in which the repeating unit B1, C1, or BC1 is a repeating unit derived from a monomer having a Hansen solubility parameter of 16.0 $(J/cm^3)^{0.5}$ or less.

[11] The actinic ray-sensitive or radiation-sensitive resin composition as described in any one of [6] to [10], in which the repeating unit B1, C1, or BC1 is a repeating unit represented by General Formula (1-2).

(1-2)

In General Formula (1-2), $R_1$ represents a hydrogen atom, a halogen atom, or an alkyl group. $R_2$ represents a non-acid-decomposable chained alkyl group having 4 or more carbon atoms, which may include a heteroatom.

[12] The actinic ray-sensitive or radiation-sensitive resin composition as described in any one of [6] to [11], in which a content of the repeating unit B1, C1, or BC1 is 5% by mole or more with respect to all the repeating units in the resin (A).

[13] The actinic ray-sensitive or radiation-sensitive resin composition as described in any one of [1] to [12], in which the resin (A) contains a repeating unit represented by General Formula (1-2), a repeating unit represented by General Formula (1-3), and a repeating unit represented by General Formula (1-4).

(1-2)

(1-3)

(1-4)

In General Formula (1-2), $R_1$ represents a hydrogen atom, a halogen atom, or an alkyl group. $R_2$ represents a non-acid-decomposable chained alkyl group having 4 or more carbon atoms, which may include a heteroatom.

In General Formula (1-4), Ru represents a hydrogen atom, a halogen atom, or an alkyl group.

[14] The actinic ray-sensitive or radiation-sensitive resin composition as described in any one of [1] to [13], further comprising a compound that generates an acid upon irradiation with actinic rays or radiation, represented by General Formula (ZI-3).

(ZI-3)

In General Formula (ZI-3), M represents an alkyl group, a cycloalkyl group, or an aryl group, and in a case where M has a ring structure, the ring structure may include at least one of an oxygen atom, a sulfur atom, an ester bond, an amide bond, or a carbon-carbon double bond. $R_{1c}$ and $R_{2c}$ each independently represent a hydrogen atom, an alkyl group, a cycloalkyl group, a halogen atom, a cyano group, or an aryl group. $R_{1c}$ and $R_{2c}$ may be bonded to each other to form a ring. $R_x$ and $R_y$ each independently represent an alkyl group, a cycloalkyl group, or an alkenyl group. $R_x$ and $R_y$ may be bonded to each other to form a ring. Further, at least two selected from M, $R_{1c}$, or $R_{2c}$ may be bonded to each other to form a ring structure, and the ring structure may include a carbon-carbon double bond. $Z^-$ represents an anion.

[15] A pattern forming method comprising:
a resist film forming step of forming a resist film with the actinic ray-sensitive or radiation-sensitive resin composition as described in any one of [1] to [14];
an exposing step of exposing the resist film; and
a developing step of developing the exposed resist film with a developer.

[16] A method for manufacturing an electronic device, the method comprising the pattern forming method as described in [15].

[17] A resist film having a film thickness of 2 μm or more, the resist film formed with the actinic ray-sensitive or radiation-sensitive resin composition as described in any one of [1] to [14].

According to the present invention, it is possible to provide an actinic ray-sensitive or radiation-sensitive resin composition, which is used for formation of a film having a film thickness of 2 μm or more, and has excellent cross-sectional rectangularity of a pattern, suppressed film peeling after a vacuum treatment, and excellent resolution; a resist film formed with the actinic ray-sensitive or radiation-sensitive resin composition; and a pattern forming method and a method for manufacturing an electronic device, each using the actinic ray-sensitive or radiation-sensitive resin composition.

DESCRIPTION OF THE PREFERRED EMBODIMENTS

Hereinafter, the present invention will be described in detail.

Description of configuration requirements described below may be made on the basis of representative embodiments of the present invention in some cases, but the present invention is not limited to such embodiments.

"Actinic rays" or "radiation" in the present specification means, for example, a bright line spectrum of a mercury lamp, far ultraviolet rays typified by an excimer laser, extreme ultraviolet rays (EUV), X-rays, soft X-rays, electron beams (EB), or the like. "Light" in the present specification means actinic rays or radiation. "Exposure" in the present specification encompasses, unless otherwise specified, not only exposure by a bright line spectrum of a mercury lamp, far ultraviolet rays typified by an excimer laser, extreme ultraviolet rays, X-rays, EUV, or the like but also writing by particle rays such as electron beams and ion beams.

In the present specification, a numerical range expressed using "to" is used in a meaning of a range that includes the preceding and succeeding numerical values of "to" as the lower limit value and the upper limit value, respectively.

In the present specification, (meth)acrylate represents at least one of acrylate or methacrylate. In addition, (meth)acrylic acid represents at least one of acrylic acid or methacrylic acid.

In the present specification, the weight-average molecular weight (Mw), the number-average molecular weight (Mn), and the dispersity (also referred to as a molecular weight distribution (Mw/Mn) of a resin are defined as values in terms of polystyrene by means of gel permeation chromatography (GPC) measurement (solvent: tetrahydrofuran, flow amount (amount of a sample injected): 10 μL, columns: TSK gel Multipore HXL-M manufactured by Tosoh Corporation, column temperature: 40° C., flow rate: 1.0 mL/min, and detector: differential refractive index detector) using a GPC apparatus (HLC-8120GPC manufactured by Tosoh Corporation).

In citations for a group (atomic group) in the present specification, in a case where the group is denoted without specifying whether it is substituted or unsubstituted, the group includes both a group not having a substituent and a group having a substituent. For example, an "alkyl group" includes not only an alkyl group not having a substituent (unsubstituted alkyl group), but also an alkyl group having a substituent (substituted alkyl group). In addition, an "organic group" in the present specification refers to a group including at least one carbon atom.

Moreover, in a case of an expression, "which may have a substituent" in the present specification, the types of substituents, the positions of the substituents, and the number of the substituents are not particularly limited. The number of the substituents may be, for example, one, two, three, or more. Examples of the substituent include a monovalent non-metal atomic group excluding a hydrogen atom, and the substituent can be selected from, for example, the following substituent T.

(Substituent T)

Examples of the substituent T include halogen atoms such as a fluorine atom, a chlorine atom, a bromine atom, and an iodine atom; alkoxy groups such as a methoxy group, an ethoxy group, and a tert-butoxy group; aryloxy groups such as a phenoxy group and a p-tolyloxy group; alkoxycarbonyl groups such as a methoxycarbonyl group, a butoxycarbonyl group, and a phenoxycarbonyl group; acyloxy groups such as an acetoxy group, a propionyloxy group, and a benzoyloxy group; acyl groups such as an acetyl group, a benzoyl group, an isobutyryl group, an acryloyl group, a methacryloyl group, and a methoxalyl group; alkylsulfanyl groups such as a methylsulfanyl group and a tert-butylsulfanyl group; arylsulfanyl groups such as a phenylsulfanyl group and a p-tolylsulfanyl group; an alkyl group; a cycloalkyl group; an aryl group; a heteroaryl group; a hydroxyl group; a carboxyl group; a formyl group; a sulfo group; a cyano group; an al cylaminocarbonyl group; an arylaminocarbonyl group; a sulfonamido group; a silyl group; an amino group; a monoalkylamino group; a dialkylamino group; an arylamino group; and a combination thereof.

[Actinic Ray-Sensitive or Radiation-Sensitive Resin Composition]

The actinic ray-sensitive or radiation-sensitive resin composition of an embodiment of the present invention (hereinafter also simply referred to as "the composition of an embodiment of the present invention") is an actinic ray-sensitive or radiation-sensitive resin composition comprising a resin (A), in which the resin (A) includes a repeating unit having an acidic group and a repeating unit having an acid-decomposable group, a content of the repeating unit having an acidic group is 15% by mole or more with respect to all the repeating units in the resin (A), a content of the repeating unit having an acid-decomposable group is more than 20% by mole with respect to all the repeating units in the resin (A), a glass transition temperature of the resin (A) is 145° C. or lower, and the actinic ray-sensitive or radiation-sensitive resin composition is used for formation of a film having a film thickness of 2 μm or more.

The composition of the embodiment of the present invention is a so-called resist composition, and may be either a positive-tone resist composition or a negative-tone resist composition. In addition, the composition may be either a resist composition for alkali development or a resist composition for organic solvent development. Among those, the composition is preferably the positive-tone resist composition and the resist composition for alkali development.

The composition of the embodiment of the present invention is typically a chemically amplified resist composition.

Hereinafter, the components included in the composition of the embodiment of the present invention will be described in detail.

<Resin (A)>

The resin (A) included in the composition of the embodiment of the present invention is a resin including a repeating unit having an acidic group and a repeating unit having an acid-decomposable group, in which a content of the repeating unit having an acidic group is 15% by mole or more with respect to all the repeating units, a content of the repeating unit having an acid-decomposable group is more than 20% by mole with respect to all the repeating units, and a glass transition temperature is 145° C. or lower.

From the viewpoint that the resin (A) contains the repeating unit having an acid-decomposable group, it is a resin whose polarity increases by the action of an acid through decomposition. That is, in the pattern forming method of an embodiment of the present invention which will be described later, typically in a case where an alkali developer is employed as a developer, a positive-tone pattern is suitably formed, and in a case where an organic developer is employed as the developer, a negative-tone pattern is suitably formed.

[Glass Transition Temperature (Tg) of Resin (A)]

The Tg of the resin (A) is 145° C. or lower, preferably 60° C. to 145° C., more preferably 80° C. to 145° C., and still more preferably 95° C. to 135° C.

A method for measuring the Tg of the resin (A) is shown below.

(Method for Measuring Glass Transition Temperature of Resin (A)])

The glass transition temperature (Tg (A)) of the resin (A) was calculated as follows.

In a case where the repeating units constituting the resin (A) are defined as (a), (b), (c), . . . , the glass transition temperature (Tg (a), Tg (b), Tg (c), . . . ) of a homopolymer formed of only each of the repeating units (a polymer formed of only the repeating unit (a), a polymer formed of only the repeating unit (b), a polymer formed of only the repeating unit (c), . . . ) is calculated by the following method for measuring a glass transition temperature of a homopolymer. In a case where the weight percentages of the repeating units (a), (b), (c), . . . constituting the resin (A) are defined as wt % (a), wt % (b), wt % (c), . . . , respectively, the glass transition temperature (Tg (A)) of the resin (A) was calculated by the following equation.

$$Tg(A)=[\{Tg(a)\times wt\ \%(a)+Tg(b)\times wt\ \%(b)+Tg(c)\times wt\ \%(c)+\ldots\}/100]\times 0.7292+54.131$$

(Method for Measuring Glass Transition Temperature of Homopolymer)

As the glass transition temperature of the homopolymer, in a case where there is a catalog value or a literature value thereof, the value is employed, and in a case where there is not such a value, the glass transition temperature can be measured by differential scanning calorimetry (DSC). The weight-average molecular weight (Mw) and the dispersity (Mw/Mn) of the homopolymer provided for measurement of Tg are set to 18,000 and 1.7, respectively. As the DSC apparatus, a thermal analysis DSC differential scanning calorimeter Q1000 Type manufactured by TA Instruments Japan Ltd. is used and a temperature raising rate is set to 10° C./min to perform the measurement.

Furthermore, the homopolymer provided for measurement for Tg may be synthesized with corresponding monomers by a known method, and can be synthesized by, for example, a general dropwise addition polymerization method. An example of the measurement method is shown below.

54 parts by mass of propylene glycol monomethyl ether acetate (PGMEA) was heated at 80° C. under a nitrogen gas stream. While stirring the liquid, 125 parts by mass of a PGMEA solution including 21% by mass of a corresponding monomer and 0.35% by mass of 2,2'-dimethyl azobisisobutyrate was added dropwise thereto for 6 hours. After dropwise addition, the mixture was further stirred at 80° C. for 2 hours. The reaction solution was left to be cooled, then reprecipitated with a large amount of methanol/water (mass ratio of 9:1), and filtered, and the obtained solid was dried to obtain a homopolymer (Mw: 18,000, Mw/Mn: 1.7). The obtained homopolymer was provided for DSC measurement. The DSC apparatus and the temperature raising rate were as described above.

From the viewpoint that the Tg of the resin (A) can be effectively lowered while not deteriorating the other performance, it is preferable that the resin (A) has a repeating unit (also referred to as a "repeating unit B1") derived from a monomer (also referred to as a "monomer B1") allowing a homopolymer formed therefrom to have a glass transition temperature (the glass transition temperature of the homopolymer) of 50° C. or lower.

Furthermore the glass transition temperature of a homopolymer as formed from the monomer is determined by the method, and that is, the Tg of a homopolymer obtained from the monomer B1, which has a weight-average molecular weight (Mw) of 18,000 and a dispersity (Mw/Mn) of 1.7, is 50° C. or lower.

It is preferable that the repeating unit B1 has no acid-decomposable group.

It is more preferable that the repealing unit B1 is a repeating unit derived from a monomer allowing a homopolymer formed therefrom to have a glass transition temperature (the glass transition temperature of the homopolymer) of −20° C. or lower.

Moreover, from the viewpoint that the residual solvent can be more easily volatilized, it is preferable that the repeating unit B1 is a repeating unit having a non-acid-decomposable chained alkyl group having 4 or more carbon atoms, which may include a heteroatom. In the present specification, an expression, "being non-acid-decomposable", means that an acid generated by a photoacid generator has a property of not causing a leaving/decomposing reaction.

That is, more specific examples of the "non-acid-decomposable chained alkyl group" include a chained alkyl group that does not leave from the resin (A) by the action of an acid generated by a photoacid generator and a chained alkyl group that does not decompose by the action of an acid generated by a photoacid generator.

Hereinafter, the repeating unit having a non-acid-decomposable chained alkyl group having 4 or more carbon atoms, which may include a heteroatom, will be described.

The non-acid-decomposable chained alkyl group having 4 or more carbon atoms, which may include a heteroatom, is not particularly limited, and examples thereof include a chained (linear or branched) alkyl group having 4 to 20 carbon atoms and a chained alkyl group having 4 to 20 carbon atoms, which contains a heteroatom.

Examples of the chained alkyl group having 4 to 20 carbon atoms, which contains a heteroatom, include a chained alkyl group, in which one or two or more of —$CH_2$-'s are substituted with —O—, —S—, —CO—, —$NR_6$—, or a divalent organic group formed by combination of two or more of these groups. $R_6$ represents a hydrogen atom or an alkyl group having 1 to 6 carbon atoms.

Specific examples of the non-acid-decomposable chained alkyl group having 4 or more carbon atoms, which may include a heteroatom, include a butyl group, a pentyl group, a hexyl group, a heptyl group, an octyl group, a nonyl group, a decyl group, a lauryl group, a stearyl group, an isobutyl group, a sec-butyl group, a 1-ethylpentyl group, a 2-ethylhexyl group, and a monovalent alkyl group in which one or two or more of —$CH_2$-'s of the alkyl group are substituted with —O— or —O—CO—.

The number of carbon atoms of the non-acid-decomposable chained alkyl group having 4 or more carbon atoms, which may include a heteroatom, is preferably from 4 to 18, more preferably from 6 to 18, and still more preferably from 8 to 18.

In addition, the non-acid-decomposable chained alkyl group having 4 or more carbon atoms may have a substituent (for example, a substituent T).

The repeating unit B1 is preferably a repeating unit represented by General Formula (1-2).

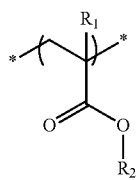

(1-2)

In General Formula (1-2), $R_1$ represents a hydrogen atom, a halogen atom, or an alkyl group. $R_2$ represents a non-acid-decomposable chained alkyl group having 4 or more carbon atoms, which may include a heteroatom.

The halogen atom represented by $R_1$ is not particularly limited, and examples thereof include a fluorine atom, a chlorine atom, a bromine atom, and an iodine atom.

The alkyl group represented by $R_1$ is not particularly limited, and examples thereof include an alkyl group having 1 to 10 carbon atoms, and specifically, a methyl group, an ethyl group, and a tert-butyl group. Among those, an alkyl group having 1 to 3 carbon atoms is preferable, and the methyl group is more preferable.

Among those, a hydrogen atom or a methyl group is preferable as $R_1$.

The definitions and the suitable aspects of the non-acid-decomposable chained alkyl group having 4 or more carbon atoms, which is represented by $R_2$ and may include a heteroatom are as described above.

Moreover, from the viewpoint that the residual solvent can be more easily volatilized, the repeating unit B1 may be a repeating unit having a non-acid-decomposable alkyl group, which has a carboxyl group or a hydroxyl group and may have a heteroatom.

Examples of a monomer constituting the repeating unit represented by General Formula (1-2) include ethyl acrylate (−22.0° C.), n-propyl acrylate (−37.0° C.), isopropyl acrylate (−5.0° C.), n-butyl acrylate (−55.0° C.), n-butyl methacrylate (20.0° C.), n-hexyl acrylate (−57.0° C.), n-hexyl methacrylate (−5.0° C.), n-octyl methacrylate (−20.0° C.), 2-ethylhexyl acrylate (−70.0° C.), isononyl acrylate (−82.0° C.), lauryl methacrylate (−65.0° C.), 2-hydroxyethyl acrylate (−15.0° C.), 2-hydroxypropyl methacrylate (26.0° C.), 1-[2-(methacryloyloxy)ethyl] succinate (9.0° C.), 2-ethylhexyl methacrylate (−10.0° C.), sec-butyl acrylate (−26.0° C.), methoxypolyethylene glycol monomethacrylate (n=2) (−20.0° C.), and hexadecyl acrylate (35.0° C.). Further, the Tg (° C.) of a homopolymer as formed from the monomer is in the parenthesis.

In addition, methoxypolyethylene glycol monomethacrylate (n=2) is a compound having the following structure.

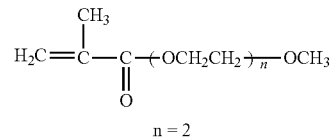

n = 2

The monomer B1 is preferably n-butyl acrylate, n-hexyl methacrylate, n-octyl methacrylate, 2-ethylhexyl methacrylate, or lauryl methacrylate, more preferably 2-ethylhexyl methacrylate or lauryl methacrylate, and still more preferably lauryl methacrylate.

The resin (A) may include one kind or two or more kinds of the repeating units B1.

The content of the repeating unit B1 in the resin (A) is preferably 5% by mole or more, more preferably 5% to 70% by mole, still more preferably 5% to 40% by mole, and particularly preferably 5% to 20% by mole, with respect to all the repeating units in the resin (A).

[Hansen Solubility Parameter (HSP) of Resin (A)]

The Hansen solubility parameter of the resin (A) is preferably 20.5 $(J/cm^3)^{0.5}$ or less, more preferably 15.0 to 20.5 $(J/cm^3)^{0.5}$, still more preferably 16.5 to 20.5 $(J/cm^3)^{0.5}$, and particularly preferably 17.5 to 20.5 $(J/cm^3)^{0.5}$.

Since the amount of the residual solvent in the film can be further reduced by setting the Hansen solubility parameter of the resin (A) to 20.5 $(J/cm^3)^{0.5}$ or less, the film peeling after a vacuum treatment can be further suppressed. In addition, the cross-sectional rectangularity of a pattern can be improved.

The Hansen solubility parameter of a resin is calculated by the following method.

(Method for Calculating Hansen Solubility Parameter of Resin (A))

The Hansen solubility parameter (HSP (A)) of the resin (A) was calculated as follows.

The Hansen solubility parameter for each of the repeating units constituting the resin (A) was calculated using a Hansen solubility parameter calculation Software; HSPiP version 4.1.07 (Hansen-Solubility.com), and multiplying a value obtained by squaring the Hansen solubility parameter of each repeating unit by the weight ratio of each repeating unit to take a square root. In addition, the Hansen solubility parameter of each repeating unit is a Hansen solubility parameter of a monomer corresponding to each repeating unit and is determined with the calculation software.

More specifically, in a case where the repeating units constituting the resin (A) are defined as (a), (b), (c), . . . , the Hansen solubility parameters (HSP (a), HSP (b), HSP (c), . . . ) of each repeating unit is calculated using the calculation software. In a case where the weight percentages of the repeating units (a), (b), (c), . . . constituting the resin (A) are defined as wt % (a), wt % (b), wt % (c), . . . , the Hansen solubility parameter (HSP (A)) of the resin (A) was calculated by the following equation.

$$HSP(A) = [\{HSP(a)\}^2 \times wt\%(a) + \{HSP(b)\}^2 \times wt\%(b) + \{HSP(c)\}^2 \times wt\%(c) + \ldots]^{1/2}/100$$

The resin (A) preferably has a repeating unit having a Hansen solubility parameter of 19.5 $(J/cm^3)^{0.5}$ or less (also referred to as a "repeating unit C1").

Examples of a monomer corresponding to the repeating unit C1 include isobornyl methacrylate (17.0), n-butyl methacrylate (17.3), n-hexyl methacrylate (16.9), n-octyl methacrylate (16.3), lauryl methacrylate (15.7), 2-ethylhexyl methacrylate (16.5), styrene (18.3), and benzyl methacrylate (18.7). Further, the value [unit: $(J/cm^3)^{0.5}$] of HSP is shown in the parenthesis.

The monomer corresponding to the repeating unit C1 is preferably n-butyl acrylate, n-hexyl methacrylate, n-octyl methacrylate, 2-ethylhexyl methacrylate, or lauryl methacrylate, more preferably 2-ethylhexyl methacrylate or lauryl methacrylate, and still more preferably lauryl methacrylate.

The resin (A) more preferably has a repeating unit having Hansen solubility parameter of 16.0 $(J/cm^3)^{0.5}$ or less, and still more preferably has a repeating unit having Hansen solubility parameter of 12.0 to 16.0 $(J/cm^3)^{0.5}$, as the repeating unit C1.

Since the amount of the residual solvent is further reduced by effectively reducing the Hansen solubility parameter of the resin (A), the content of the repeating unit C1 in the resin (A) is preferably 5% by mole or more, more preferably 5% to 70% by mole, still more preferably 5% to 40% by mole, and particularly preferably 5% to 20% by mole, with respect to all the repeating units in the resin (A).

It is preferable that the above-mentioned repeating unit B1 and repeating unit C1 are the same repeating units in the resin (A). That is, it is preferable that the resin (A) has a repeating unit (also referred to as a "repeating unit BC1") having a Hansen solubility parameter of 19.5 $(J/cm^3)^{0.5}$ or less and derived from a monomer allowing a homopolymer formed therefrom to have a glass transition temperature of 50° C. or lower.

The repeating unit BC1 is preferably the above-mentioned repeating unit represented by General Formula (1-2).

The monomer corresponding to the repeating unit BC1 is preferably n-butyl acrylate, n-hexyl methacrylate, n-octyl methacrylate, 2-ethylhexyl methacrylate, or lauryl methacrylate, more preferably 2-ethylhexyl methacrylate or lauryl methacrylate, and still more preferably lauryl methacrylate.

The resin (A) more preferably has a repeating unit derived from a monomer allowing a homopolymer formed therefrom to have a glass transition temperature of −20° C. or lower as the repeating unit BC1.

Furthermore, the resin (A) more preferably has a repeating unit having a Hansen solubility parameter of 16.0 $(J/cm^3)^{0.5}$ or less, and still preferably has a repeating unit having a Hansen solubility parameter of 12.0 to 16.0 $(J/cm^3)^{0.5}$, as the repeating unit BC1.

The content of the repeating unit BC1 in the resin (A) is preferably 5% by mole or more, more preferably 5% to 70% by mole, still more preferably 5% to 40% by mole, and particularly preferably 5% to 20% by mole, with respect to all the repeating units in the resin (A).

(Repeating Unit Having Acidic Group)

The resin (A) has a repeating unit having an acidic group.

From the viewpoint that the cross-sectional rectangularity of a pattern can be improved by increasing a solubility, the acidic group is preferably a carboxyl group, a phenolic hydroxyl group, or a sulfo group, more preferably the carboxyl group or the phenolic hydroxyl group, and still more preferably the phenolic hydroxyl group.

The resin (A) may have only one kind or two or more kinds of the repeating units having an acidic group in combination.

The content of the repeating unit having an acidic group in the resin (A) is 15% by mole or more, and preferably 45% by mole or more, with respect to all the repeating units in the resin (A).

The content of the repeating unit having an acidic group in the resin (A) is preferably 15% to 90% by mole, more preferably 30% to 90% by mole, and still more preferably 45% to 90% by mole, with respect to all the repeating units in the resin (A).

The repeating unit having a carboxyl group is not particularly limited, but examples thereof include repeating units derived from (meth)acrylic acids shown below.

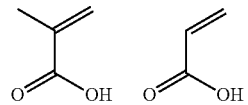

Furthermore, other examples of the repeating unit having a carboxyl group include a repeating unit having the following structure.

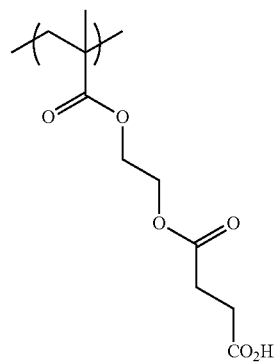

The repeating unit having a phenolic hydroxyl group is not particularly limited, but examples thereof include a hydroxystyrene repeating unit and a hydroxystyrene (meth)acrylate repeating unit. As the repeating unit having a phenolic hydroxyl group, a repeating unit represented by General Formula (I) is preferable.

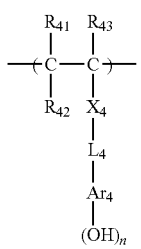

(I)

In the formula, $R_{41}$, $R_{42}$, and $R_{43}$ each independently represent a hydrogen atom, an alkyl group, a cycloalkyl group, a halogen atom, a cyano group, or an alkoxycarbonyl group. It should be noted that $R_{42}$ may be bonded to $Ar_4$ to form a ring, and in this case, $R_{42}$ represents a single bond or alkylene group.

$X_4$ represents a single bond, —COO—, or —$CONR_{64}$—, and $R_{64}$ represents a hydrogen atom or an alkyl group.

$L_4$ represents a single bond or a divalent linking group.

$Ar_4$ represents an (n+1)-valent aromatic hydrocarbon group, and in a case where $Ar_4$ is bonded to $R_{42}$ to form a ring, $Ar_4$ represents an (n+2)-valent aromatic hydrocarbon group.

n represents an integer of 1 to 5.

For the purpose of enhancing the polarity of the repeating unit represented by General Formula (I), it is also preferable that n is an integer of 2 or more, or $X_4$ is —COO— or —$CONR_{64}$—.

As the alkyl group represented by $R_{41}$, $R_{42}$, and $R_{43}$ in General Formula (I), an alkyl group having 20 or less carbon atoms, such as a methyl group, an ethyl group, a propyl group, an isopropyl group, an n-butyl group, a sec-butyl group, a hexyl group, a 2-ethylhexyl group, an octyl group, and a dodecyl group, which may have a substituent, is preferable, an alkyl group having 8 or less carbon atoms is more preferable, and an alkyl group having 3 or less carbon atoms is still more preferable.

The cycloalkyl group represented by each of $R_{41}$, $R_{42}$, and $R_{43}$ in General Formula (I) may be monocyclic or polycyclic. Among those, a monocyclic cycloalkyl group having 3 to 8 carbon atoms, such as a cyclopropyl group, a cyclopentyl group, and a cyclohexyl group, which may have a substituent, is preferable.

Examples of the halogen atom represented by each of $R_{41}$, $R_{42}$, and $R_{43}$ in General Formula (I) include a fluorine atom, a chlorine atom, a bromine atom, and an iodine atom, and the fluorine atom is preferable.

As the alkyl group included in the alkoxycarbonyl group represented by each of $R_{41}$, $R_{42}$, and $R_{43}$ in General Formula (I), the same ones as the alkyl group in each of $R_{41}$, $R_{42}$, and $R_{43}$ are preferable.

Preferred examples of the substituent in each of the groups include an alkyl group, a cycloalkyl group, an aryl group, an amino group, an amido group, a ureido group, a urethane group, a hydroxyl group, a carboxyl group, a halogen atom, an alkoxy group, a thioether group, an acyl group, an acyloxy group, an alkoxycarbonyl group, a cyano group, and a nitro group, and the number of carbon atoms of the substituent is preferably 8 or less.

$Ar_4$ represents an (n+1)-valent aromatic hydrocarbon group. The divalent aromatic hydrocarbon group in a case where n is 1 may have a substituent, and it is preferably, for example, an arylene group having 6 to 18 carbon atoms, such as a phenylene group, a tolylene group, a naphthylene group, and an anthracenylene group, or an aromatic hydrocarbon group including a heterocycle, such as thiophene, furan, pyrrole, benzothiophene, benzofuran, benzopyrrole, triazine, imidazole, benzimidazole, triazole, thiadiazole, and thiazole.

Specific examples of the (n+1)-valent aromatic hydrocarbon group in a case where n is an integer of 2 or more suitably include groups formed by excluding any (n−1) hydrogen atoms from the above-mentioned specific examples of the divalent aromatic hydrocarbon group.

The (n+1)-valent aromatic hydrocarbon group may further have a substituent.

Examples of the substituent which can be contained in the above-mentioned alkyl group, cycloalkyl group, alkoxycarbonyl group, and (n+1)-valent aromatic hydrocarbon group include the alkyl groups mentioned in each of $R_{41}$, $R_{42}$, and $R_{43}$ in General Formula (I); alkoxy groups such as a methoxy group, an ethoxy group, a hydroxyethoxy group, a propoxy group, a hydroxypropoxy group, and a butoxy group; and aryl groups such as a phenyl group.

As the alkyl group of $R_{64}$ in —$CONR_{64}$— ($R_{64}$ represents a hydrogen atom or an alkyl group) represented by $X_4$, an alkyl group having 20 or less carbon atoms, such as a methyl group, an ethyl group, a propyl group, an isopropyl group, an n-butyl group, a sec-butyl group, a hexyl group, a 2-ethylhexyl group, an octyl group, and a dodecyl group, which may have a substituent, is preferable, and an alkyl group having 8 or less carbon atoms is more preferable.

As $X_4$, a single bond, —COO—, or —CONH— is preferable, and the single bond or —COO— is more preferable.

As the divalent linking group as $L_4$, an alkylene group is preferable, and as the alkylene group, an alkylene group having 1 to 8 carbon atoms, such as a methylene group, an ethylene group, a propylene group, a butylene group, a hexylene group, and an octylene group, which may have a substituent, is preferable.

As $Ar_4$, an aromatic hydrocarbon group having 6 to 18 carbon atoms, which may have a substituent, is preferable, and a benzene ring group, a naphthalene ring group, or a biphenylene ring group is more preferable. Among those, the repeating unit represented by General Formula (I) is preferably a repeating unit derived from hydroxystyrene. That is, $Ar_4$ is preferably a benzene ring group.

Specific examples of the repeating unit having a phenolic hydroxyl group are shown below, but the present invention is not limited thereto. In the formulae, a represents 1 or 2.

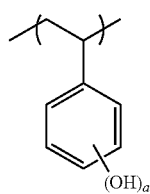

(B-1)

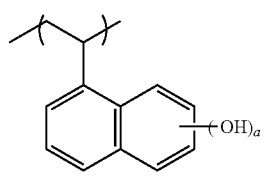

(B-2)

(B-3) 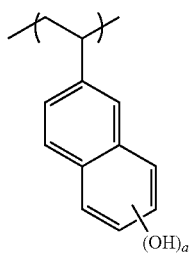
(B-4) 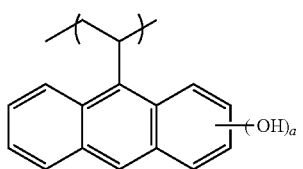
(B-5) 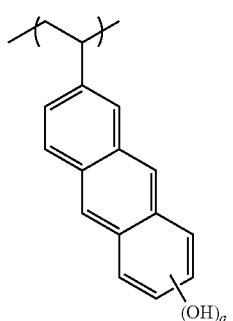
(B-6) 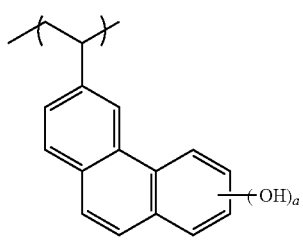
(B-7) 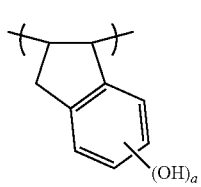
(B-8) 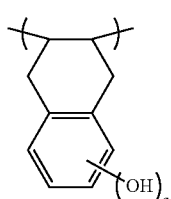
(B-9) 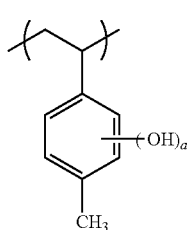
(B-10) 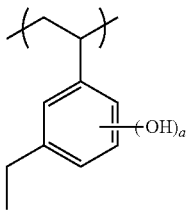
(B-11) 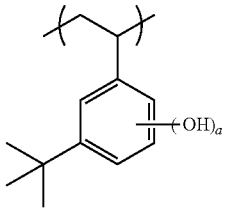
(B-12) 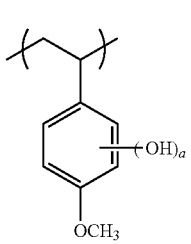
(B-13) 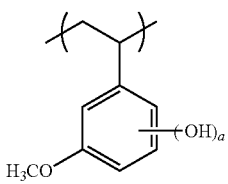
(B-14) 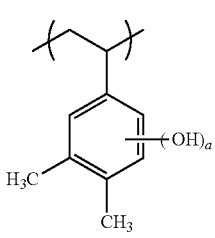
(B-15) 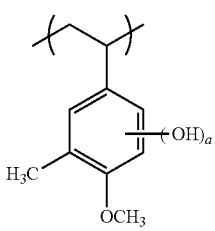
(B-16) 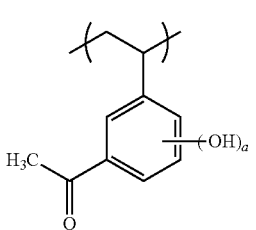

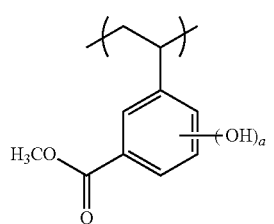 (B-17)
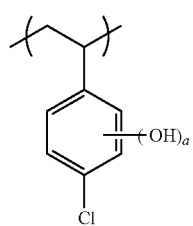 (B-18)
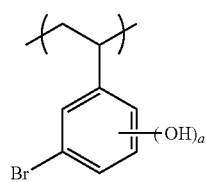 (B-19)
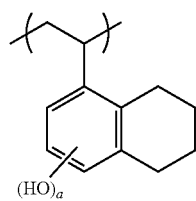 (B-20)
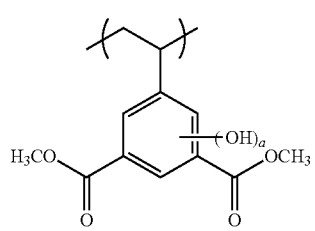 (B-21)
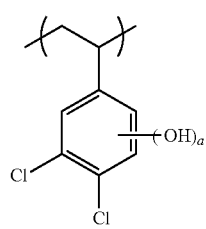 (B-22)
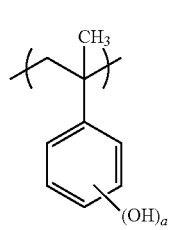 (B-23)
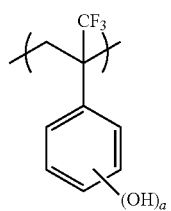 (B-24)
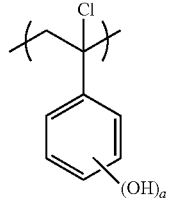 (B-25)
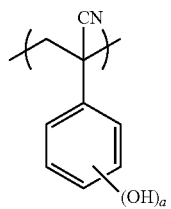 (B-26)
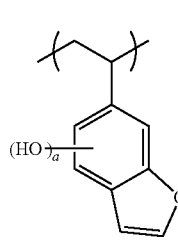 (B-27)
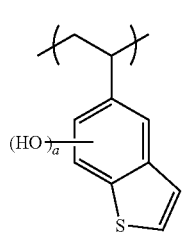 (B-28)
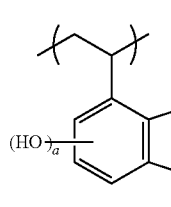 (B-29)
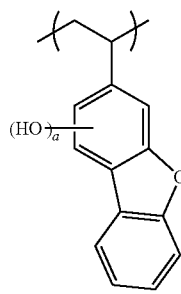 (B-30)

-continued

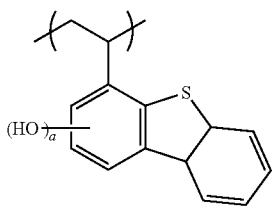
(B-31)

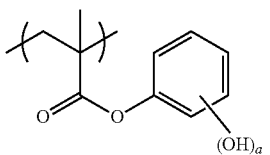
(B-32)

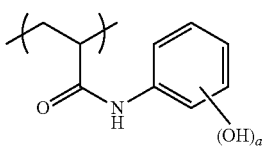
(B-33)

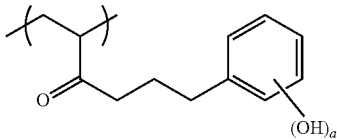
(B-34)

(Repeating Unit Having Acid-Decomposable Group)

The resin (A) has a repeating unit having an acid-decomposable group.

The resin (A) may have only one kind or two or more kinds of the repeating units having an acid-decomposable group in combination.

The content of the repeating unit having an acid-decomposable group in the resin (A) is more than 20% by mole, preferably 21% to 90% by mole, more preferably 21% to 75% by mole, and still more preferably 21% to 60% by mole, with respect to all the repeating units in the resin (A).

The acid-decomposable group preferably has a structure in which a polar group is protected with a group (leaving group) that leaves through decomposition by the action of an acid.

Examples of the polar group include an acidic group (a group that dissociates in a 2.38%-by-mass aqueous tetramethylammonium hydroxide solution) such as a carboxyl group, a phenolic hydroxyl group, a fluorinated alcohol group, a sulfo group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, and a tris(alkylsulfonyl)methylene group, and an alcoholic hydroxyl group.

Moreover, the alcoholic hydroxyl group refers to a hydroxyl group bonded to a hydrocarbon group, which is a hydroxyl group other than a hydroxyl group (phenolic hydroxyl group) directly bonded to an aromatic ring, from which an aliphatic alcohol (for example, a hexafluoroisopropanol group) having the α-position substituted with an electron withdrawing group such as a fluorine atom is excluded as a hydroxyl group. The alcoholic hydroxyl group is preferably a hydroxyl group having an acid dissociation constant (pKa) from 12 to 20.

Preferred examples of the polar group include a carboxyl group, a phenolic hydroxyl group, a fluorinated alcohol group (preferably a hexafluoroisopropanol group), and a sulfonic acid group.

A group which is preferable as the acid-decomposable group is a group in which a hydrogen atom of the leaving group is substituted with a group that leaves by the action of an acid.

Examples of the group (leaving group) that leaves by the action of an acid include —C($R_{36}$)($R_{37}$)($R_{38}$), —C($R_{36}$)($R_{37}$)(O$R_{39}$), and —C($R_{01}$)($R_{02}$)(O$R_{39}$).

In the formulae, $R_{36}$ to $R_{39}$ each independently represent an alkyl group, a cycloalkyl group, an aryl group, an aralkyl group, or an alkenyl group. $R_{36}$ and $R_{37}$ may be bonded to each other to form a ring.

$R_{01}$ and $R_{02}$ each independently represent a hydrogen atom, an alkyl group, a cycloalkyl group, an aryl group, an aralkyl group, or an alkenyl group.

As the alkyl group of each of $R_{36}$ to $R_{39}$, $R_{01}$, and $R_{02}$, an alkyl group having 1 to 8 carbon atoms is preferable, and examples thereof include a methyl group, an ethyl group, a propyl group, an n-butyl group, a sec-butyl group, a hexyl group, and an octyl group.

The cycloalkyl group of each of $R_{36}$ to $R_{39}$, $R_{01}$, and $R_{02}$ may be either a monocycle or a polycycle. As the monocyclic cycloalkyl group, a cycloalkyl group having 3 to 8 carbon atoms is preferable, and examples thereof include a cyclopropyl group, a cyclobutyl group, a cyclopentyl group, a cyclohexyl group, and a cyclooctyl group. As the polycyclic cycloalkyl group, a cycloalkyl group having 6 to 20 carbon atoms is preferable, and examples thereof include an adamantyl group, a norbornyl group, an isobornyl group, a camphonyl group, a dicyclopentyl group, an α-pinel group, a tricyclodecanyl group, a tetracyclododecyl group, and an androstanyl group. Further, at least one carbon atom in the cycloalkyl group may be substituted with a heteroatom such as an oxygen atom.

The aryl group of each of $R_{36}$ to $R_{39}$, $R_{01}$, and $R_{02}$ is preferably an aryl group having 6 to 10 carbon atoms, and examples thereof include a phenyl group, a naphthyl group, and an anthryl group.

The aralkyl group of each of $R_{36}$ to $R_{39}$, $R_{01}$, and $R_{02}$ is preferably an aralkyl group having 7 to 12 carbon atoms, and examples thereof include a benzyl group, a phenethyl group, and a naphthylmethyl group.

The alkenyl group of each of $R_{36}$ to $R_{39}$, $R_{01}$, and $R_{02}$ is preferably an alkenyl group having 2 to 8 carbon atoms, and examples thereof include a vinyl group, an allyl group, a butenyl group, and a cyclohexenyl group.

As the ring formed by the bonding of $R_{36}$ and $R_{37}$, a (monocyclic or polycyclic) cycloalkyl group is preferable. As the cycloalkyl group, a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group is preferable.

The acid-decomposable group is preferably a cumyl ester group, an enol ester group, an acetal ester group, a tertiary alkyl ester group, or the like, and more preferably an acetal group or a tertiary alkyl ester group.

Repeating Unit Having Structure (Acid-Decomposable Group) in which —COO— Group is Protected with Leaving Group that Leaves Through Decomposition by Action of Acid The resin (A) preferably has a repeating unit represented by General Formula (AI) as the repeating unit having an acid-decomposable group.

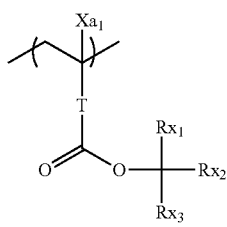

(AI)

In General Formula (AI), $Xa_1$ represents a hydrogen atom, a halogen atom, or a monovalent organic group.

T represents a single bond or a divalent linking group.

$Rx_1$ to $Rx_3$ each independently represent an alkyl group or a cycloalkyl group.

Any two of $Rx_1$ to $Rx_3$ may or may not be bonded to each other to form a ring structure.

Examples of the divalent linking group of T include an alkylene group, an arylene group, —COO-Rt-, and —O-Rt-. In the formulae, Rt represents an alkylene group, a cycloalkylene group, or an arylene group.

T is preferably the single bond or —COO-Rt-. Rt is preferably an alkylene group having 1 to 5 carbon atoms, and more preferably —$CH_2$—, —$(CH_2)_2$—, or —$(CH_2)_3$—. T is more preferably the single bond.

$Xa_1$ is preferably the hydrogen atom or the alkyl group.

The alkyl group of $Xa_1$ may have a substituent, and examples of the substituent include a hydroxyl group and a halogen atom (preferably a fluorine atom).

The alkyl group of $Xa_1$ preferably has 1 to 4 carbon atoms, and examples thereof include a methyl group, an ethyl group, a propyl group, a hydroxymethyl group, and a trifluoromethyl group. The alkyl group of $Xa_1$ is preferably the methyl group.

The alkyl group of each of $Rx_1$, $Rx_2$, and $Rx_3$ may be linear or branched, and is preferably a methyl group, an ethyl group, an n-propyl group, an isopropyl group, an n-butyl group, an isobutyl group, a t-butyl group, or the like. The number of the carbon atoms of the alkyl group is preferably 1 to 10, more preferably 1 to 5, and still more preferably 1 to 3. The alkyl group of each of $Rx_1$, $Rx_2$, and $Rx_3$ may have some of carbon-carbon bonds that are double-bonded.

As the cycloalkyl group of each of $Rx_1$, $Rx_2$, and $Rx_3$, a monocycle cycloalkyl group such as a cyclopentyl group and a cyclohexyl group, or a polycyclic cycloalkyl group such as a norbornyl group, a tetracyclodecanyl group, a tetracyclododecanyl group, and an adamantyl group is preferable.

As the ring structure formed by the bonding of two of $Rx_1$, $Rx_2$, and $Rx_3$, a monocycle cycloalkane ring such as a cyclopentyl ring, a cyclohexyl ring, a cycloheptyl ring, and a cyclooctane ring, or a polycyclic cycloalkyl ring such as a norbornane ring, a tetracyclodecane ring, a tetracyclododecane ring, and an adamantane ring is preferable. Among those, the cyclopentyl ring, the cyclohexyl ring, or the adamantane ring is more preferable. As the ring structure formed by the bonding of two of $Rx_1$, $Rx_2$, and $Rx_3$, a structure shown below is also preferable.

Specific examples of a monomer corresponding to the repeating unit represented by General Formula (AI) are shown below, but the present invention is not limited to these specific examples. The following specific examples correspond to a case where $Xa_1$ in General Formula (AI) is a methyl group, but $Xa_1$ can be optionally substituted with a hydrogen atom, a halogen atom, or a monovalent organic group.

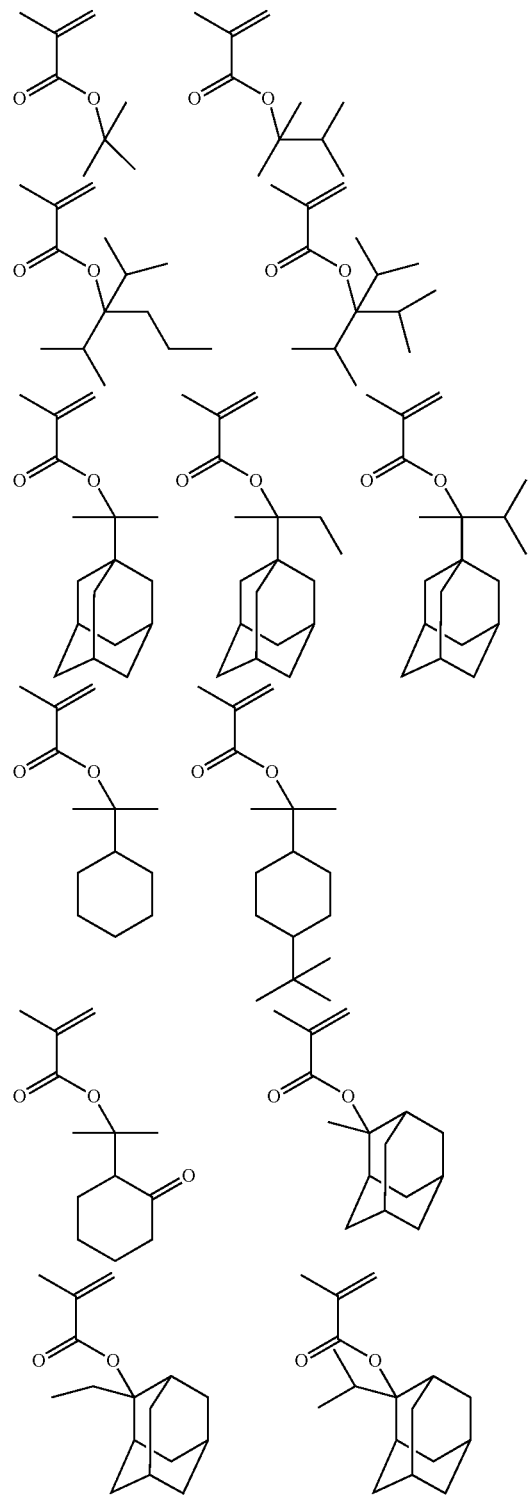

-continued

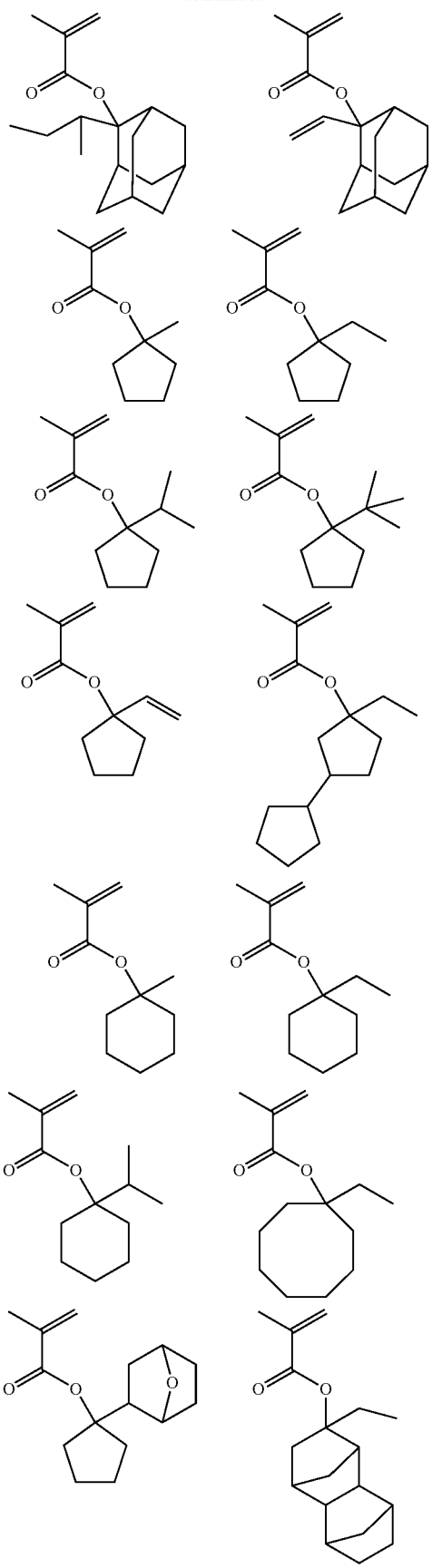

-continued

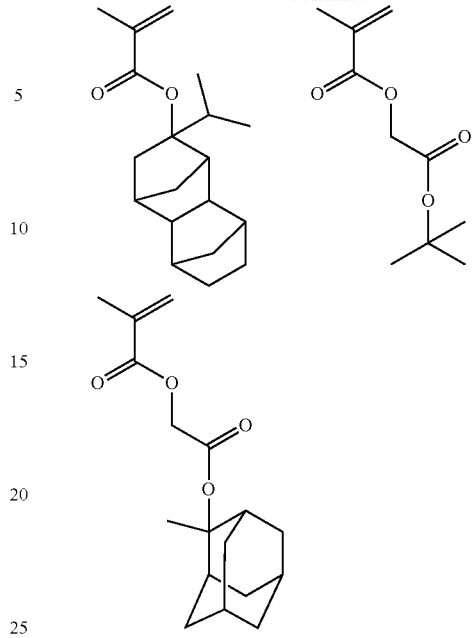

It is also preferable that the resin (A) has the repeating unit described in paragraphs [0336] to [0369] of US2016/0070167A1 as the repeating unit having an acid-decomposable group.

Moreover, the resin (A) may have a repeating unit including a group that generates an alcoholic hydroxyl group through decomposition by the action of an acid, described in paragraphs [0363] or [0364] of US2016/0070167A1, as the repeating unit having an acid-decomposable group.

Repeating Unit Having Structure (Acid-Decomposable Group) in which Phenolic Hydroxyl Group is Protected with Leaving Group that Leaves Through Decomposition by Action of Acid The resin (A) preferably has a repeating unit having a structure in which a phenolic hydroxyl group is protected with a leaving group that leaves through decomposition by the action of an acid as the repeating unit having an acid-decomposable group. Further, in the present specification, the phenolic hydroxyl group is a group formed by substituting a hydrogen atom of an aromatic hydrocarbon group with a hydroxyl group. The aromatic ring of the aromatic hydrocarbon group is a monocyclic or polycyclic aromatic ring, and examples thereof include a benzene ring and a naphthalene ring.

Examples of the leaving group that leaves through decomposition by the action of an acid include groups represented by Formulae (Y1) to (Y4).

| | |
|---|---|
| —C($Rx_1$)($Rx_2$)($Rx_3$) | Formula (Y1): |
| —C(=O)OC($Rx_1$)($Rx_2$)($Rx_3$) | Formula (Y2): |
| —C($R_{36}$)($R_{37}$)(O$R_{38}$) | Formula (Y3): |
| —C(Rn)(H)(Ar) | Formula (Y4): |

In Formulae (Y1) and (Y2), $Rx_1$ to $Rx_3$ each independently represent an (linear or branched) alkyl group or a (monocyclic or polycyclic) cycloalkyl group. It should be noted that in a case where all of $Rx_1$ to $Rx_3$ are (linear or branched) alkyl groups, it is preferable that at least two of $Rx_1$, . . . , or $Rx_3$ are methyl groups.

Among those, it is preferable that $Rx_1$ to $Rx_3$ are each independently a repeating unit representing a linear or branched alkyl group, and it is more preferable that $Rx_1$ to $Rx_3$ are each independently a repeating unit representing a linear alkyl group.

Two of $Rx_1$ to $Rx_3$ may be bond to each other to form a monocycle or a polycycle.

As the alkyl group of each of $Rx_1$ to $Rx_3$, an alkyl group having 1 to 4 carbon atoms, such as a methyl group, an ethyl group, an n-propyl group, an isopropyl group, an n-butyl group, an isobutyl group, and a t-butyl group, is preferable.

As the cycloalkyl group of each of $Rx_1$ to $Rx_3$, a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group is preferable.

As the cycloalkyl group formed by the bonding of two of $Rx_1$ to $Rx_3$, a monocyclic cycloalkyl group such as a cyclopentyl group and a cyclohexyl group, or a polycyclic cycloalkyl group such as a norbornyl group, a tetracyclodecanyl group, a tetracyclododecanyl group, and an adamantyl group is preferable. A monocyclic cycloalkyl group having 5 or 6 carbon atoms is more preferable.

In the cycloalkyl group formed by the bonding of two of $Rx_1$ to $Rx_3$, for example, one methylene group constituting the ring may be substituted with a heteroatom such as an oxygen atom or a group having a heteroatom, such as a carbonyl group.

For the group represented by each of Formulae (Y1) and (Y2), for example, an aspect in which $Rx_1$ is a methyl group or an ethyl group, and $Rx_2$ and $Rx_3$ are bonded to each other to form the above-mentioned cycloalkyl group is preferable.

In Formula (Y3), $R_{36}$ to $R_{38}$ each independently represent a hydrogen atom or a monovalent organic group. $R_{37}$ and $R_{38}$ may be bonded to each other to form a ring. Examples of the monovalent organic group include an alkyl group, a cycloalkyl group, an aryl group, an aralkyl group, and an alkenyl group. $R_{36}$ is also preferably the hydrogen atom.

In Formula (Y4), Ar represents an aromatic hydrocarbon group. Rn represents an alkyl group, a cycloalkyl group, or an aryl group. Rn and Ar may be bonded to each other to form a non-aromatic ring. Ar is more preferably an aryl group.

The repeating unit having a structure (acid-decomposable group) in which a phenolic hydroxyl group is protected with a leaving group that leaves through decomposition by the action of an acid preferably has a structure in which a hydrogen atom in the phenolic hydroxyl group is protected with a group represented by any of Formulae (Y1) to (Y4).

As the repeating unit having a structure (acid-decomposable group) in which a phenolic hydroxyl group is protected with a leaving group that leaves through decomposition by the action of an acid, a repeating unit represented by General Formula (AII) is preferable.

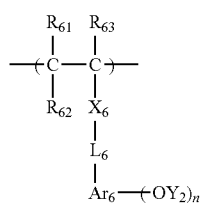

(AII)

In General Formula (AII), $R_{61}$, $R_{62}$, and $R_{63}$ each independently represent a hydrogen atom, an alkyl group, a cycloalkyl group, a halogen atom, a cyano group, or an alkoxycarbonyl group. It should be noted that $R_{62}$ may be bonded to $Ar_6$ to form a ring, and in this case, $R_{62}$ represents a single bond or an alkylene group.

$X_6$ represents a single bond, —COO—, or —$CONR_{64}$—. $R_{64}$ represents a hydrogen atom or an alkyl group.

$L_6$ represents a single bond or an alkylene group.

$Ar_6$ represents an (n+1)-valent aromatic hydrocarbon group, and in a case where $Ar_6$ is bonded to $R_{62}$ to form a ring, $Ar_6$ represents an (n+2)-valent aromatic hydrocarbon group.

In a case of n≥2, Y2's each independently represent a hydrogen atom or a group that leaves by the action of an acid. It should be noted that at least one of Y2's represents a group that leaves by the action of an acid. The group that leaves by the action of an acid as Y2 is preferably a group of any one of Formulae (Y1) to (Y4).

n represents an integer of 1 to 4.

Each of the groups may have a substituent, and examples of the substituent include an alkyl group (having 1 to 4 carbon atoms), a halogen atom, a hydroxyl group, an alkoxy group (having 1 to 4 carbon atoms), a carboxyl group, and an alkoxycarbonyl group (having 2 to 6 carbon atoms), and the number of carbon atoms of the substituent is preferably 8 or less.

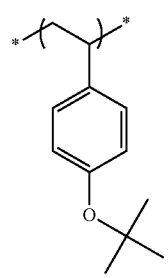

(VI-1)

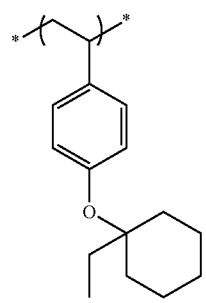

(VI-2)

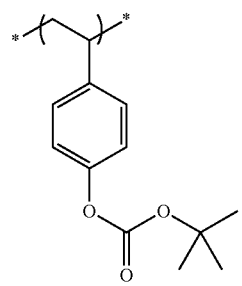

(VI-3)

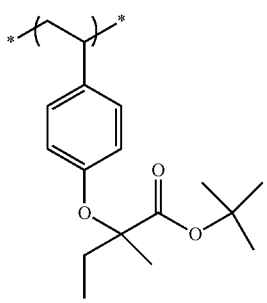 (VI-4)
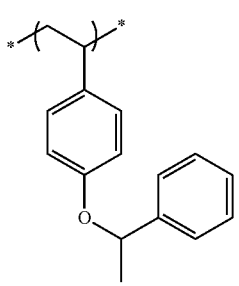 (VI-5)
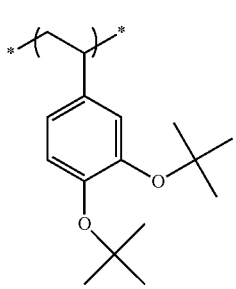 (VI-6)
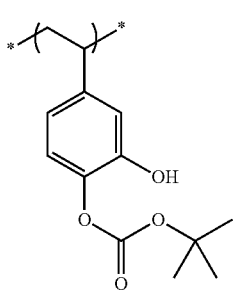 (VI-7)
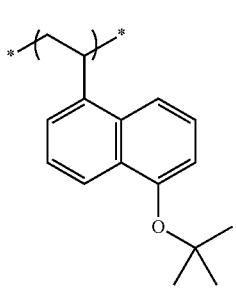 (VI-8)
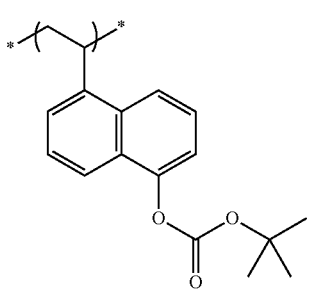 (VI-9)
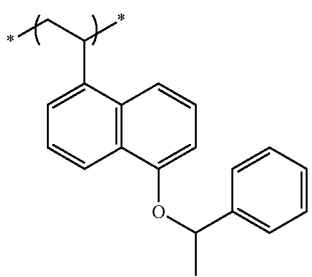 (VI-10)
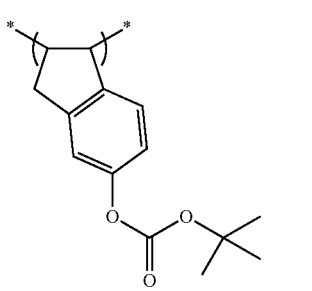 (VI-11)
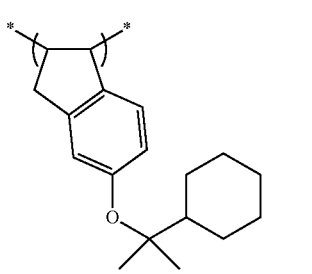 (VI-12)
(VI-13)
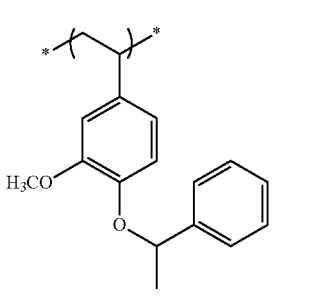 (VI-14)

(VI-15)
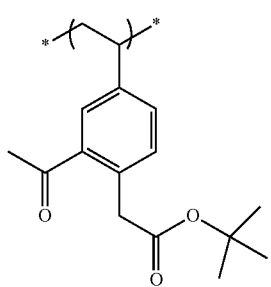
(VI-16)
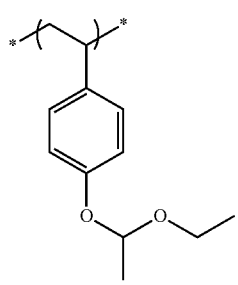
(VI-17)
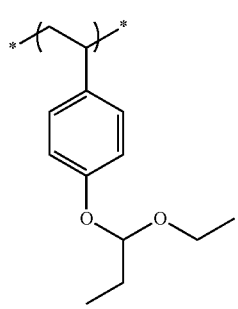
(VI-18)
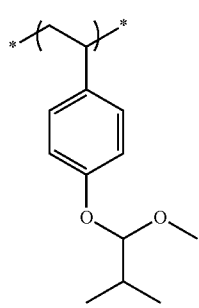
(VI-19)
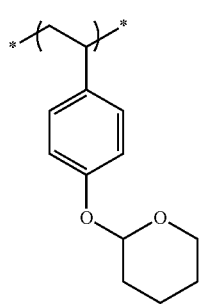
(VI-20)
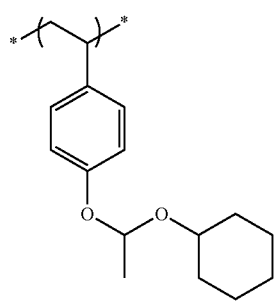
(VI-21)
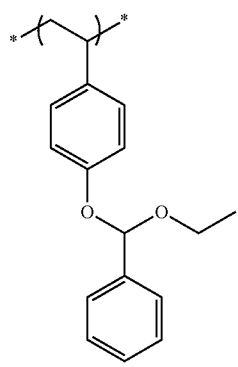
(VI-22)
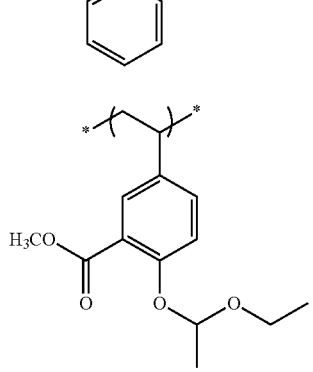
(VI-23)
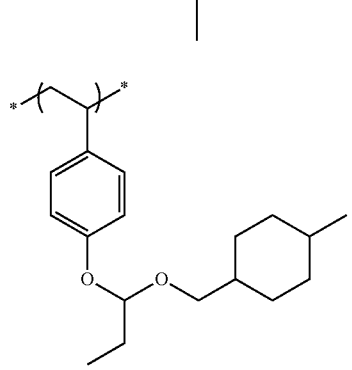
(VI-24)
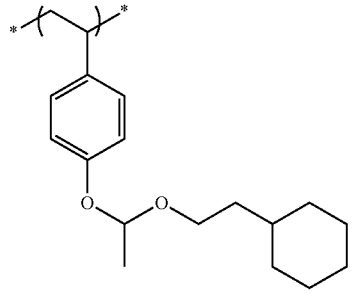

(VI-25) 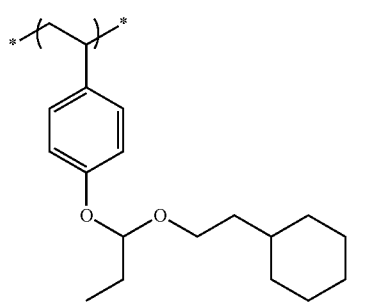
(VI-26) 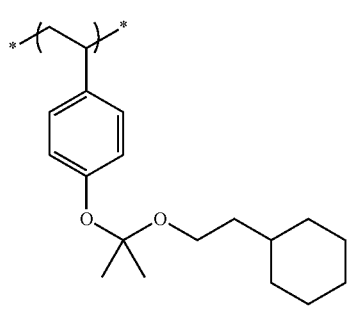
(VI-27) 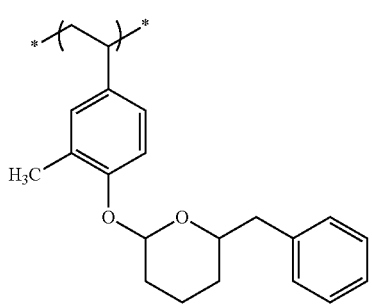
(VI-28) 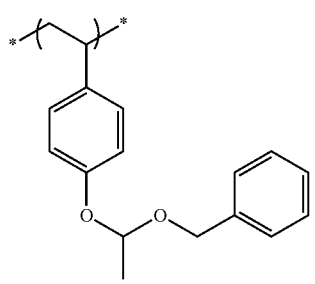
(VI-29) 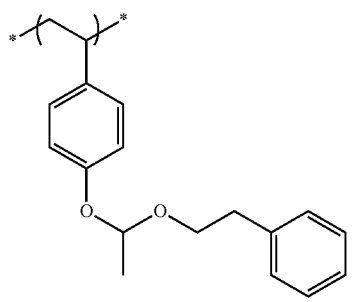
(VI-30) 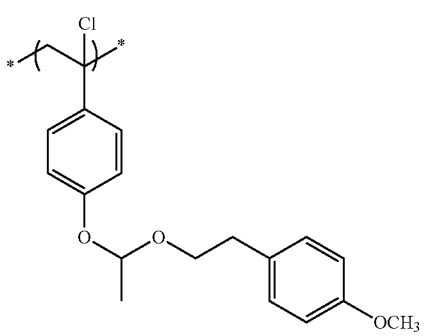
(VI-31) 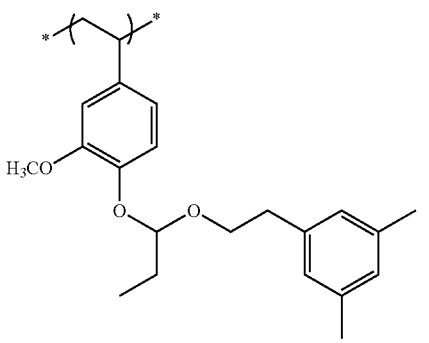
(VI-32) 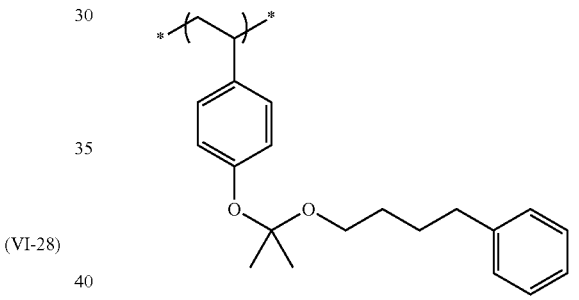
(VI-33) 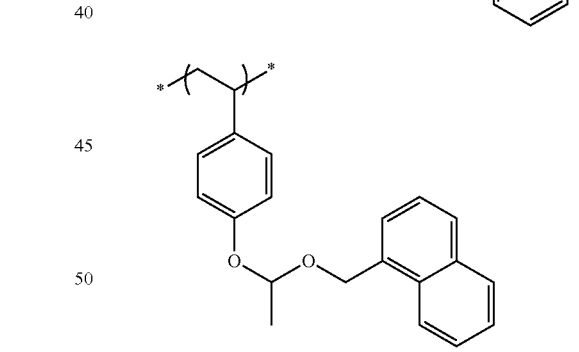
(VI-34) 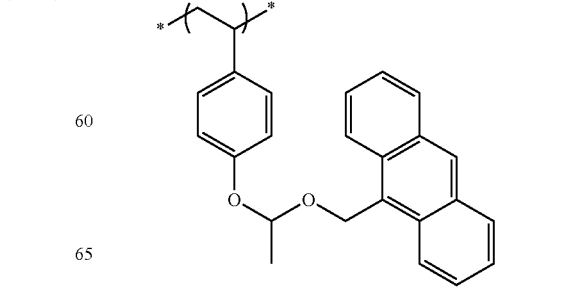

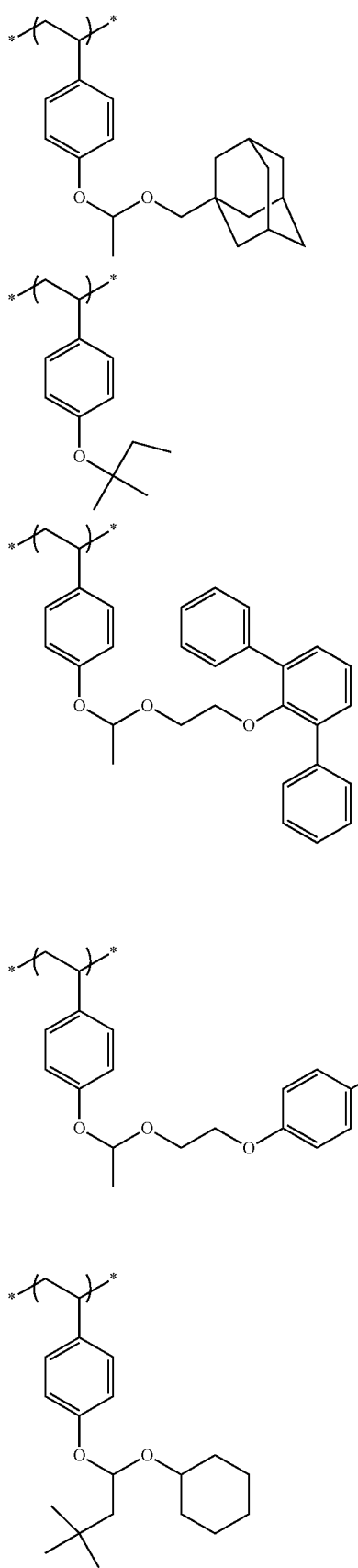
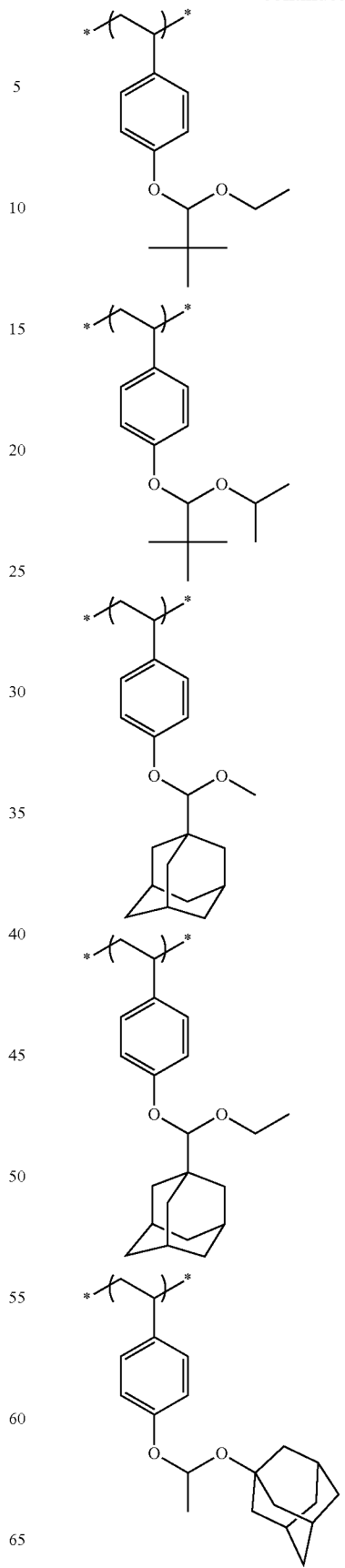
(VI-35)

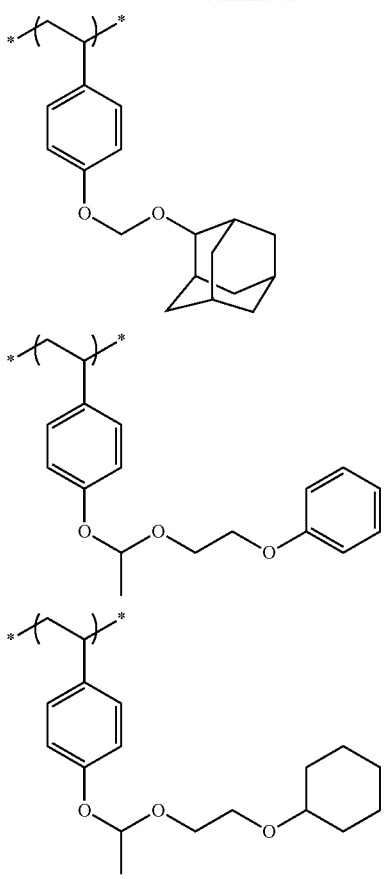

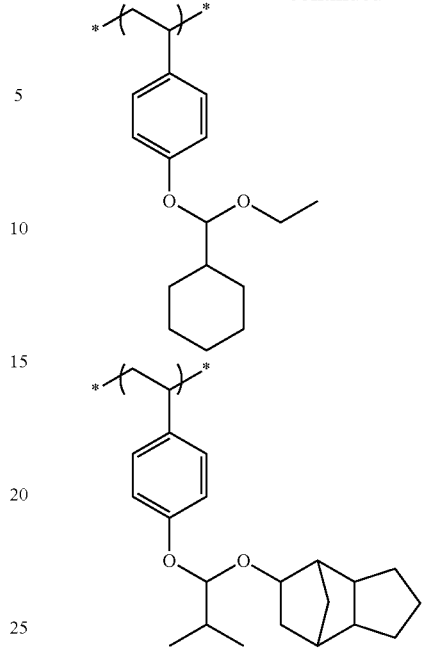

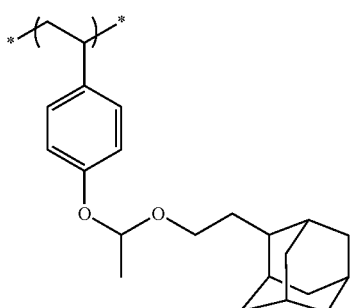

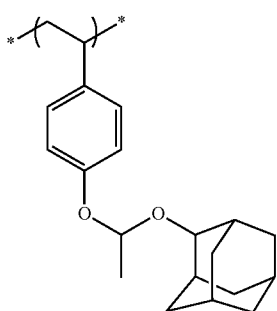

(Other Repeating Units)

The resin (A) may contain other repeating units, in addition to the above-mentioned repeating units.

Such other repeating units that can be contained in the resin (A) will be described in detail.

The resin (A) preferably has a repeating unit having at least one selected from the group consisting of a lactone structure, a sultone structure, and a carbonate structure.

As the lactone structure or the sultone structure, any structure is available as long as it has a lactone structure or sultone structure, but the structure is preferably a 5- to 7-membered ring lactone structure or a 5- to 7-membered ring sultone structure. Among those, the structure is more preferably a 5- to 7-membered ring lactone structure to which another ring structure is fused in the form of forming a bicyclo structure or a spiro structure or a 5- to 7-membered ring sultone structure to which another ring structure is fused in the form of forming a bicyclo structure or a spiro structure.

The resin (A) still more preferably has a repeating unit having a lactone structure represented by any one of General Formulae (LC1-1) to (LC1-21) or a sultone structure represented by any one of General Formulae (SL1-1) to (SL1-3). Further, the lactone structure or sultone structure may be bonded directly to the main chain. Preferred examples of the structure include a lactone structure represented by General Formula (LC1-1), General Formula (LC1-4), General Formula (LC1-5), General Formula (LC1-8), General Formula (LC1-16), or General Formula (LC1-21), or a sultone structure represented by General Formula (SL1-1).

LC1-1

LC1-2
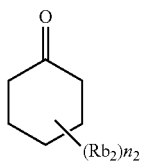
LC1-3
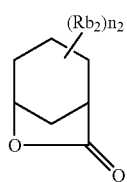
LC1-4
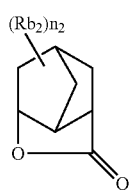
LC1-5
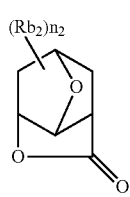
LC1-6
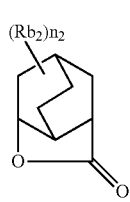
LC1-7
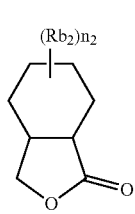
LC1-8
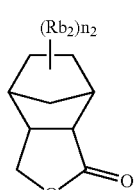
LC1-9
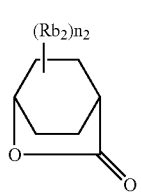
LC1-10
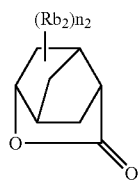
LC1-11
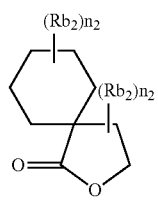
LC1-12
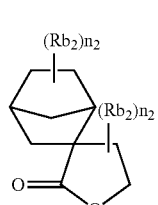
LC1-13
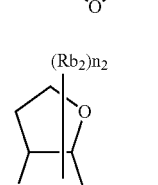
LC1-14
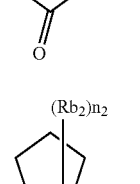
LC1-15
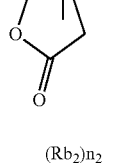
LC1-16
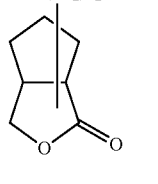
LC1-17
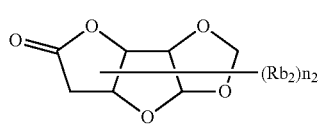

LC1-18 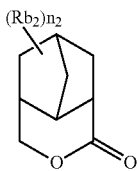

LC1-19 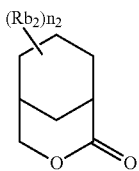

LC1-20 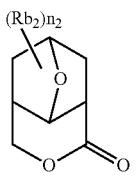

LC1-21 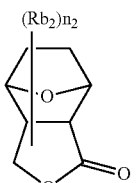

SL1-1 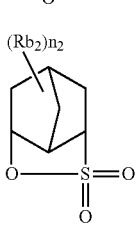

SL1-2 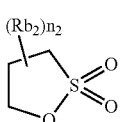

SL1-3 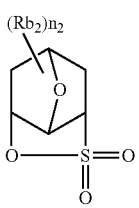

The lactone structural moiety or the sultone structural moiety may or may not have a substituent ($Rb_2$). Preferred examples of the substituent ($Rb_2$) include an alkyl group having 1 to 8 carbon atoms, a cycloalkyl group having 4 to 7 carbon atoms, an alkoxy group having 1 to 8 carbon atoms, an alkoxycarbonyl group having 2 to 8 carbon atoms, a carboxyl group, a halogen atom, a hydroxyl group, a cyano group, and an acid-decomposable group, and the substituent ($Rb_2$) is preferably an alkyl group having 1 to 4 carbon atoms, the cyano group, or the acid-decomposable group. $n_2$ represents an integer of 0 to 4. In a case where $n_2$ is 2 or more, the substituents ($Rb_2$) which are present in plural number may be the same as or different from each other.

Further, the substituents ($Rb_2$) which are present in plural number may be bonded to each other to form a ring.

As the repeating unit having a lactone structure or a sultone structure, a repeating unit represented by General Formula (III) is preferable.

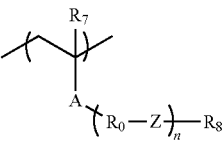

(III)

In General Formula (III),

A represents an ester bond (a group represented by —COO—) or an amide bond (a group represented by —CONH—).

n is the repetition number of the structure represented by —$R_0$—Z—, represents an integer of 0 to 5, and is preferably 0 or 1, and more preferably 0. In a case where n is 0, —$R_0$—Z— is not present, and thus the structure has a single bond.

$R_0$ represents an alkylene group, a cycloalkylene group, or a combination thereof. In a case where a plurality of $R_0$'s are present, $R_0$'s each independently represent an alkylene group, a cycloalkylene group, or a combination thereof.

Z represents a single bond, an ether bond, an ester bond, an amide bond, a urethane bond, or a urea bond. In a case where a plurality of Z's are present, Z's each independently represent a single bond, an ether bond, an ester bond, an amide bond, a urethane bond, or a urea bond.

$R_8$ represents a monovalent organic group having a lactone structure or a sultone structure.

$R_7$ represents a hydrogen atom, a halogen atom, or a monovalent organic group (preferably a methyl group).

The alkylene group or the cycloalkylene group of $R_0$ may have a substituent.

As Z, the ether bond or the ester bond is preferable, and the ester bond is more preferable.

The resin (A) may have a repeating unit having a carbonate structure. The carbonate structure is preferably a cyclic carbonate ester structure.

The repeating unit having a cyclic carbonate ester structure is preferably a repeating unit represented by General Formula (A-1).

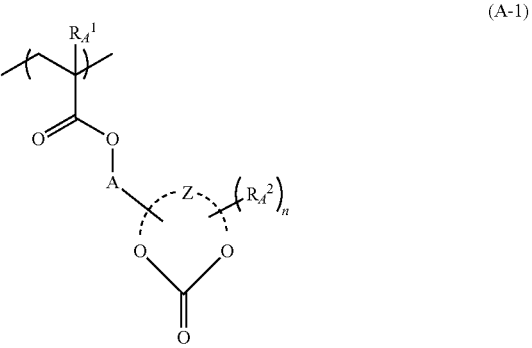

(A-1)

In General Formula (A-1), $R_A^1$ represents a hydrogen atom, a halogen atom, or a monovalent organic group (preferably a methyl group).

n represents an integer of 0 or more.

$R_A^2$ represents a substituent. In a case where n is 2 or more, $R_A^2$'s each independently represent a substituent.

A represents a single bond or a divalent linking group.

Z represents an atomic group which forms a monocyclic structure or a polycyclic structure together with a group represented by —O—C(=O)—O— in the formula.

It is also preferable that the resin (A) has the repeating unit described in paragraphs [0370] to [0414] of US2016/0070167A1 as the repeating unit having at least one selected from the group consisting of a lactone structure, a sultone structure, and a carbonate structure.

The resin (A) may have only one kind or two or more kinds of repeating units having at least one selected from the group consisting of a lactone structure, a sultone structure, and a carbonate structure.

Specific examples of a monomer corresponding to the repeating unit represented by General Formula (III) and specific examples of a monomer corresponding to the repeating unit represented by General Formula (A-1) are shown below, but the present invention is not limited to these specific examples. The following specific examples correspond to a case where $R_7$ in General Formula (III) and $R_A^1$ in General Formula (A-1) are each a methyl group, but $R_7$ and $R_A^1$ may be optionally substituted with a hydrogen atom, a halogen atom, or a monovalent organic group.

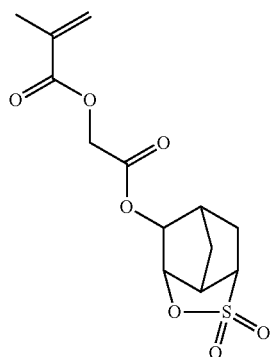

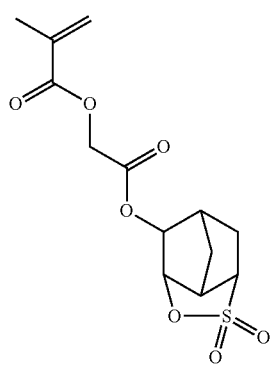

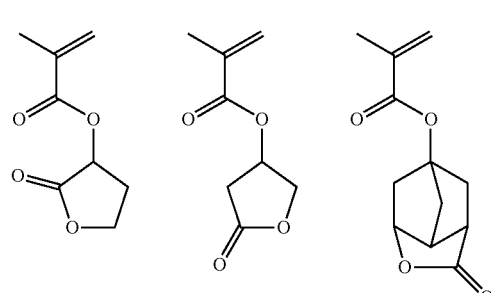

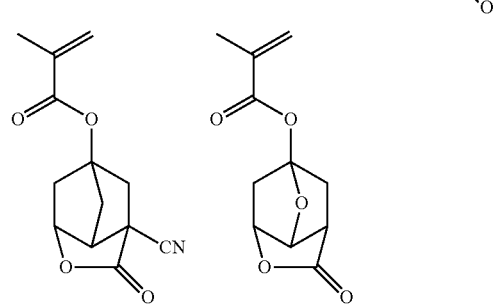

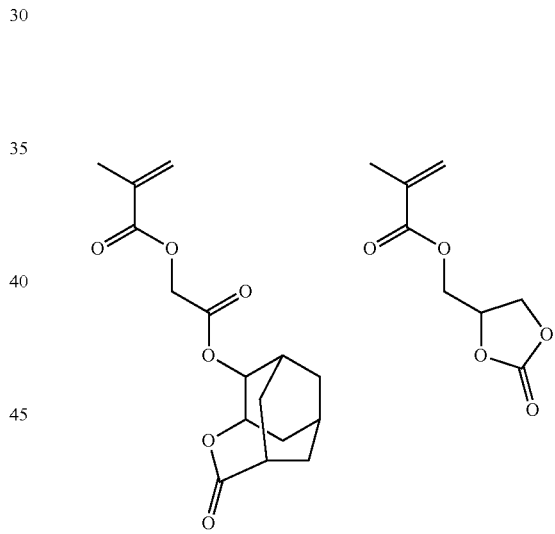

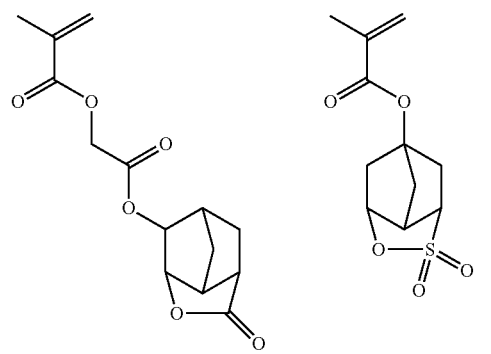

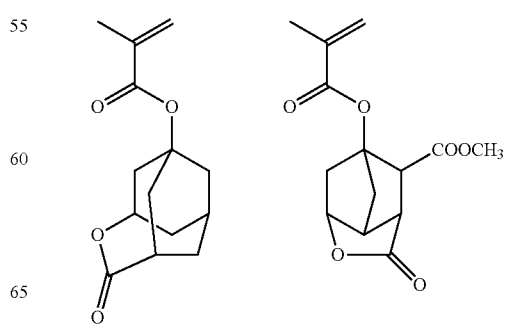

-continued

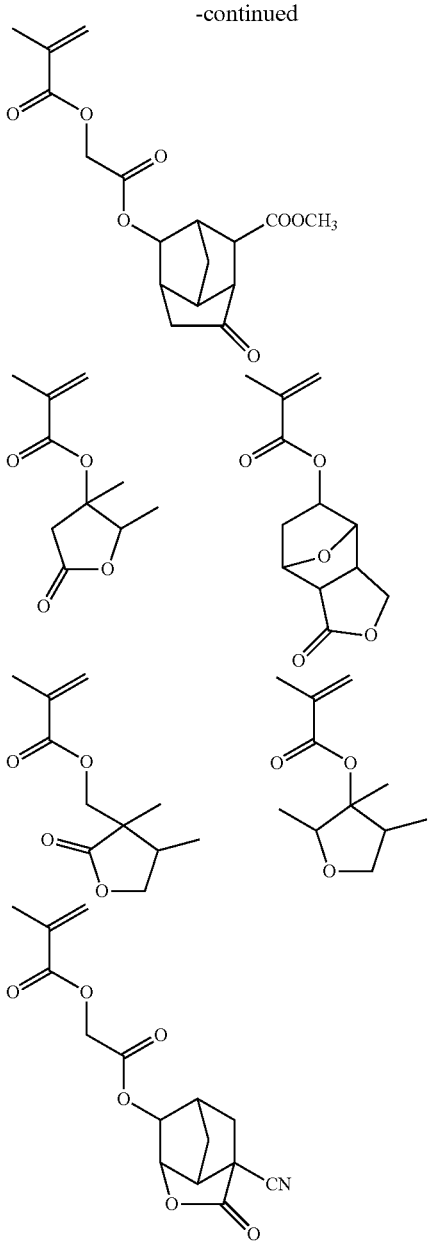

In addition to the monomers, monomers shown below are also suitably used as a raw material of the resin (A).

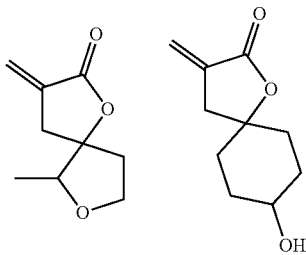

The content of the repeating unit having at least one selected from the group consisting of a lactone structure, a sultone structure, and a carbonate structure included in the resin (A) (a total of the contents in a case where a plurality of the repeating units having at least one selected from the group consisting of a lactone structure, a sultone structure, and a carbonate structure are present) is preferably 5% to 30% by mole, more preferably 10% to 30% by mole, and still more preferably 20% to 30% by mole, with respect to all the repeating units in the resin (A).

The resin (A) may further have a variety of repeating structural units, in addition to the repeating structural units, for the purpose of controlling dry etching resistance, suitability for a standard developer, adhesiveness to a substrate, a resist profile, or resolving power, heat resistance, sensitivity, and the like which are general characteristics required for a resist.

Examples of such a repeating structural unit include, but are not limited to, a repeating structural unit corresponding to a predetermined monomer.

Examples of such a predetermined monomer include a compound having one addition-polymerizable unsaturated bond, which is selected from acrylic acid esters, methacrylic acid esters, acrylamides, methacrylamides, allyl compounds, vinyl ethers, vinyl esters, and the like.

In addition to these, an addition-polymerizable unsaturated compound that is copolymerizable with the monomers corresponding to various repeating structural units as described above may be copolymerized.

In the resin (A), the molar ratio of each repeating structural unit contained is appropriately set in order to control various types of performance.

In the resin (A), it is preferable that all the repeating units are constituted with (meth)acrylate-based repeating units. In this case, any of a resin in which all of the repeating units are methacrylate-based repeating units, a resin in which all of the repeating units are acrylate-based repeating units, and a resin in which all of the repeating units are methacrylate-based repeating units and acrylate-based repeating units can be used, but it is preferable that the acrylate-based repeating units account for 50% by mole or less of all of the repeating units of the resin (A).

(Repeating Unit Having Aromatic Ring)

For the resin (A), it is preferable that at least one of the repeating units of the resin (A) is a repeating unit having an aromatic ring.

In the resin (A), from the viewpoint that the etching resistance is more excellent, the content of the repeating unit having an aromatic ring is, for example, 40% by mole or more, preferably 55% by mole or more, and more preferably 60% by mole or more, with respect to all the repeating units in the resin (A). In addition, an upper limit thereof is not particularly limited, but is, for example, 97% by mole or less, preferably 85% by mole or less, and more preferably 80% by mole or less.

It is particularly preferable that the resin (A) contains a repeating unit represented by General Formula (1-2), a repeating unit represented by General Formula (1-3), and a repeating unit represented by General Formula (1-4).

(1-2)

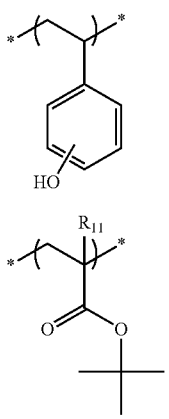

(1-3)

(1-4)

In General Formula (1-2), $R_1$ represents a hydrogen atom, a halogen atom, or an alkyl group. $R_2$ represents a non-acid-decomposable chained alkyl group having 4 or more carbon atoms, which may include a heteroatom.

In General Formula (1-4), Ru represents a hydrogen atom, a halogen atom, or an alkyl group.

General Formula (1-2) is the same as described above. In General Formula (1-4), $R_{11}$ has the same definition as $R_1$ in General Formula (1-2) and a preferred range thereof is also the same.

(Method for Polymerizing Resin (A))

The resin (A) can be synthesized in accordance with an ordinary method (for example, radical polymerization). Examples of the general synthesis method include (1) a batch polymerization method in which polymerization is performed by dissolving monomer species and an initiator in a solvent and heating the solution, and (2) a dropwise addition polymerization method in which a solution containing monomer species and an initiator is added to a heating solvent through dropwise addition for 1 to 10 hours, and among these, the (2) dropwise addition polymerization method is preferable.

Examples of the reaction solvent during polymerization include ethers such as tetrahydrofuran, 1,4-dioxane, and diisopropyl ether, ketones such as methyl ethyl ketone and methyl isobutyl ketone, ester solvents such as ethyl acetate, amides such as dimethyl formamide and dimethyl acetamide, and a solvent which dissolves the composition of the embodiment of the present invention, such as propylene glycol monomethyl ether acetate (PGMEA), propylene glycol monomethyl ether (PGME), and cyclohexanone which will be described later. Among those, the same solvent as the solvent used in the composition of the embodiment of the present invention is preferably used as the reaction solvent in the polymerization. With a use of the solvent, generation of the particles during storage can be suppressed.

The polymerization reaction is preferably performed in an inert gas atmosphere such as nitrogen and argon. In the polymerization reaction, a commercially available radical initiator (for example, an azo-based initiator and a peroxide) is preferably used as the polymerization initiator. As the radical initiator, an azo-based initiator is preferable, and an azo-based initiator having an ester group, a cyano group, or a carboxyl group is more preferable. Examples of such the azo-based initiator include azobisisobutyronitrile, azobisdimethylvaleronitrile, and dimethyl 2,2'-azobis(2-methyl propionate).

For the polymerization reaction, a polymerization initiator may be optionally added as described above. A method for adding the polymerization initiator into a system is not particularly limited, and it may be in either an aspect in which a polymerization initiator is added at once or an aspect in which a polymerization initiator is dividedly added in portionwise. During the polymerization reaction, the concentration of the solid content of the reaction solution is usually 5% to 60% by mass, and preferably 10% to 50% by mass. The reaction temperature is usually 10° C. to 150° C., preferably 30° C. to 120° C., and more preferably 60° C. to 100° C. After completion of the reaction, a polymer is recovered by a method such as a method in which the reaction solution is put into a solvent to recover a powder or a solid content.

The weight-average molecular weight of the resin (A) is preferably 1,000 to 200,000, more preferably 2,000 to 30,000, and still more preferably 3,000 to 25,000. The dispersity (Mw/Mn) is usually 1.0 to 3.0, preferably 1.0 to 2.6, more preferably 1.0 to 2.0, and still particularly preferably 1.1 to 2.0.

The resin (A) may be used singly or in combination of two or more kinds thereof.

The content of the resin (A) in the composition of the embodiment of the present invention is generally 20% by mass or more in many cases, and is preferably 40% by mass or more, more preferably 60% by mass or more, and still more preferably 80% by mass or more, with respect to the total solid content. An upper limit thereof is not particularly limited, but is preferably 99.5% by mass or less, more preferably 99% by mass or less, and still more preferably 98% by mass or less.

(Concentration of Solid Content)

The actinic ray-sensitive or radiation-sensitive resin composition of the embodiment of the present invention preferably has a concentration of a solid content of 10% by mass or more. As a result, for example, it becomes easier to form a pattern of a thick film having a film thickness of 2 μm or more (preferably 10 μm or more). Further, the concentration of the solid content is intended to mean a mass percentage of a mass of other resist components (components that can constitute a resist film) excluding the solvent with respect to the total mass of the composition of the embodiment of the present invention.

<Photoacid Generator>

It is preferable that the composition of the embodiment of the present invention typically a photoacid generator.

The photoacid generator is a compound that generates an acid upon irradiation with actinic rays or radiation.

As the photoacid generator, a compound that generates an organic acid upon irradiation with actinic rays or radiation is preferable. Examples thereof include a sulfonium salt compound, an iodonium salt compound, a diazonium salt compound, a phosphonium salt compound, an imidesulfonate compound, an oximesulfonate compound, a diazodisulfone compound, a disulfone compound, and an o-nitrobenzylsulfonate compound.

As the photoacid generator, known compounds that generate an acid upon irradiation with actinic rays or radiation can be appropriately selected and used singly or as a mixture thereof. For example, the known compounds disclosed in paragraphs [0125] to [0319] of US2016/0070167A1, paragraphs [0086] to [0094] of US2015/0004544A1, and paragraphs [0132] to [0402] of US2016/0237190A1 can be suitably used.

As the photoacid generator, for example, a compound represented by General Formula (ZI), General Formula (ZII), or General Formula (ZIII) is preferable.

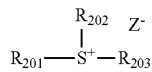

(ZI)

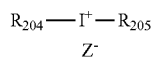

(ZII)

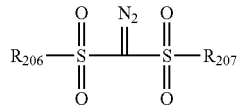

(ZIII)

In General Formula (ZI), $R_{201}$, $R_{202}$, and $R_{203}$ each independently represent an organic group.

The number of carbon atoms of the organic group as each of $R_{201}$, $R_{202}$, and $R_{203}$ is generally 1 to 30, and preferably 1 to 20.

In addition, two of $R_{201}$ to $R_{203}$ may be bonded to each other to form a ring structure, and the ring may include an oxygen atom, a sulfur atom, an ester bond, an amide bond, or a carbonyl group. Examples of the group formed by the bonding of two of $R_{201}$ to $R_{203}$ include an alkylene group (for example, a butylene group and a pentylene group) and —$CH_2$—$CH_2$—O—$CH_2$—$CH_2$—.

$Z^-$ represents an anion (which is preferably a non-nucleophilic anion).

Suitable aspects of the cation in General Formula (ZI) include the corresponding groups in a compound (ZI-1), a compound (ZI-2), a compound represented by General Formula (ZI-3) (compound (ZI-3)), and a compound represented by General Formula (ZI-4) (compound (ZI-4)), which will be described later.

In addition, the photoacid generator may be a compound having a plurality of the structures represented by General Formula (a). For example, it may be a compound having a structure in which at least one of $R_{201}$, . . . , or $R_{203}$ in the compound represented by General Formula (ZI) is bonded to at least one of $R_{201}$, . . . , or $R_{203}$ of another compound represented by General Formula (ZI) through a single bond or a linking group.

First, the compound (ZI-1) will be described.

The compound (ZI-1) is an arylsulfonium compound in which at least one of $R_{201}$, . . . , or $R_{203}$ in General Formula (ZI) is an aryl group, that is, a compound having arylsulfonium as a cation.

In the arylsulfonium compound, all of $R_{201}$ to $R_{203}$ may be aryl groups, or some of $R_{201}$ to $R_{203}$ may be aryl groups and the remainders may be alkyl groups or cycloalkyl groups.

Examples of the arylsulfonium compound include a triarylsulfonium compound, a diarylalkylsulfonium compound, an aryldialkylsulfonium compound, a diarylcycloalkylsulfonium compound, and an aryldicycloalkylsulfonium compound.

The aryl group included in the arylsulfonium compound is preferably a phenyl group or a naphthyl group, and more preferably the phenyl group. The aryl group may be an aryl group having a heterocyclic structure having an oxygen atom, a nitrogen atom, a sulfur atom, or the like. Examples of the heterocyclic structure include a pyrrole residue, a furan residue, a thiophene residue, an indole residue, a benzofuran residue, and a benzothiophene residue. In a case where the arylsulfonium compound has two or more aryl groups, these two or more aryl groups may be the same as or different from each other.

The alkyl group or the cycloalkyl group which may be contained, as desired, in the arylsulfonium compound, is preferably a linear alkyl group having 1 to 15 carbon atoms, a branched alkyl group having 3 to 15 carbon atoms, or a cycloalkyl group having 3 to 15 carbon atoms, and examples thereof include a methyl group, an ethyl group, a propyl group, an n-butyl group, a sec-butyl group, a t-butyl group, a cyclopropyl group, a cyclobutyl group, and a cyclohexyl group.

The aryl group, the alkyl group, and the cycloalkyl group of each of $R_{201}$ to $R_{203}$ may each independently have an alkyl group (for example, an alkyl group having 1 to 15 carbon atoms), a cycloalkyl group (for example, a cycloalkyl group having 3 to 15 carbon atoms), an aryl group (for example, an aryl group having 6 to 14 carbon atoms), an alkoxy group (for example, an alkoxy group having 1 to 15 carbon atoms), a halogen atom, a hydroxyl group, or a phenylthio group as a substituent.

Next, the compound (ZI-2) will be described.

The compound (ZI-2) is a compound in which $R_{201}$ to $R_{203}$ in Formula (ZI) each independently represent an organic group not having an aromatic ring. Here, the aromatic ring also encompasses an aromatic ring containing a heteroatom.

The organic group as each of $R_{201}$ to $R_{203}$, which contains no aromatic ring, has generally 1 to 30 carbon atoms, and preferably 1 to 20 carbon atoms.

$R_{201}$ to $R_{203}$ are each independently preferably an alkyl group, a cycloalkyl group, an allyl group, or a vinyl group, more preferably a linear or branched 2-oxoalkyl group, a 2-oxocycloalkyl group, or an alkoxycarbonylmethyl group, and still more preferably the linear or branched 2-oxoalkyl group.

Preferred examples of the alkyl group and the cycloalkyl group of each of $R_{201}$ to $R_{203}$ include a linear alkyl group having 1 to 10 carbon atoms or a branched alkyl group having 3 to 10 carbon atoms (for example, a methyl group, an ethyl group, a propyl group, a butyl group, and a pentyl group), and a cycloalkyl group having 3 to 10 carbon atoms (for example, a cyclopentyl group, a cyclohexyl group, and a norbornyl group).

$R_{201}$ to $R_{203}$ may further be substituted with a halogen atom, an alkoxy group (for example, an alkoxy group having 1 to 5 carbon atoms), a hydroxyl group, a cyano group, or a nitro group.

Next, the compound (ZI-3) will be described.

(ZI-3)

In General Formula (ZI-3), M represents an alkyl group, a cycloalkyl group, or an aryl group, and in a case where M has a ring structure, the ring structure may include at least one of an oxygen atom, a sulfur atom, an ester bond, an amide bond, or a carbon-carbon double bond. $R_{1c}$ and $R_{2c}$ each independently represent a hydrogen atom, an alkyl group, a cycloalkyl group, a halogen atom, a cyano group, or an aryl group. $R_{1c}$ and $R_{2c}$ may be bonded to each other to form a ring. $R_x$ and $R_y$ each independently represent an alkyl group, a cycloalkyl group, or an alkenyl group. $R_x$ and $R_y$ may be bonded to each other to form a ring. Further, at least two selected from M, $R_{1c}$, or $R_{2c}$ may be bonded to each other to form a ring structure, and the ring structure may include a carbon-carbon double bond. $Z^-$ represents an anion.

In General Formula (ZI-3), as each of the alkyl group and the cycloalkyl group represented by M, a linear alkyl group having 1 to 15 carbon atoms (preferably having 1 to 10 carbon atoms), a branched alkyl group having 3 to 15 carbon atoms (preferably having 3 to 10 carbon atoms), or a cycloalkyl group having 3 to 15 carbon atoms (preferably having 1 to 10 carbon atoms) is preferable, and specific examples of the alkyl group and the cycloalkyl group include a methyl group, an ethyl group, a propyl group, an n-butyl group, a sec-butyl group, a t-butyl group, a cyclopropyl group, a cyclobutyl group, a cyclohexyl group, and a norbornyl group.

As the aryl group represented by M, a phenyl group or a naphthyl group is preferable, and the phenyl group is more preferable. The aryl group may be an aryl group having a heterocyclic structure having an oxygen atom, a sulfur atom, or the like. Examples of the heterocyclic structure include a furan ring, a thiophene ring, a benzofuran ring, and a benzothiophene ring.

M may further have a substituent (for example, a substituent T). In this aspect, examples of M include a benzyl group.

In addition, in a case where M has a ring structure, the ring structure may include at least one of an oxygen atom, a sulfur atom, an ester bond, an amide bond, or a carbon-carbon double bond.

Examples of the alkyl group, the cycloalkyl group, and the aryl group represented by each of $R_{1c}$ and $R_{2c}$ include the same ones as those of M as mentioned above and preferred aspects thereof are also the same. In addition, $R_{1c}$ and $R_{2c}$ may be bonded to each other to form a ring.

Examples of the halogen atom represented by each of $R_{1c}$ and $R_{2c}$ include a fluorine atom, a chlorine atom, a bromine atom, and an iodine atom.

Examples of the alkyl group and the cycloalkyl group represented by each of $R_x$ and $R_y$ include the same ones as those of M as mentioned above and preferred aspects thereof are also the same.

As the alkenyl group represented by each of $R_x$ and $R_y$, an allyl group or a vinyl group is preferable.

$R_x$ and $R_y$ may further have a substituent (for example, a substituent T). In this aspect, examples of each of $R_x$ and $R_y$ include a 2-oxoalkyl group and an alkoxycarbonylalkyl group.

Examples of the 2-oxoalkyl group represented by each of $R_x$ and $R_y$ include a 2-oxoalkyl group having 1 to 15 carbon atoms (preferably having 1 to 10 carbon atoms), and specific examples of the 2-oxoalkyl group include a 2-oxopropyl group and a 2-oxobutyl group.

Examples of the alkoxycarbonylalkyl group represented by each of $R_x$ and $R_y$ include an alkoxycarbonylalkyl group having 1 to 15 carbon atoms (preferably having 1 to 10 carbon atoms). In addition, $R_x$ and $R_y$ may be bonded to each other to form a ring.

The ring structure formed by the mutual linking of $R_x$ and $R_y$ may include an oxygen atom, a sulfur atom, an ester bond, an amide bond, or a carbon-carbon double bond.

In General Formula (ZI-3), M and $R_{1c}$ may be bonded to each other to form a ring structure, and the ring structure thus formed may include a carbon-carbon double bond.

Among those, the compound (ZI-3) is preferably a compound (ZI-3A).

The compound (ZI-3A) is a compound represented by General Formula (ZI-3A), which has a phenacylsulfonium salt structure.

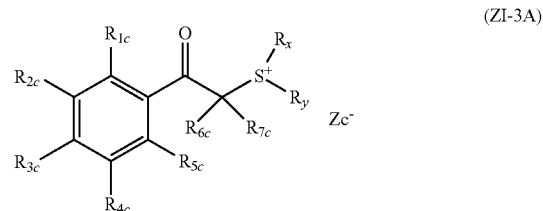

(ZI-3A)

In General Formula (ZI-3A), $R_{1c}$ to $R_{5c}$ each independently represent a hydrogen atom, an alkyl group, a cycloalkyl group, an aryl group, an alkoxy group, an aryloxy group, an alkoxycarbonyl group, an alkylcarbonyloxy group, a cycloalkylcarbonyloxy group, a halogen atom, a hydroxyl group, a nitro group, an alkylthio group, or an arylthio group.

$R_{6c}$ and $R_{7c}$ each have the same definitions as $R_{1c}$ and $R_{2c}$ in General Formula (ZI-3) described above and preferred aspects thereof are also the same.

$R_x$ and $R_y$ each have the same definitions as $R_x$ and $R_y$ in General Formula (ZI-3) described above and preferred aspects thereof are also the same.

Among any two or more of $R_{1c}$ to $R_{5c}$, and $R_x$ and $R_y$ each may be bonded to each other to form a ring structure, and the ring structure may each independently include an oxygen atom, a sulfur atom, an ester bond, an amide bond, or carbon-carbon double bond. Further, $R_{5c}$ and $R_{6c}$, and $R_{5c}$ and $R_x$ may be bonded to each other to form ring structures, and the ring structures each independently include a carbon-carbon double bond. In addition, $R_{6c}$ and $R_{7c}$ may be bonded to each other to form a ring structure.

Examples of the ring structure include an aromatic or non-aromatic hydrocarbon ring, an aromatic or non-aromatic heterocycle, or a polycyclic fused ring composed of two or more of these rings. Examples of the ring structure include 3- to 10-membered rings, and the ring structures are preferably 4- to 8-membered ring, and more preferably 5- or 6-membered rings.

Examples of groups formed by the bonding of any two or more of $R_{1c}$ to $R_{5c}$, $R_{6c}$ and $R_{7c}$, and $R_x$ and $R_y$ include a butylene group and a pentylene group.

As groups formed by the bonding of $R_{5c}$ and $R_{6c}$, and $R_{5c}$ and $R_x$, a single bond or an alkylene group is preferable. Examples of the alkylene group include a methylene group and an ethylene group.

$Zc^-$ represents an anion.

Next, the compound (ZI-4) will be described.

The compound (ZI-4) is represented by General Formula (ZI-4).

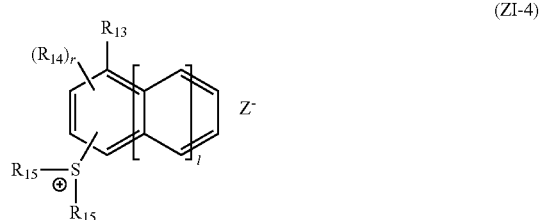

(ZI-4)

In General Formula (ZI-4), l represents an integer of 0 to 2. l is particularly preferably 0.

r represents an integer of 0 to 8.

$R_{13}$ represents a hydrogen atom, a fluorine atom, a hydroxyl group, an alkyl group, a cycloalkyl group, an alkoxy group, an alkoxycarbonyl group, or a group having a monocyclic or polycyclic cycloalkyl skeleton. These groups may have a substituent.

$R_{14}$ or $R_{14}$'s in a case where $R_{14}$'s are present in plural number each independently represent an alkyl group, a cycloalkyl group, an alkoxy group, an alkylsulfonyl group, a cycloalkylsulfonyl group, an alkylcarbonyl group, an alkoxycarbonyl group, or an alkoxy group having a monocyclic or polycyclic cycloalkyl skeleton. These groups may have a substituent.

$R_{15}$'s each independently represent an alkyl group, a cycloalkyl group, or a naphthyl group. These groups may have a substituent. Two $R_{15}$'s may be bonded to each other to form a ring. In a case where two $R_{15}$'s are bonded to form a ring, the ring skeleton may include a heteroatom such as an oxygen atom and a nitrogen atom. In one aspect, it is preferable that two $R_{15}$'s are alkylene groups, and are bonded to each other to form a ring structure.

$Z^-$ represents an anion.

In General Formula (ZI-4), the alkyl group of each of $R_{13}$, $R_{14}$, and $R_{15}$ is linear or branched. The number of carbon atoms of the alkyl group is preferably 1 to 10. As the alkyl group, a methyl group, an ethyl group, an n-butyl group, a t-butyl group, or the like is more preferable. Two $R_{15}$'s may be bonded to each other to form a ring and the number of ring members in a case where the ring is formed is preferably 5 or 6.

The ring in a case two $R_{15}$'s may be bonded to each other to form a ring may have a substituent. The substituent is not particularly limited, but examples thereof include a hydroxyl group, a halogen atom, an alkyl group, and an alkoxy group. The halogen atom is preferably a fluorine atom, a chlorine atom, a bromine atom, or an iodine atom, and more preferably the fluorine atom. The alkyl group may be linear or branched. The number of carbon atoms of the alkyl group is preferably 1 to 10, and more preferably 1 to 6. Examples of the alkyl group include a methyl group, an ethyl group, a propyl group, an n-butyl group, a sec-butyl group, and a t-butyl group. The alkyl group may have a substituent, the substituent is not particularly limited, but examples thereof include a halogen atom. The alkoxy group may be linear or branched. The number of carbon atoms of the alkoxy group is preferably 1 to 10, and more preferably 1 to 6. Examples of the alkoxy group include a methoxy group, an ethoxy group, and a tert-butoxy group. The alkoxy group may have a substituent, the substituent is not particularly limited, but examples thereof include an alkoxy group (for example, an alkoxy group having 1 to 6 carbon atoms) and a cycloalkyl group (for example, a cycloalkyl group having 5 to 10 carbon atoms).

Next, General Formulae (ZII) and (ZIII) will be described.

In General Formulae (ZI) and (ZIII), $R_{204}$ to $R_{207}$ each independently represent an aryl group, an alkyl group, or a cycloalkyl group.

As the aryl group of each of $R_{204}$ to $R_{207}$, a phenyl group or a naphthyl group is preferable, and the phenyl group is more preferable. The aryl group of each of $R_{204}$ to $R_{207}$ may be an aryl group having a heterocyclic structure having an oxygen atom, a nitrogen atom, a sulfur atom, or the like. Examples of the skeleton of the aryl group having a heterocyclic structure include pyrrole, furan, thiophene, indole, benzofuran, and benzothiophene.

Preferred examples of the alkyl group and the cycloalkyl group of each of $R_{204}$ to $R_{207}$ include a linear alkyl group having 1 to 10 carbon atoms or a branched alkyl group having 3 to 10 carbon atoms (for example, a methyl group, an ethyl group, a propyl group, a butyl group, and a pentyl group), and a cycloalkyl group having 3 to 10 carbon atoms (a cyclopentyl group, a cyclohexyl group, and a norbornyl group).

The aryl group, the alkyl group, and the cycloalkyl group of each of $R_{204}$ to $R_{207}$ may each independently have a substituent. Examples of the substituent which may be contained in the aryl group, the alkyl group, or the cycloalkyl group of each of $R_{204}$ to $R_{207}$ include an alkyl group (for example, having 1 to 15 carbon atoms), a cycloalkyl group (for example, having 3 to 15 carbon atoms), an aryl group (for example, having 6 to 15 carbon atoms), an alkoxy group (for example, having 1 to 15 carbon atoms), a halogen atom, a hydroxyl group, and a phenylthio group.

$Z^-$ represents an anion.

As $Z^-$ in General Formula (ZI), $Z^-$ in General Formula (III), $Z^-$ in General Formula (ZI-3), $Zc^-$ in General Formula (ZI-3A), and $Z^-$ in General Formula (ZI-4), an anion represented by General Formula (3) is preferable.

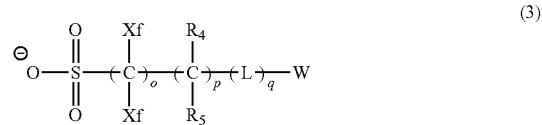

In General Formula (3), o represents an integer of 1 to 3. p represents an integer of 0 to 10. q represents an integer of 0 to 10.

Xf's represent a fluorine atom or an alkyl group substituted with at least one fluorine atom. The number of carbon atoms of the alkyl group is preferably 1 to 10, and more preferably 1 to 4. Further, as the alkyl group substituted with at least one fluorine atom, a perfluoroalkyl group is preferable.

Xf is preferably a fluorine atom or a perfluoroalkyl group having 1 to 4 carbon atoms, and more preferably a fluorine atom or $CF_3$. In particular, it is still more preferable that both Xf's are fluorine atoms.

$R_4$ and $R_5$ each independently represent a hydrogen atom, a fluorine atom, an alkyl group, or an alkyl group substituted with at least one fluorine atom. In a case where a plurality of each of $R_4$'s and $R_5$'s are present, $R_4$'s and $R_5$'s may be the same as or different from each other.

The alkyl group represented by each of $R_4$ and $R_5$ may have a substituent, and preferably has 1 to 4 carbon atoms. $R_4$ and $R_5$ are each preferably a hydrogen atom.

Specific examples and suitable embodiments of the alkyl group substituted with at least one fluorine atom are the same as the specific examples and the suitable embodiments of Xf in General Formula (3).

L represents a divalent linking group. In a case where a plurality of L's are present, L's may be the same as or different from each other.

Examples of the divalent linking group include —COO— (—C(=O)—O—), —OCO—, —CONH—, —NHCO—, —CO—, —O—, —S—, —SO—, —$SO_2$—, an alkylene group (preferably having 1 to 6 carbon atoms), a cycloalkylene group (preferably having 3 to 15 carbon atoms), an alkenylene group (preferably having 2 to 6 carbon atoms), or a divalent linking group formed by combination of these plurality of groups. Among these, —COO—, —OCO—, —CONH—, —NHCO—, —CO—, —O—, —SO$_2$—, —COO— alkylene group-, —OCO-alkylene group-, —CONH-alkylene group-, or —NHCO-alkylene group- is preferable, and —COO—, —OCO—, —CONH—, —SO$_2$—, —COO-alkylene group-, or —OCO-alkylene group- is more preferable.

W represents an organic group including a cyclic structure. Among these, a cyclic organic group is preferable.

Examples of the cyclic organic group include an alicyclic group, an aryl group, and a heterocyclic group.

The alicyclic group may be monocyclic or polycyclic. Examples of the monocyclic alicyclic group include monocyclic cycloalkyl groups such as a cyclopentyl group, a cyclohexyl group, and a cyclooctyl group. Examples of the polycyclic alicyclic group include polycyclic cycloalkyl groups such as a norbornyl group, a tricyclodecanyl group, a tetracyclodecanyl group, a tetracyclododecanyl group, and an adamantyl group. Among these, an alicyclic group having a bulky structure having 7 or more carbon atoms, such as a norbornyl group, a tricyclodecanyl group, a tetracyclodecanyl group, a tetracyclododecanyl group, and an adamantyl group is preferable.

The aryl group may be monocyclic or polycyclic. Examples of the aryl group include a phenyl group, a naphthyl group, a phenanthryl group, and an anthryl group.

The heterocyclic group may be monocyclic or polycyclic. In a case where it is polycyclic, it is possible to suppress acid diffusion. Further, the heterocyclic group may have aromaticity or may not have aromaticity. Examples of the heterocycle having aromaticity include a furan ring, a thiophene ring, a benzofuran ring, a benzothiophene ring, a dibenzofuran ring, a dibenzothiophene ring, and a pyridine ring. Examples of the heterocycle not having an aromaticity include a tetrahydropyran ring, a lactone ring, a sultone ring, and a decahydroisoquinoline ring. Examples of the lactone ring and the sultone ring include the above-mentioned lactone structures and sultone structures exemplified in the resin. As the heterocycle in the heterocyclic group, a furan ring, a thiophene ring, a pyridine ring, or a decahydroisoquinoline ring is particularly preferable.

The cyclic organic group may have a substituent. Examples of the substituent include, an alkyl group (which may be linear or branched, and preferably has 1 to 12 carbon atoms), a cycloalkyl group (which may be any one of a monocycle, a polycycle, and a spiro ring, and preferably has 3 to 20 carbon atoms), an aryl group (preferably having 6 to 14 carbon atoms), a hydroxyl group, an alkoxy group, an ester group, an amido group, a urethane group, a ureido group, a thioether group, a sulfonamido group, and a sulfonic acid ester group. Incidentally, the carbon constituting the cyclic organic group (carbon contributing to ring formation) may be carbonyl carbon.

As the anion represented by General Formula (3), SO$_3^-$—CF$_2$—CH$_2$—OCO-(L)q'-W, SO$_3^-$—CF$_2$—CHF—CH$_2$—OCO-(L)q'-W, SO$_3^-$—CF$_2$—COO-(L)q'-W, SO$_3^-$—CF$_2$—CF$_2$—CH$_2$—CH$_2$-(L)q-W, or SO$_3^-$—CF$_2$—CH(CF$_3$)—OCO-(L)q'-W is preferable. Here, L, q, and W are each the same as in General Formula (3). q' represents an integer of 0 to 10.

In one aspect, as Z$^-$ in General Formula (ZI), Z$^-$ in General Formula (LU), Z$^-$ in General Formula (ZI-3), Zc$^-$ in General Formula (ZI-3A), and Z$^-$ in General Formula (ZI-4), an anion represented by General Formula (4) is also preferable.

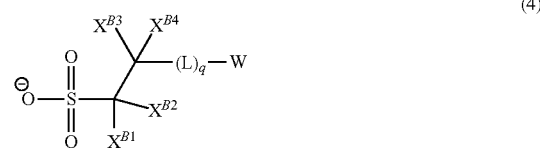

In General Formula (4), $X^{B1}$ and $X^{B2}$ each independently represent a hydrogen atom or a monovalent organic group having no fluorine atom. $X^{B1}$ and $X^{B2}$ are each preferably a hydrogen atom.

$X^{B3}$ and $X^{B4}$ each independently represent a hydrogen atom or a monovalent organic group. It is preferable that at least one of $X^{B3}$ or $X^{B4}$ is a fluorine atom or a monovalent organic group having a fluorine atom, and it is more preferable that both of $X^{B3}$ and $X^{B4}$ are a fluorine atom or a monovalent organic group having a fluorine atom. It is still more preferable that $X^{B3}$ and $X^{B4}$ are both an alkyl group substituted with a fluorine atom.

L, q, and W are the same as in General Formula (3).

Z$^-$ in General Formula (ZI), Z$^-$ in General Formula (ZII), Z$^-$ in General Formula (ZI-3), Zc$^-$ in General Formula (ZI-3A), and Z$^-$ in General Formula (ZI-4) may be a benzenesulfonate anion, and is preferably a benzenesulfonate anion substituted with a branched alkyl group or a cycloalkyl group.

As Z$^-$ in General Formula (ZI), Z$^-$ in General Formula (ZII), Z$^-$ in General Formula (ZI-3), Zc$^-$ in General Formula (ZI-3A), and Z$^-$ in General Formula (ZI-4), an aromatic sulfonate anion represented by General Formula (SA1) is also preferable.

In Formula (SA1),

Ar represents an aryl group and may further have a substituent other than a sulfonate anion and a -(D-B) group. Examples of the substituent that may further be contained include a fluorine atom and a hydroxyl group.

n represents an integer of 0 or more. n is preferably 1 to 4, more preferably 2 or 3, and still more preferably 3.

D represents a single bond or a divalent linking group. Examples of the divalent linking group include an ether group, a thioether group, a carbonyl group, a sulfoxide group, a sulfone group, a sulfonic acid ester group, an ester group, and a group formed by combination of two or more kinds of these groups.

B represents a hydrocarbon group.

It is preferable that D is a single bond and B is an aliphatic hydrocarbon structure. It is more preferable that B is an isopropyl group or a cyclohexyl group.

Preferred examples of the sulfonium cation in General Formula (ZI) and the iodonium cation in General Formula (ZII) are shown below.

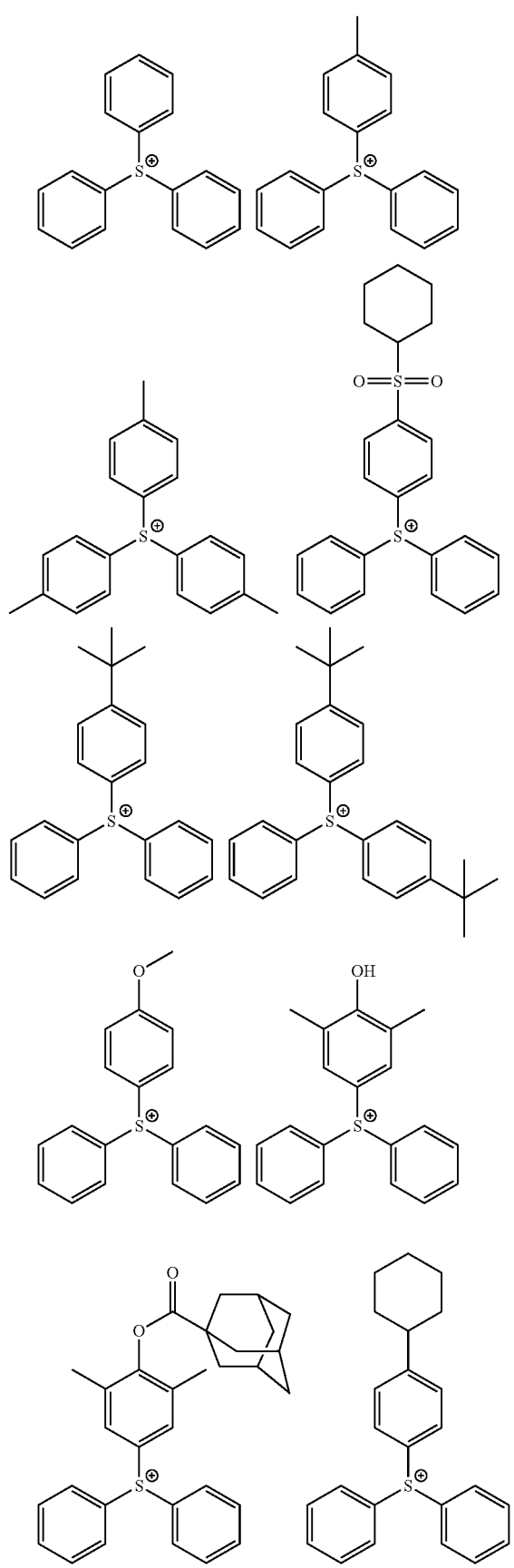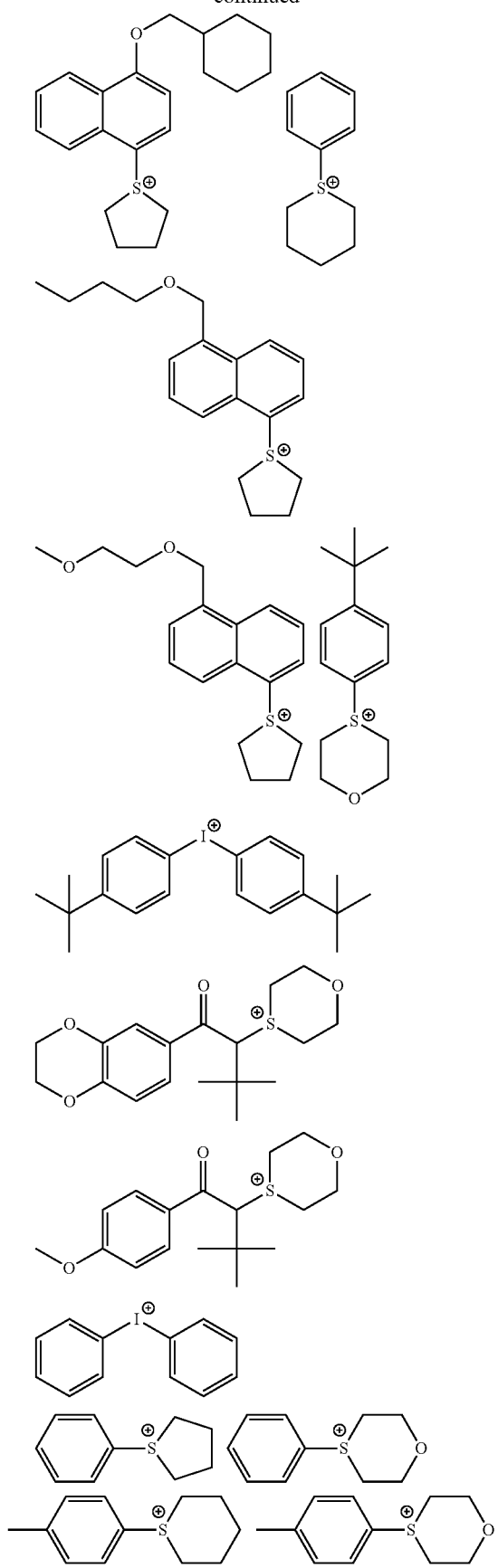

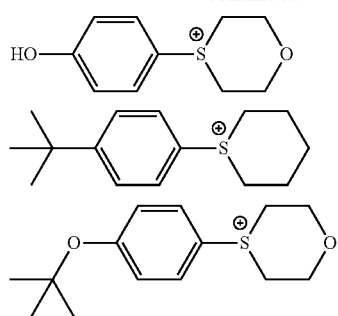
Preferred examples of the anion Z⁻ in General Formula (ZI) and General Formula (ZII), Z⁻ in General Formula (ZI-3), Zc⁻ in General Formula (ZI-3A), and Z⁻ in General Formula (ZI-4) are shown below.
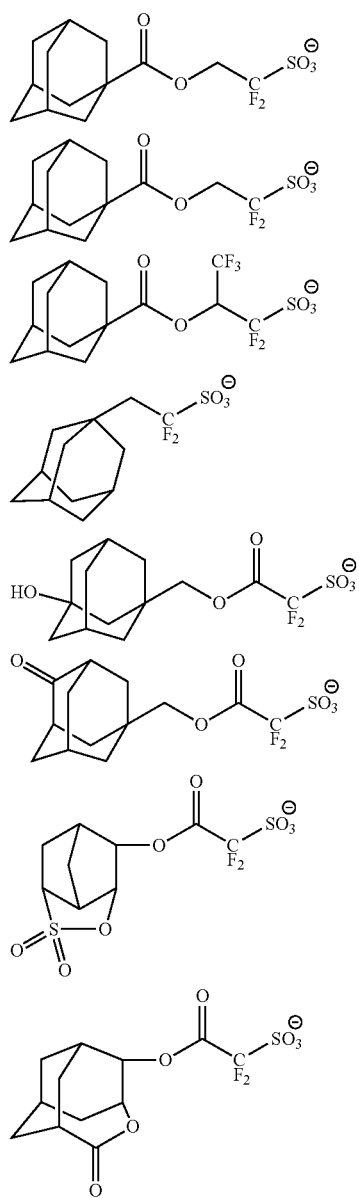
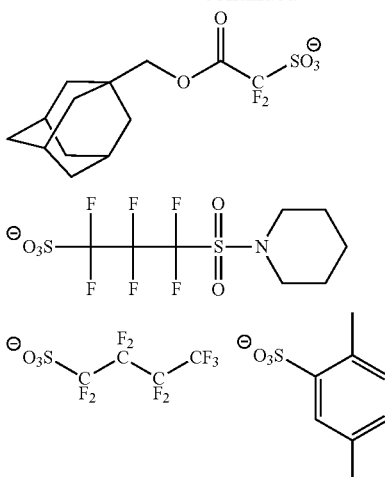

-continued

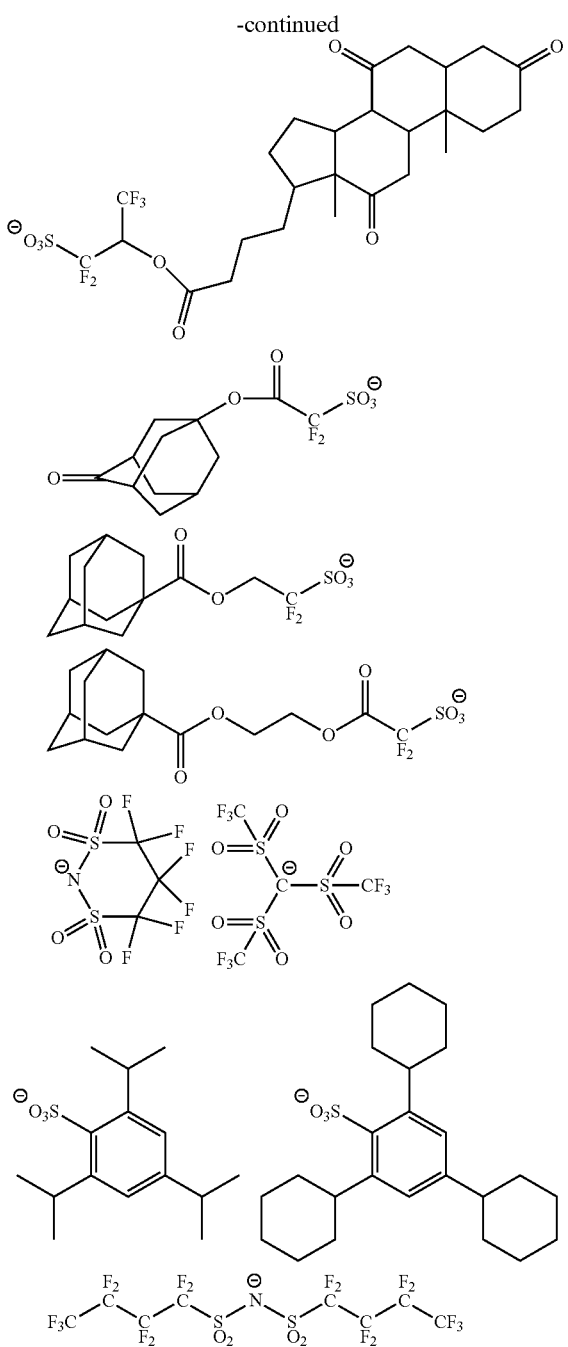

The cation and the anion can be optionally combined and used as a photoacid generator.

The photoacid generator may be in a form of a low-molecular-weight compound or in a form incorporated into a part of a polymer. Further, the form of a low-molecular-weight compound and the form incorporated into a part of a polymer may also be used in combination.

In the present invention, the photoacid generator is preferably in the form of the low-molecular-weight compound.

In a case where the photoacid generator is in the form of the low-molecular-weight compound, the molecular weight is preferably 3,000 or less, more preferably 2,000 or less, and still more preferably 1,000 or less.

In a case where the photoacid generator is in the form incorporated into a part of a polymer, it may be incorporated into the above-mentioned resin (A) or into a resin other than the resin (A).

The photoacid generators may be used singly or in combination of two or more kinds thereof.

The content of the photoacid generator (a total content in a case where a plurality of the photoacid generators are present) in the composition of the embodiment of the present invention is preferably 0.1% to 35% by mass, more preferably 0.5% to 25% by mass, still more preferably 1% to 20% by mass, and particularly preferably 1% to 15% by mass with respect to the total solid contents of the composition.

In a case where the compound represented by General Formula (ZI-3) or (ZI-4) is contained as the photoacid generator, the content of the photoacid generator (a total content in a case where a plurality of the photoacid generators are present) included in the composition is preferably 1% to 35% by mass, and more preferably 1% to 30% by mass, with respect to the total solid contents of the composition.

<Acid Diffusion Control Agent>

The composition of the embodiment of the present invention preferably contains an acid diffusion control agent. The acid diffusion control agent acts as a quencher that suppresses a reaction of the acid-decomposable resin in the unexposed area by excessive generated acids by trapping the acids generated from a photoacid generator or the like upon exposure. For example, a basic compound (DA), a basic compound (DB) whose basicity is reduced or lost upon irradiation with actinic rays or radiation, an onium salt (DC) which becomes a relatively weak acid with respect to an acid generator, a low-molecular-weight compound (DD) which has a nitrogen atom and a group that leaves by the action of an acid, an onium compound (DE) having a nitrogen atom in a cationic moiety, or the like can be used as the acid diffusion control agent. In the composition of the embodiment of the present invention, a known acid diffusion control agent can be appropriately used. For example, the known compounds disclosed in paragraphs [0627] to [0664] of US2016/0070167A1, paragraphs [0095] to [0187] of US2015/0004544A1, paragraphs [0403] to [0423] of US2016/0237190A1, and paragraphs [0259] to [0328] of US2016/0274458A1 can be suitably used as the acid diffusion control agent (D).

As the basic compound (DA), compounds having structures represented by Formulae (A) to (E) are preferable.

(A)

(B)

(C)

(D)

(E)

In General Formulae (A) and (E), $R^{200}$, $R^{201}$, and $R^{202}$ may be the same as or different from each other, and each independently represent a hydrogen atom, an alkyl group (preferably having 1 to 20 carbon atoms), a cycloalkyl group (preferably having 3 to 20 carbon atoms), or an aryl group (having 6 to 20 carbon atoms). $R^{201}$ and $R^{202}$ may be bonded to each other to form a ring.

$R^{203}$, $R^{204}$, $R^{205}$, and $R^{206}$ may be the same as or different from each other, and each independently represent an alkyl group having 1 to 20 carbon atoms.

The alkyl group in each of General Formulae (A) and (E) may have a substituent or may be unsubstituted.

With regard to the alkyl group, the alkyl group having a substituent is preferably an aminoalkyl group having 1 to 20 carbon atoms, a hydroxyalkyl group having 1 to 20 carbon atoms, or a cyanoalkyl group having 1 to 20 carbon atoms.

The alkyl groups in each of General Formulae (A) and (E) are more preferably unsubstituted.

As the basic compound (DA), guanidine, aminopyrrolidine, pyrazole, pyrazoline, piperazine, aminomorpholine, aminoalkylmoipholine, piperidine, or the like is preferable; and a compound having an imidazole structure, a diazabicyclo structure, an onium hydroxide structure, an onium carboxylate structure, a trialkylamine structure, an aniline structure, or a pyridine structure, an alkylamine derivative having a hydroxyl group and/or an ether bond, and an aniline derivative having a hydroxyl group and/or an ether bond, or the like is more preferable.

The basic compound (DB) whose basicity is reduced or lost upon irradiation with actinic rays or radiation (hereinafter also referred to as a "compound (DB)") is a compound which has a proton-accepting functional group, and decomposes under irradiation with actinic rays or radiation to exhibit deterioration in proton-accepting properties, no proton-accepting properties, or a change from the proton-accepting properties to acidic properties.

The proton-accepting functional group refers to a functional group having a group or an electron which is capable of electrostatically interacting with a proton, and for example, means a functional group with a macrocyclic structure, such as a cyclic polyether, or a functional group having a nitrogen atom having an unshared electron pair not contributing to π-conjugation. The nitrogen atom having an unshared electron pair not contributing to π-conjugation is, for example, a nitrogen atom having a partial structure represented by the following formula.

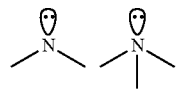

Unshared electron pair

Preferred examples of the partial structure of the proton-accepting functional group include a crown ether structure, an azacrown ether structure, primary to tertiary amine structures, a pyridine structure, an imidazole structure, and a pyrazine structure.

The compound (DB) decomposes upon irradiation with actinic rays or radiation to generate a compound exhibiting deterioration in proton-accepting properties, no proton-accepting properties, or a change from the proton-accepting properties to acidic properties. Here, exhibiting deterioration in proton-accepting properties, no proton-accepting properties, or a change from the proton-accepting properties to acidic properties means a change of proton-accepting properties due to the proton being added to the proton-accepting functional group, and specifically a decrease in the equilibrium constant at chemical equilibrium in a case where a proton adduct is generated from the compound (DB) having the proton-accepting functional group and the proton.

The proton-accepting properties can be confirmed by performing pH measurement.

In the present invention, the acid dissociation constant pKa of the compound generated by the decomposition of the compound (DB) upon irradiation with actinic rays or radiation preferably satisfies pKa<-1, more preferably -13<pKa<-1, and still more preferably -13<pKa<-3.

The acid dissociation constant pKa indicates an acid dissociation constant pKa in an aqueous solution, and is defined, for example, in Chemical Handbook (II) (Revised 4$^{th}$ Edition, 1993, compiled by the Chemical Society of Japan, Maruzen Company, Ltd.). A lower value of the acid dissociation constant pKa indicates higher acid strength. Specifically, the acid dissociation constant pKa in an aqueous solution may be measured by using an infinite-dilution aqueous solution and measuring the acid dissociation constant at 25° C. Alternatively, the acid dissociation constant pKa can also be determined using the following software package 1, by computation from a value based on a Hammett substituent constant and database of publicly known literature values. Any of the values of a pKa described in the present specification represent values determined by calculation using the software package.

Software package 1: Advanced Chemistry Development (ACD/Labs) Software V8.14 for Solaris (1994-2007 ACD/Labs).

In the composition of the embodiment of the present invention, an onium salt (DC) which becomes a relatively weak acid with respect to the photoacid generator can be used as an acid diffusion control agent.

In a case of mixing the photoacid generator and the onium salt capable of generating an acid which is a relatively weak acid with respect to an acid generated from the photoacid generator, and then using the mixture, in a case where the acid generated from the photoacid generator upon irradiation with actinic rays or radiation collides with an onium salt having an unreacted weak acid anion, a weak acid is jetted by salt exchange, thereby generating an onium salt having a strong acid anion. In this process, since the strong acid is exchanged with a weak acid having a lower catalytic ability, the acid is deactivated in appearance, and it is thus possible to perform the control of acid diffusion.

As the onium salt which becomes a relatively weak acid with respect to the photoacid generator, compounds represented by General Formulae (d1-1) to (d1-3) are preferable.

(d1-1)

(d1-2)

(d1-3)

In the formulae, $R^{51}$ is a hydrocarbon group which may have a substituent, $Z^{2c}$ is a hydrocarbon group (provided that carbon adjacent to S is not substituted with a fluorine atom) having 1 to 30 carbon atoms, which may have a substituent, $R^{52}$ is an organic group, $Y^3$ is a linear, branched, or cyclic alkylene group or arylene group, Rf is a hydrocarbon group including a fluorine atom, and $M^+$'s are each independently an ammonium cation, a sulfonium cation, or an iodonium cation.

Preferred examples of the sulfonium cation or the iodonium cation represented by $M^+$ include the sulfonium cations exemplified for General Formula (ZI) and the iodonium cations exemplified for General Formula (ZII) of the photoacid generator.

The onium salt (DC) which becomes a relatively weak acid with respect to the photoacid generator may be a compound (hereinafter also referred to as a "compound (DCA)") having a cationic moiety and an anionic moiety in the same molecule, in which the cationic moiety and the anionic moiety are linked to each other through a covalent bond.

As the compound (DCA), a compound represented by any one of General Formulae (C-1), . . . , or (C-3) is preferable.

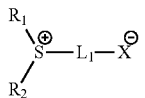
(C-1)

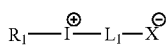
(C-2)

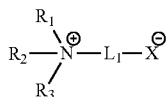
(C-3)

In General Formulae (C-1) to (C-3), $R_1$, $R_2$, and $R_3$ each independently represent a substituent having 1 or more carbon atoms.

$L_1$ represents a divalent linking group that links a cationic moiety with an anionic moiety, or a single bond.

—$X^-$ represents an anionic moiety selected from —COO$^-$, —SO$_3^-$—, —SO$_2^-$, and —N$^-$—R$_4$. R$_4$ represents a monovalent substituent having at least one of a carbonyl group: —C(=O)—, a sulfonyl group: —S(=O)$_2$—, or a sulfinyl group: —S(=O)— at a site for linking to an adjacent N atom.

$R_1$, $R_2$, $R_3$, $R_4$, and $L_1$ may be bonded to one another to form a ring structure. Further, in General Formula (C-3), two of $R_1$ to $R_3$ may be combined to represent a divalent substituent or $R_1$ to $R_3$ may be bonded to an N atom through a double bond.

Examples of the substituent having 1 or more carbon atoms in each of $R_1$ to $R_3$ include an alkyl group, a cycloalkyl group, an aryl group, an alkyloxycarbonyl group, a cycloalkyloxycarbonyl group, an aryloxycarbonyl group, an alkylaminocarbonyl group, a cycloalkylaminocarbonyl group, and an arylaminocarbonyl group. The substituent is preferably an alkyl group, a cycloalkyl group, or an aryl group.

Examples of $L_1$ as a divalent linking group include a linear or branched alkylene group, a cycloalkylene group, an arylene group, a carbonyl group, an ether bond, ester bond, amide bond, a urethane bond, a urea bond, and a group formed by a combination of two or more kinds of these groups. $L_1$ is preferably an alkylene group, an arylene group, an ether bond, ester bond, and a group formed by a combination of two or more kinds of these groups.

The low-molecular-weight compound (DD) (hereinafter referred to as a "compound (DD)") which has a nitrogen atom and a group that leaves by the action of an acid is preferably an amine derivative having a group that leaves by the action of an acid on a nitrogen atom.

As the group that leaves by the action of an acid, an acetal group, a carbonate group, a carbamate group, a tertiary ester group, a tertiary hydroxyl group, or a hemiaminal ether group is preferable, and the carbamate group or the hemiaminal ether group is particularly preferable.

The molecular weight of the compound (DD) is preferably 100 to 1,000, more preferably 100 to 700, and still more preferably 100 to 500.

The compound (DD) may have a carbamate group having a protecting group on a nitrogen atom. The protecting group constituting the carbamate group is represented by General Formula (d-1).

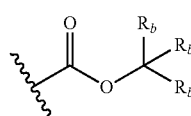
(d-1)

In General Formula (d-1), $R_b$'s each independently represent a hydrogen atom, an alkyl group (preferably having 1 to 10 carbon atoms), a cycloalkyl group (preferably having 3 to 30 carbon atoms), an aryl group (preferably having 3 to 30 carbon atoms), an aralkyl group (preferably having 1 to 10 carbon atoms), or an alkoxyalkyl group (preferably having 1 to 10 carbon atoms). $R_b$'s may be bonded to each other to form a ring.

The alkyl group, the cycloalkyl group, the aryl group, and the aralkyl group represented by Rb may be each independently substituted with a functional group such as a hydroxyl group, a cyano group, an amino group, a pyrrolidino group, a piperidino group, a morpholino group, and an oxo group, an alkoxy group, or a halogen atom. This shall apply to the alkoxyalkyl group represented by $R_b$.

As $R_b$, a linear or branched alkyl group, a cycloalkyl group, or an aryl group is preferable, and the linear or branched alkyl group or the cycloalkyl group is more preferable.

Examples of the ring formed by the mutual linking of two $R_b$'s include an alicyclic hydrocarbon group, an aromatic hydrocarbon group, a heterocyclic hydrocarbon, and derivatives thereof.

Examples of the specific structure of the group represented by General Formula (d-1) include, but are not limited to, the structures disclosed in paragraph [0466] in US2012/0135348A1.

It is preferable that the compound (DD) has a structure represented by General Formula (6).

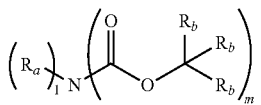
(6)

In General Formula (6), l represents an integer of 0 to 2, and m represents an integer of 1 to 3, satisfying l+m=3.

$R_a$ represents a hydrogen atom, an alkyl group, a cycloalkyl group, an aryl group, or an aralkyl group. In a case where l is 2, two $R_a$'s may be the same as or different from each other, and two $R_a$'s may be linked to each other to form a heterocycle, together with the nitrogen atom in the formula. The heterocycle may include a heteroatom other than the nitrogen atom in the formula.

$R_b$ has the same meaning as $R_b$ in General Formula (d-1), and preferred examples are also the same.

In General Formula (6), the alkyl group, the cycloalkyl group, the aryl group, and the aralkyl group as $R_a$ may be each independently substituted with the same groups as the group mentioned above as a group which may be substituted in the alkyl group, the cycloalkyl group, the aryl group, and the aralkyl group as Rb.

Specific examples of the alkyl group, the cycloalkyl group, the aryl group, and the aralkyl group (these groups may be substituted with the groups as described above) of $R_a$ include the same groups as the specific examples as described above with respect to $R_b$.

Specific examples of the particularly preferred compound (DD) in the present invention include, but are not limited to, the compounds disclosed in paragraph [0475] in US2012/0135348A1.

The onium salt compound (DE) (hereinafter also referred to as a "compound (DE)") having a nitrogen atom in a cation portion is preferably a compound having a basic moiety including a nitrogen atom in a cation portion. The basic moiety is preferably an amino group, and more preferably an aliphatic amino group. It is more preferable that all of the atoms adjacent to the nitrogen atom in the basic moiety are hydrogen atoms or carbon atoms. Further, from the viewpoint of improvement of basicity, it is preferable that an electron-withdrawing functional group (a carbonyl group, a sulfonyl group, a cyano group, a halogen atom, and the like) is not directly linked to the nitrogen atom.

Specific preferred examples of the compound (DE) include, but are not limited to, the compounds disclosed in paragraph [0203] of US2015/0309408A1.

Preferred examples of the acid diffusion control agent are shown below.

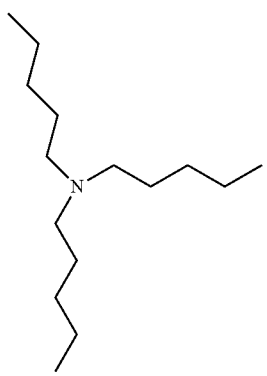

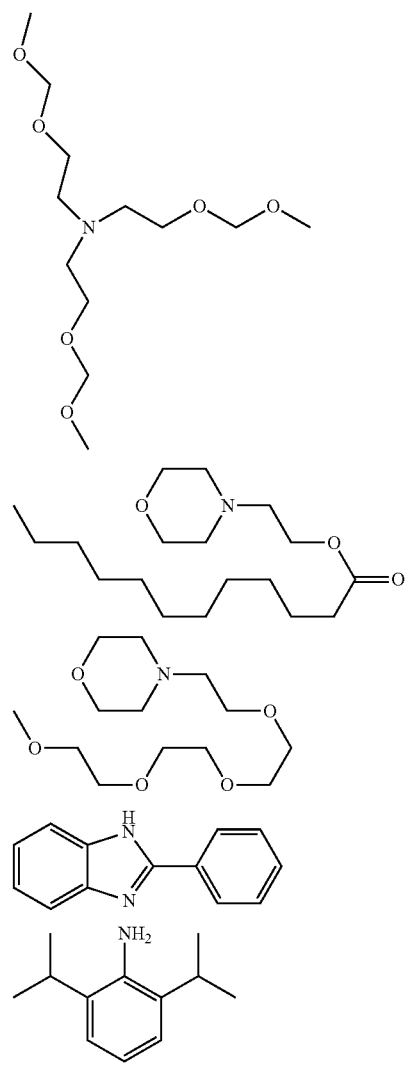

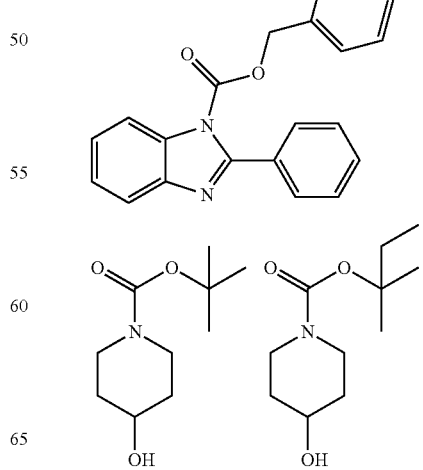

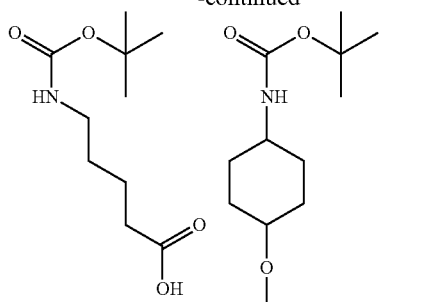
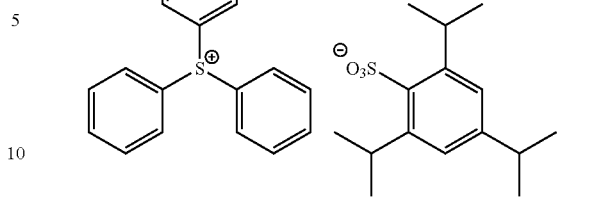
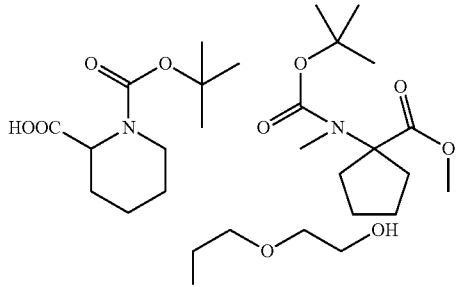
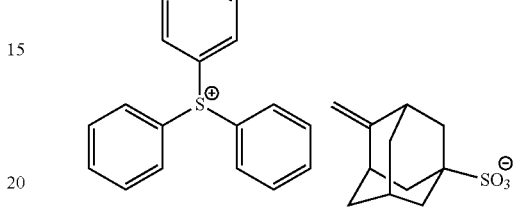
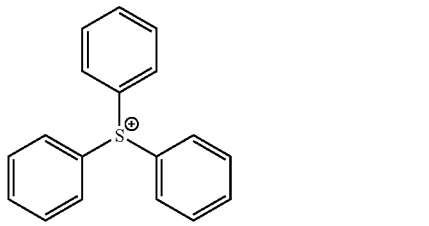
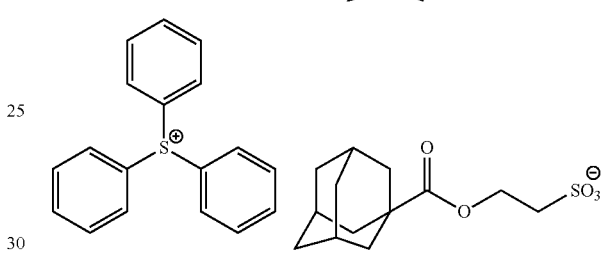
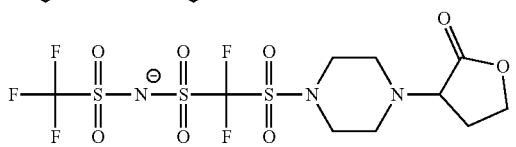
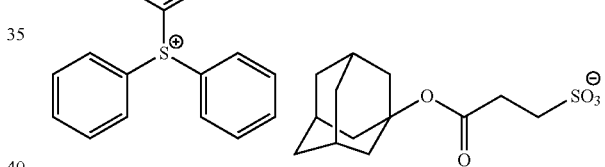
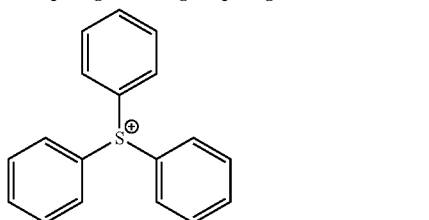
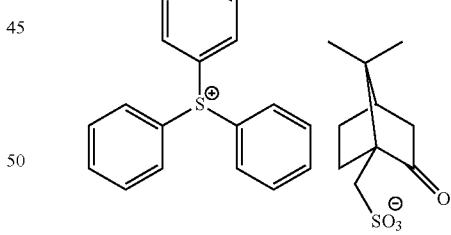
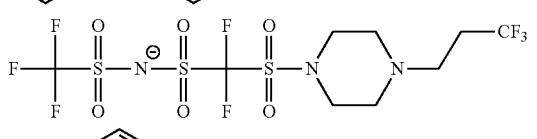
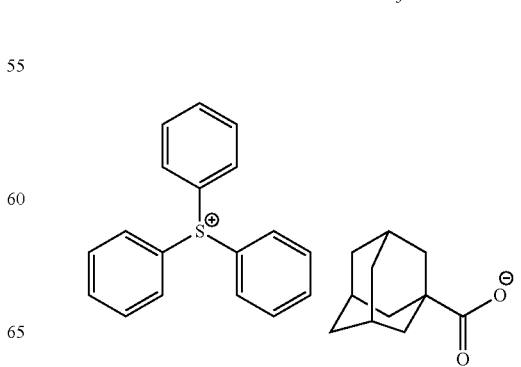

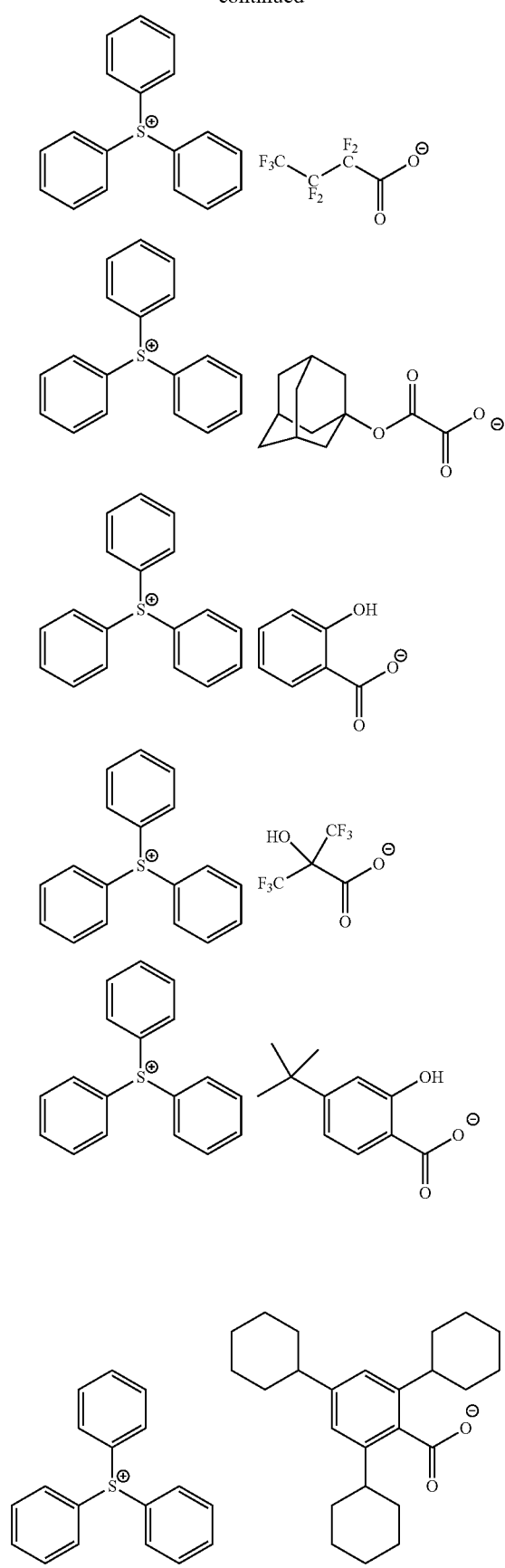
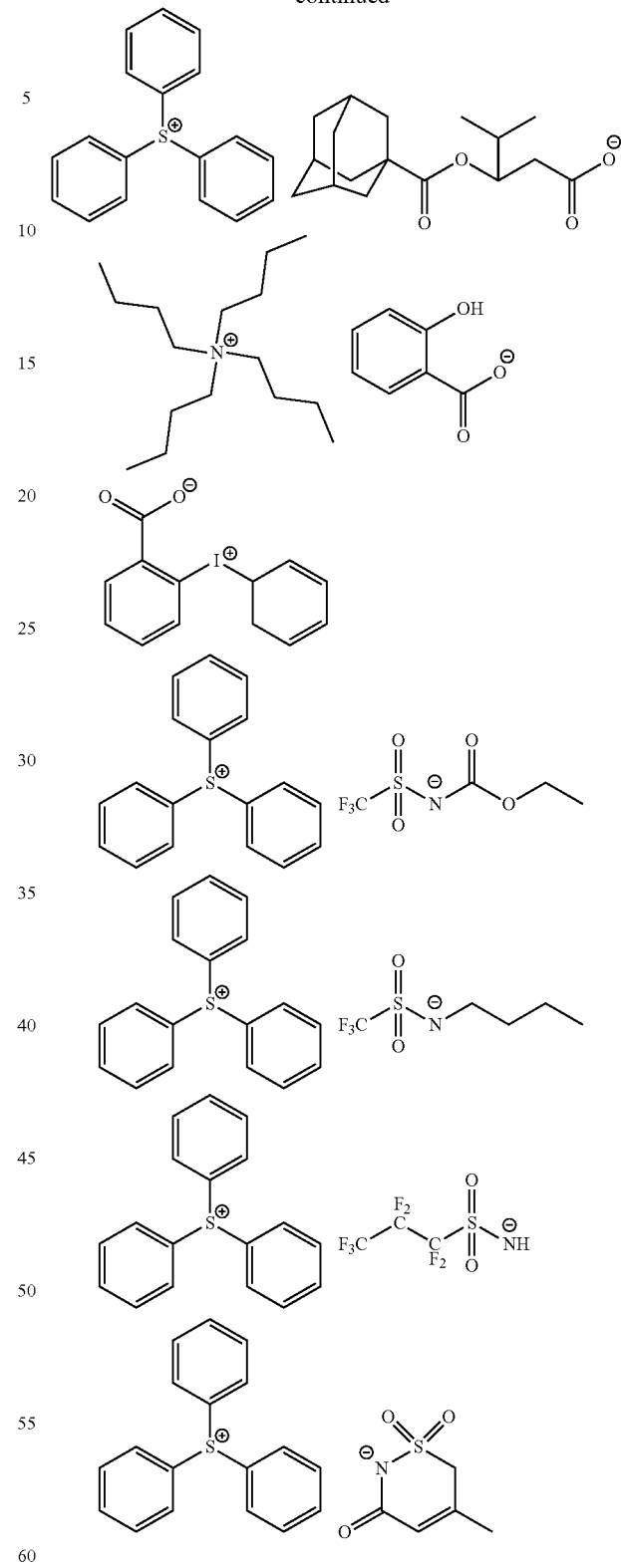
In the composition of the embodiment of the present invention, the acid diffusion control agent (D) may be used singly or in combination of two or more kinds thereof.
The content of the acid diffusion control agent (a total content in a case where a plurality of the acid diffusion control agents are present) in the composition of the embodiment of the present invention is preferably 0.05% to 10% by mass, and more preferably 0.05% to 5% by mass with respect to the total solid content of the composition.

<Hydrophobic Resin>

The composition of the embodiment of the present invention may contain a hydrophobic resin. Further, the hydrophobic resin is preferably a resin which is different from the resin (A).

By incorporating the hydrophobic resin into the composition of the embodiment of the present invention, it is possible to improve the static/dynamic contact angle at a surface of an actinic ray-sensitive or radiation-sensitive film. Thus, it becomes possible to improve development characteristics, suppress generation of out gas, improve immersion liquid tracking properties upon liquid immersion exposure, and reduce liquid immersion defects, for example.

It is preferable that the hydrophobic resin is designed to be unevenly distributed on a surface of a resist film, but unlike the surfactant, the hydrophobic resin does not necessarily have a hydrophilic group in a molecule thereof and does not necessarily contribute to uniform mixing of polar/non-polar materials.

The hydrophobic resin is preferably a resin having a repeating unit having at least one selected from the group consisting of a "fluorine atom", a "silicon atom", and a "$CH_3$ partial structure which is contained in a side chain portion of a resin" from the viewpoint of uneven distribution on a film surface layer.

In a case where the hydrophobic resin includes a fluorine atom and/or a silicon atom, the fluorine atom and/or the silicon atom described above in the hydrophobic resin may be included in the main chain of a resin or may be included in a side chain.

In a case where the hydrophobic resin includes a fluorine atom, it is preferably a resin which has an alkyl group having a fluorine atom, a cycloalkyl group having a fluorine atom, or an aryl group having a fluorine atom as a partial structure having a fluorine atom.

It is preferable that the hydrophobic resin has at least one group selected from the following group of (x) to (z):

(x) an acid group, (y) a group whose solubility in an alkali developer increases through decomposition by the action of the alkali developer (hereinafter also referred to as a polarity converting group), and (z) a group that decomposes by the action of an acid.

Examples of the acid group (x) include a phenolic hydroxyl group, a carboxylic acid group, a fluorinated alcohol group, a sulfonic acid group, a sulfonamido group, a sulfonylimido group, an (alkylsulfonyl)(alkylcarbonyl)methylene group, an (alkylsulfonyl)(alkylcarbonyl)imido group, a bis(alkylcarbonyl)methylene group, a bis(alkylcarbonyl)imido group, a bis(alkylsulfonyl)methylene group, a bis(alkylsulfonyl)imido group, a tris(alkylcarbonyl)methylene group, and a tris(alkylsulfonyl)methylene group.

As the acid group, a fluorinated alcohol group (preferably hexafluoroisopropanol group), a sulfonimido group, or a bis(alkylcarbonyl)methylene group is preferable.

Examples of the group (y) whose solubility in an alkali developer increases through decomposition by the action of the alkali developer include a lactone group, a carboxylic acid ester group (—COO—), an acid anhydride group (—C(O)OC(O)—), an acid imido group (—NHCONH—), a carboxylic acid thioester group (—COS—), a carbonate ester group (—OC(O)O—), a sulfuric acid ester group (—OSO$_2$O—), and a sulfonic acid ester group (—SO$_2$O—), and the lactone group or the carboxylic acid ester group (—COO—) is preferable.

Examples of the repeating unit including the group include a repeating unit in which the group is directly bonded to the main chain of a resin, such as a repeating unit with an acrylic acid ester or a methacrylic acid ester. In this repeating unit, the group may be bonded to the main chain of the resin through a linking group. Alternatively, the repeating unit may also be incorporated into a terminal of the resin by using a polymerization initiator or chain transfer agent having the group during polymerization.

Examples of the repeating unit having a lactone group include the same ones as the repeating unit having a lactone structure as described earlier in the section of the resin (A).

The content of the repeating unit (y) whose solubility in an alkali developer increases through decomposition by the action of the alkali developer is preferably 1% to 100% by mole, more preferably 3% to 98% by mole, and still more preferably 5% to 95% by mole, with respect to all the repeating units in the hydrophobic resin (E).

With respect to the hydrophobic resin (E), examples of the repeating unit having a group (z) capable of decomposing by the action of an acid include the same ones as the repeating units having an acid-decomposable group, as mentioned in the resin (A). The repeating unit having a group (z) capable of decomposing by the action of an acid may have at least one of a fluorine atom or a silicon atom. The content of the repeating units having a group (z) capable of decomposing by the action of an acid is preferably 1% to 80% by mole, more preferably 10% to 80% by mole, and still more preferably 20% to 60% by mole, with respect to all the repeating units in the hydrophobic resin (E).

The hydrophobic resin (E) may have a repeating unit which is different from the above-mentioned repeating units.

The content of the repeating units including a fluorine atom is preferably 10% to 100% by mole, and more preferably 30% to 100% by mole, with respect to all the repeating units in the hydrophobic resin (E). Further, the content of the repeating units including a silicon atom is preferably 10% to 100% by mole, and more preferably 20% to 100% by mole, with respect to all the repeating units in the hydrophobic resin (E).

On the other hand, in a case where the hydrophobic resin (E) includes a $CH_3$ partial structure in the side chain moiety thereof, it is also preferable that the hydrophobic resin (E) has a form not having substantially any one of a fluorine atom and a silicon atom. Further, it is preferable that the hydrophobic resin (E) is substantially constituted with only repeating units, which are composed of only atoms selected from a carbon atom, an oxygen atom, a hydrogen atom, a nitrogen atom, and a sulfur atom.

The weight-average molecular weight of the hydrophobic resin (E) in terms of standard polystyrene is preferably 1,000 to 100,000, and more preferably 1,000 to 50,000.

The total content of residual monomers and/or oligomer components included in the hydrophobic resin (E) is preferably 0.01% to 5% by mass, and more preferably 0.01% to 3% by mass. Further, the dispersity (Mw/Mn) is preferably in the range of 1 to 5, and more preferably in the range of 1 to 3.

As the hydrophobic resin (E), known resins can be appropriately selected and used singly or as a mixture. For example, the known resins disclosed in paragraphs [0451] to [0704] of US2015/0168830A1 and paragraphs [0340] to [0356] of US2016/0274458A1 can be suitably used as the hydrophobic resin (E). Further, the repeating units disclosed in paragraphs [0177] to [0258] of US2016/0237190A1 are also preferable as a repeating unit constituting the hydrophobic resin (E).
Preferred examples of a monomer corresponding to the repeating unit constituting the hydrophobic resin (E) are shown below.
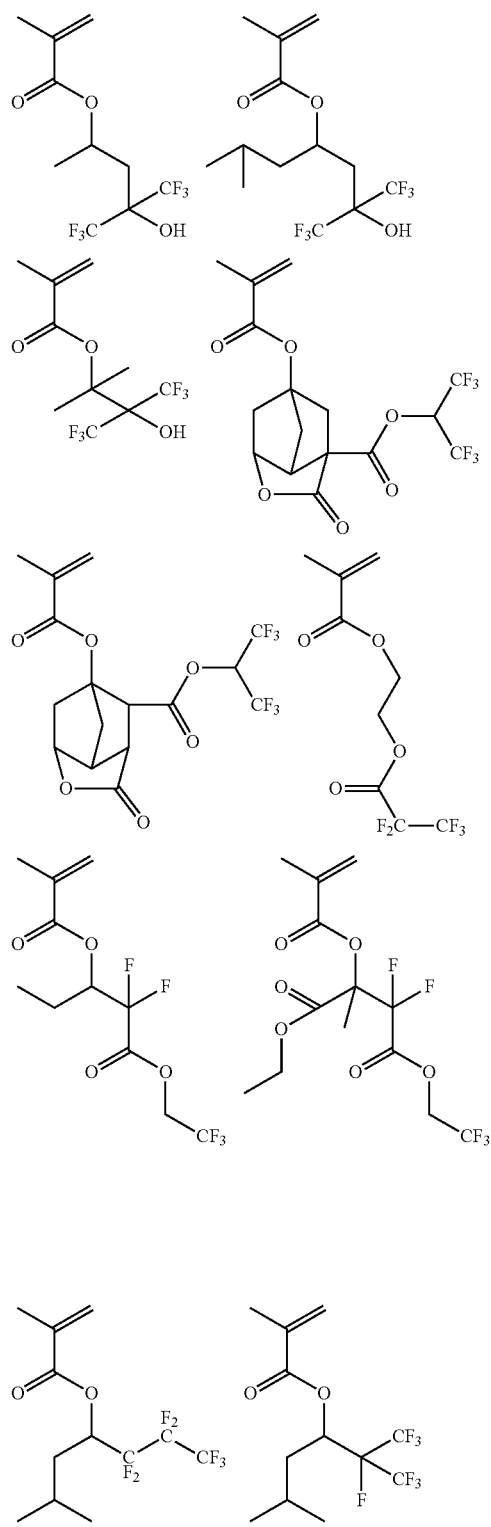
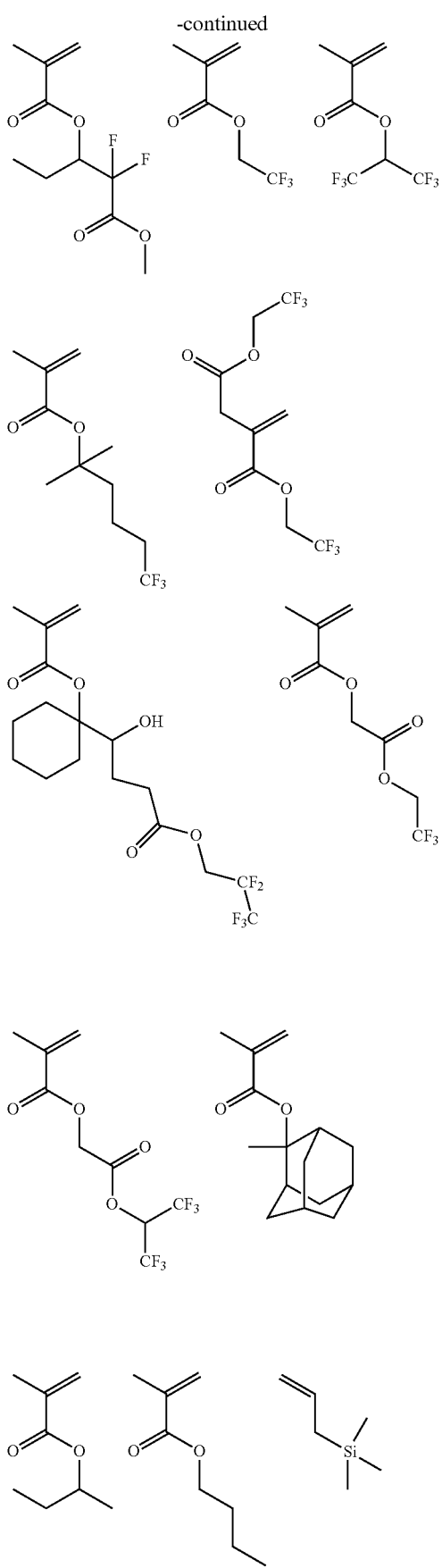

-continued

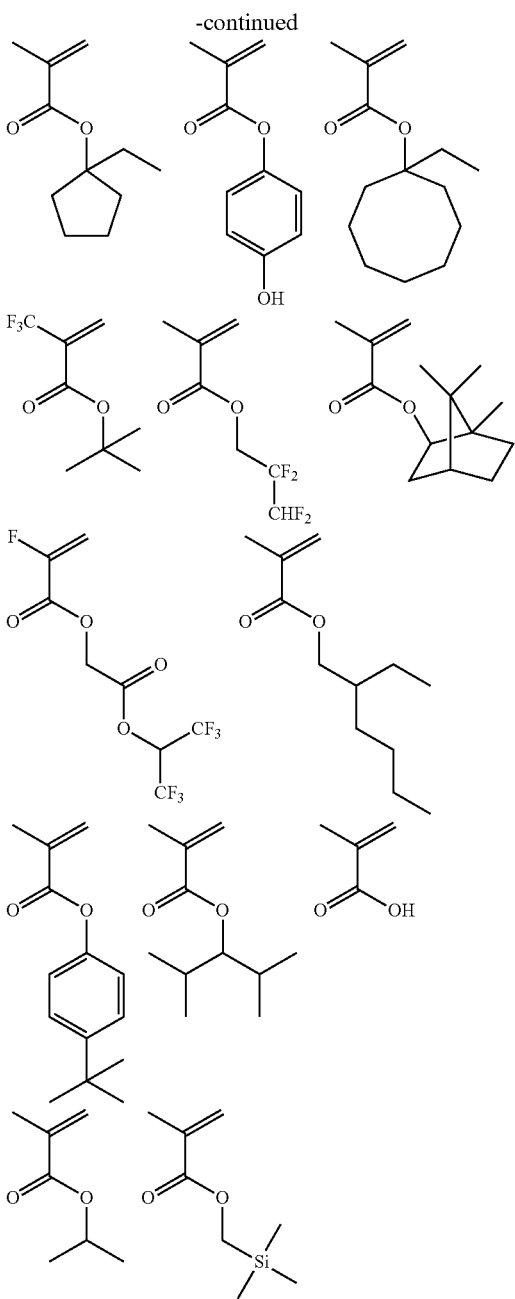

The hydrophobic resin (E) may be used singly or in combination of two or more kinds thereof.

It is preferable to use a mixture of two or more kinds of hydrophobic resins (E) having different levels of surface energy from the viewpoint of satisfying both the immersion liquid tracking properties and the development characteristics upon liquid immersion exposure.

The content of the hydrophobic resin (E) in the composition is preferably 0.01% to 10% by mass, and more preferably 0.05% to 8% by mass with respect to the total solid content in the composition of the embodiment of the present invention.

<Solvent (F)>

The composition of the embodiment of the present invention preferably contains a solvent.

In the composition of the embodiment of the present invention, a known resist solvent can be appropriately used.

For example, the known solvents disclosed in paragraphs [0665] to [0670] of US2016/0070167A1, paragraphs [0210] to [0235] of US2015/0004544A1, paragraphs [0424] to [0426] of US2016/0237190A1, and paragraphs [0357] to [0366] of US2016/0274458A1 can be suitably used.

Examples of the solvent which can be used in the preparation of the composition include organic solvents such as alkylene glycol monoalkyl ether carboxylate, alkylene glycol monoalkyl ether, alkyl lactate ester, alkyl alkoxypropionate, a cyclic lactone (preferably having 4 to 10 carbon atoms), a monoketone compound (preferably having 4 to 10 carbon atoms) which may have a ring, alkylene carbonate, alkyl alkoxyacetate, and alkyl pyruvate.

A mixed solvent obtained by mixing a solvent having a hydroxyl group in the structure and a solvent having no hydroxyl group in the structure may be used as the organic solvent.

As the solvent having a hydroxyl group and the solvent having no hydroxyl group, the above-mentioned exemplary compounds can be appropriately selected, but as the solvent including a hydroxyl group, an alkylene glycol monoalkyl ether, alkyl lactate, or the like is preferable, and propylene glycol monomethyl ether (PGME), propylene glycol monoethyl ether (PGEE), methyl 2-hydroxyisobutyrate, or ethyl lactate is more preferable. Further, as the solvent having no hydroxyl group, an alkylene glycol monoalkyl ether acetate, alkyl alkoxy propionate, a monoketone compound which may have a ring, cyclic lactone, alkyl acetate, or the like is preferable; among these, propylene glycol monomethyl ether acetate (PGMEA), ethyl ethoxypropionate, 2-heptanone, γ-butyrolactone, cyclohexanone, cyclopentanone, or butyl acetate is more preferable; and propylene glycol monomethyl ether acetate, γ-butyrolactone, ethyl ethoxypropionate, cyclohexanone, cyclopentanone, or 2-heptanone is still more preferable. As the solvent having no hydroxyl group propylene carbonate is also preferable.

The mixing ratio (mass ratio) of the solvent having a hydroxyl group to the solvent having no hydroxyl group is 1/99 to 99/1, preferably 10/90 to 90/10, and more preferably 20/80 to 60/40. A mixed solvent containing 50% by mass or more of the solvent having no hydroxyl group is preferable from the viewpoint of coating evenness.

The solvent preferably contains propylene glycol monomethyl ether acetate, and may be a single solvent formed of propylene glycol monomethyl ether acetate or a mixed solvent of two or more kinds of solvents containing propylene glycol monomethyl ether acetate.

<Crosslinking Agent (G)>

The composition of the embodiment of the present invention may contain a compound capable of crosslinking a resin by the action of an acid (hereinafter also referred to as a crosslinking agent (G)). As the crosslinking agent (G), a known compound can be appropriately used. For example, the known compounds disclosed in paragraphs [0379] to [0431] of US2016/0147154A1 and paragraphs [0064] to [0141] of US2016/0282720A1 can be suitably used as the crosslinking agent (G).

The crosslinking agent (G) is a compound having a crosslinkable group which can crosslink a resin, and examples of the crosslinkable group include a hydroxymethyl group, an alkoxymethyl group, an acyloxymethyl group, an alkoxymethyl ether group, an oxirane ring, and an oxetane ring.

The crosslinkable group is preferably a hydroxymethyl group, an alkoxymethyl group, an oxirane ring, or an oxetane ring.

The crosslinking agent (G) is preferably a compound (which also includes a resin) having two or more crosslinkable groups.

The crosslinking agent (G) is preferably a phenol derivative, a urea-based compound (compound having a urea structure), or a melamine-based compound (compound having a melamine structure), which has a hydroxymethyl group or an alkoxymethyl group.

The crosslinking agent may be used singly or in combination of two or more kinds thereof.

The content of the crosslinking agent (G) is preferably 1% to 50% by mass, more preferably 3% to 40% by mass, and still more preferably 5% to 30% by mass, with respect to the total solid content of the resist composition.

<Surfactant (H)>

The composition of the embodiment of the present invention preferably contains a surfactant. In a case where the composition contains the surfactant, a fluorine-based and/or silicon-based surfactant (specifically a fluorine-based surfactant, a silicon-based surfactant, or a surfactant having both of a fluorine atom and a silicon atom) is preferable.

By incorporating the surfactant into the composition of the embodiment of the present invention, it becomes possible to form a pattern which has excellent adhesiveness and decreased development defects with good sensitivity and resolution in a case of using an exposure light source of 250 nm or less, and particularly 220 nm or less.

Examples of the fluorine-based and/or silicon-based surfactant include the surfactants described in paragraph [0276] of US2008/0248425A.

In addition, another surfactant other than the fluorine-based and/or silicon-based surfactant, described in paragraph [0280] of US2008/0248425A can also be used.

These surfactants may be used singly or in combination of two or more kinds thereof.

In a case where the composition of the embodiment of the present invention contains a surfactant, the content of the surfactant is preferably 0.0001% to 2% by mass, and more preferably 0.0005% to 1% by mass with respect to the total solid content of the composition.

On the other hand, by setting the amount of the surfactant to 10 ppm or more with respect to the total solid content of the composition, the hydrophobic resin (E) is further unevenly distributed on the surface. Thus, a surface of the actinic ray-sensitive or radiation-sensitive film can be made more hydrophobic, which can enhance water tracking properties upon liquid immersion exposure.

(Other Additives)

The composition of the embodiment of the present invention may further contain an acid proliferation agent, a dye, a plasticizer, a light sensitizer, a light absorber, an alkali-soluble resin, a dissolution inhibitor, a dissolution promoter, or the like.

Examples of the plasticizer include polyalkylene glycol (the number of carbon atoms in the oxyalkylene unit is preferably 2 to 6, and more preferably 2 or 3, and the average addition number is preferably 2 to 10, and more preferably 2 to 6). Specific examples of the plasticizer include the following ones.

F-1
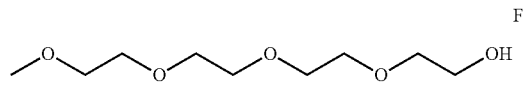

-continued

F-2
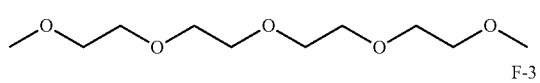

F-3
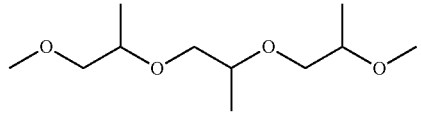

F-4
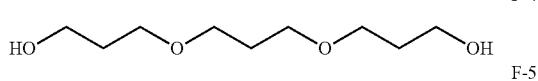

F-5
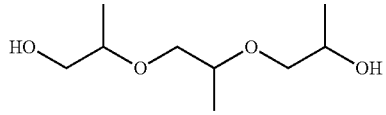

These plasticizers may be used singly or in combination of two or more kinds thereof.

In a case where the composition of the embodiment of the present invention contains a plasticizer, the content of the plasticizer is preferably 0.01% to 20% by mass, and more preferably 1% to 15% by mass with respect to the total solid content of the composition.

<Preparation Method>

The concentration of the solid content of the composition of the embodiment of the present invention is preferably 10% by mass or more, and typically, an upper limit thereof is preferably approximately 50% by mass. Among those, the concentration of the solid content of the composition of the embodiment of the present invention is preferably 10% to 50% by mass, more preferably 25% to 50% by mass, and still more preferably 30% to 50% by mass. The concentration of the solid content of the composition of the embodiment of the present invention is a mass percentage of the mass of other resist components excluding the solvent with respect to the total mass of the composition.

In addition, the film thickness of the actinic ray-sensitive or radiation-sensitive film formed of the composition of the embodiment of the present invention is 2 μm or more, and for the purposes of increasing the number of processing stages, improving ion implantation resistance, and the like, the film thickness is preferably 3 μm or more, more preferably 4 μm or more, and still more preferably 5 μm or more. An upper limit thereof is not particularly limited, and is, for example, 100 μm or less.

In addition, it is possible to form a pattern from the composition of the embodiment of the present invention, as described later.

The film thickness of a pattern thus formed is 2 μm or more, and for the purposes of increasing the number of processing stages, improving ion implantation resistance, and the like, the film thickness is preferably 3 μm or more, more preferably 4 μm or more, and still more preferably 5 μm or more. An upper limit thereof is not particularly limited, and is, for example, 100 μm or less.

The composition of the embodiment of the present invention is used after being applied onto a predetermined support (substrate) to be used after dissolving the above-mentioned components in a predetermined organic solvent, and preferably the mixed solvent, and filtering using a filter. A pore size of the filter to be used for filtration using the filter is preferably 0.1 pin or less, more preferably 0.05 μm or less, and still more preferably 0.03 μm or less. In addition, in a case where the concentration of the solid content of the composition is high (for example, 25% by mass or more), a pore size of the filter to be used for filtration using the filter is preferably 3 µm or less, more preferably 0.5 µm or less, and still more preferably 0.3 µm or less. This filter is preferably a polytetrafluoroethylene-, polyethylene- or nylon-made filter. In the filtration using a filter, circulating filtration may be performed or the filtration may be performed by connecting plural kinds of filters in series or in parallel, as disclosed in JP2002-062667A, for example. In addition, the composition may be filtered in plural times. Furthermore, the composition may be subjected to a deaeration treatment or the like before or after filtration using the filter.

The viscosity of the composition of the embodiment of the present invention is preferably 100 to 500 mPa·s. The viscosity of the composition of the embodiment of the present invention is more preferably 100 to 300 mPa·s from the viewpoint that the coating property is more excellent.

In addition, the viscosity can be measured by an E type viscometer.

<Applications>

The composition of the embodiment of the present invention relates to an actinic ray-sensitive or radiation-sensitive resin composition whose properties change by undergoing a reaction upon irradiation with actinic rays or radiation. More specifically, the composition of the embodiment of the present invention relates to an actinic ray-sensitive or radiation-sensitive resin composition which can be used in a step of manufacturing a semiconductor such as an integrated circuit (IC), for the manufacture of a circuit board for a liquid crystal, a thermal head, or the like, the manufacture of a mold structure for imprinting, other photofabrication processes, a planographic printing plate, or an acid-curable composition. A pattern formed in the present invention can be used in an etching step, an ion implantation step, a bump electrode forming step, a rewiring forming step, a microelectromechanical system (MEMS), or the like.

[Resist Film]

The present invention further relates to a resist film formed with the actinic ray-sensitive or radiation-sensitive resin composition.

[Pattern Forming Method]

The present invention also relates to a pattern forming method using the actinic ray-sensitive or radiation-sensitive resin composition. Hereinafter, the pattern forming method of the embodiment of the present invention will be described. Further, the actinic ray-sensitive or radiation-sensitive film (resist film) of the present invention will also be described, together with the description of the pattern forming method.

The pattern forming method of the embodiment of the present invention includes:

(i) a step of forming a resist film (actinic ray-sensitive or radiation-sensitive film) on a support using the above-mentioned actinic ray-sensitive or radiation-sensitive resin composition (resist film forming step), (ii) a step of exposing the resist film (irradiating actinic rays or radiation) (exposing step), and (iii) a step of developing the exposed resist film using a developer (developing step).

The pattern forming method of the embodiment of the present invention is not particularly limited as long as it includes the steps (i) to (iii), and may further include the following steps.

In the pattern forming method of the embodiment of the present invention, the exposing method in the exposing step (ii) may be liquid immersion exposure.

The pattern forming method of the embodiment of the present invention preferably includes a prebaking (PB) step (iv) before the exposing step (ii).

The pattern forming method of the embodiment of the present invention preferably includes a post-exposure baking (PEB) step (v) after the exposing step (ii) and before the developing step The pattern forming method of the embodiment of the present invention may include the exposing step (ii) a plurality of times.

The pattern forming method of the embodiment of the present invention may include the prebaking heating step (iv) a plurality of times.

The pattern forming method of the embodiment of the present invention may include the post-exposure baking step (v) a plurality of times.

In the pattern forming method of the embodiment of the present invention, the above-mentioned film forming step (i), exposing step (ii), and developing step (iii) can be performed by a generally known method.

In addition, a resist underlayer film (for example, spin on glass (SOG), spin on carbon (SOC), and an antireflection film) may be formed between the resist film and the support, as desired. As a material constituting the resist underlayer film, known organic or inorganic materials can be appropriately used.

A protective film (topcoat) may be formed on the upper layer of the resist film. As the protective film, a known material can be appropriately used. The compositions for forming a protective film disclosed in, for example, US2007/0178407A, US2008/0085466A, US2007/0275326A, US2016/0299432A, US2013/0244438A, or WO2016/157988A can be suitably used. The composition for forming a protective film preferably contains the above-mentioned acid diffusion control agent.

A protective film may be formed on the upper layer of the resist film containing the above-mentioned hydrophobic resin.

The support is not particularly limited, and a substrate which is generally used in a process for manufacturing a semiconductor such as an IC, and a process for manufacturing a circuit board for a liquid crystal, a thermal head, or the like, and other lithographic processes of photofabrication can be used. Specific examples of the support include an inorganic substrate such as silicon, $SiO_2$, and SiN.

For any of the prebaking step (iv) and the post-exposure baking step (v), the heating temperature is preferably 70° C. to 150° C., more preferably 70° C. to 130° C., still more preferably 80° C. to 130° C., and most preferably 80° C. to 120° C.

For any of the prebaking step (iv) and the post-exposure baking step (v), the heating time is preferably 30 to 300 seconds, more preferably 30 to 180 seconds, and still more preferably 30 to 90 seconds.

Heating may be performed using a means comprised in an exposure device and a development device, or may also be performed using a hot plate or the like.

The light source wavelength used in the exposing step is not particularly limited, and examples thereof include infrared rays, visible light, ultraviolet rays, far ultraviolet rays, extreme ultraviolet rays (EUV), X-rays, and electron beams. Among those, far ultraviolet rays are preferable, whose wavelength is preferably 250 mu or less, more preferably 220 nm or less, and still more preferably 1 to 200 nm. Specific examples thereof include a KrF excimer laser (248 nm), an ArF excimer laser (193 nm), an F2 excimer laser (157 nm), X-rays, EUV (13 nm), and electron beams, the KrF excimer laser, the ArF excimer laser, EUV, or the electron beams are preferable, and the KrF excimer laser is more preferable.

In the developing step (iii), the developer may be either an alkali developer or a developer containing an organic solvent (hereinafter also referred to as an organic developer).

As the alkali developer, a quaternary ammonium salt typified by tetramethylammonium hydroxide is usually used, but in addition to the developer, an aqueous alkali-solution such as an inorganic alkali, primary to tertiary amines, alcohol amine, and cyclic amine can also be used.

In addition, the alkali developer may contain an appropriate amount of alcohols and/or a surfactant. The alkali concentration of the alkali developer is usually 0.1% to 20% by mass. The pH of the alkali developer is usually 10 to 15.

The time for performing development using the alkali developer is usually 10 to 300 seconds.

The alkali concentration, the pH, and the development time using the alkali developer can be appropriately adjusted depending on a pattern formed.

As the organic developer, a developer containing at least one organic solvent selected from the group consisting of a ketone-based solvent, an ester-based solvent, an alcohol-based solvent, an amide-based solvent, an ether-based solvent, and hydrocarbon-based solvents is preferable.

Examples of the ketone-based solvent include 1-octanone, 2-octanone, 1-nonanone, 2-nonanone, acetone, 2-heptanone (methyl amyl ketone), 4-heptanone, 1-hexanone, 2-hexanone, diisobutyl ketone, cyclohexanone, methylcyclohexanone, phenyl acetone, methyl ethyl ketone, methyl isobutyl ketone, acetyl acetone, acetonyl acetone, ionone, diacetonyl alcohol, acetyl carbinol, acetophenone, methyl naphthyl ketone, isophorone, and propylene carbonate.

Examples of the ester-based solvent include methyl acetate, butyl acetate, ethyl acetate, isopropyl acetate, pentyl acetate, isopentyl acetate, amyl acetate, propylene glycol monomethyl ether acetate, ethylene glycol monoethyl ether acetate, diethylene glycol monobutyl ether acetate, diethylene glycol monoethyl ether acetate, ethyl-3-ethoxypropionate, 3-methoxybutyl acetate, 3-methyl-3-methoxybutyl acetate, methyl formate, ethyl formate, butyl formate, propyl formate, ethyl lactate, butyl lactate, propyl lactate, butyl butyrate, methyl 2-hydroxyisobutyrate, isoamyl acetate, isobutyl isobutyrate, and butyl propionate.

As the alcohol-based solvent, the amide-based solvent, the ether-based solvent, and the hydrocarbon-based solvent, the solvents disclosed in paragraphs [0715] to [0718] of US2016/0070167A1 can be used.

A plurality of the solvents may be mixed or the solvent may be used in admixture with a solvent other than those described above or water. The moisture content in the entire developer is preferably less than 50% by mass, more preferably less than 20% by mass, and still more preferably less than 10% by mass, and particularly preferably, moisture is not substantially included.

The content of the organic solvent with respect to the organic developer is preferably 50% to 100% by mass, more preferably 80% to 100% by mass, still more preferably 90% to 100% by mass, and particularly preferably 95% to 100% by mass with respect to the total amount of the developer The organic developer may contain an appropriate amount of a known surfactant, as desired.

The content of the surfactant is usually 0.001% to 5% by mass, preferably 0.005% to 2% by mass, and still more preferably 0.01% to 0.5% by mass with respect to the total amount of the developer.

The organic developer may contain the above-mentioned acid diffusion control agent.

Examples of the developing method include a method in which a substrate is immersed in a tank filled with a developer for a certain period of time (a dip method), a method in which a developer is heaped up onto the surface of a substrate by surface tension, and then left to stand for a certain period of time (a puddle method), a method in which a developer is sprayed on the surface of a substrate (a spray method), and a method in which a developer is continuously jetted onto a substrate spun at a constant rate while scanning a developer jetting nozzle at a constant rate (a dynamic dispense method).

A combination of a step of performing development using an aqueous alkali-solution (an alkali developing step) and a step of performing development using a developer containing an organic solvent (an organic solvent developing step) may be used. Thus, a finer pattern can be formed since a pattern can be formed by keeping only a region with an intermediate exposure intensity from not being dissolved.

It is preferable that after the developing step a step of performing washing using a rinsing liquid (a rinsing step) is included.

As the rinsing liquid used in the rinsing step after the developing step using an alkali developer, for example, pure water can be used. Pure water may contain an appropriate amount of a surfactant. In this case, after the developing step or the rinsing step, a treatment for removing the developer or the rinsing liquid adhering on a pattern by a supercritical fluid may be added. In addition, after the rinsing treatment or the treatment using a supercritical fluid, a heating treatment for removing moisture remaining in the pattern may be performed.

The rinsing liquid used in the rinsing step after the developing step using a developer containing an organic solvent is not particularly limited as long as the rinsing liquid does not dissolve the resist pattern, and a solution containing a common organic solvent can be used. As the rinsing liquid, a rinsing liquid containing at least one organic solvent selected from the group consisting of a hydrocarbon-based solvent, a ketone-based solvent, an ester-based solvent, an alcohol-based solvent, an amide-based solvent, and an ether-based solvent is preferably used.

Specific examples of the hydrocarbon-based solvent, the ketone-based solvent, the ester-based solvent, the alcohol-based solvent, the amide-based solvent, and the ether-based solvent are the same solvents as those described for the developer containing an organic solvent.

As the rinsing liquid used in the rinsing step in this case, a rinsing liquid containing a monohydric alcohol is more preferable.

Here, examples of the monohydric alcohol used in the rinsing step include linear, branched, or cyclic monohydric alcohols. Specific examples thereof include 1-butanol, 2-butanol, 3-methyl-1-butanol, tert-butyl alcohol, 1-pentanol, 2-pentanol, 1-hexanol, 4-methyl-2-pentanol, 1-heptanol, 1-octanol, 2-hexanol, cyclopentanol, 2-heptanol, 2-octanol, 3-hexanol, 3-heptanol, 3-octanol, 4-octanol, and methyl isobutyl carbinol. Examples of the monohydric alcohol having 5 or more carbon atoms include 1-hexanol, 2-hexanol, 4-methyl-2-pentanol, 1-pentanol, 3-methyl-1-butanol, and methyl isobutyl carbinol.

The respective components in plural number may be mixed or the components may be used in admixture with an organic solvent other than the above solvents.

The moisture content in the rinsing liquid is preferably 10% by mass or less, more preferably 5% by mass or less, and still more preferably 3% by mass or less. By setting the moisture content to 10% by mass or less, good development characteristics can be obtained.

The rinsing liquid may contain an appropriate amount of a surfactant.

In the rinsing step, the substrate that has been subjected to development using an organic developer is subjected to a washing treatment using a rinsing liquid containing an organic solvent. A method for the washing treatment method is not particularly limited, but examples thereof include a method in which a rinsing liquid is continuously jetted on a substrate rotated at a constant rate (a rotation application method), a method in which a substrate is immersed in a tank filled with a rinsing liquid for a certain period of time (a dip method), and a method in which a rinsing liquid is sprayed on a substrate surface (a spray method). Among those, it is preferable that a washing treatment is performed using the rotation application method, and a substrate is rotated at a rotation speed of 2,000 to 4,000 revolutions per minute (rpm) after washing, thereby removing the rinsing liquid from the substrate. Furthermore, it is also preferable that the method includes a baking step after the rinsing step (post-baking). The developer and the rinsing liquid remaining between and inside the patterns are removed by the baking step. In the heating step after the rinsing step, the heating temperature is usually 40° C. to 160° C., preferably 70° C. to 120° C., and more preferably 70° C. to 95° C., and typically for 10 seconds to 3 minutes, and preferably for 30 seconds to 90 seconds.

It is preferable that various materials (for example, a resist solvent, a developer, a rinsing liquid, a composition for forming an antireflection film, and a composition for forming a topcoat) used in the actinic ray-sensitive or radiation-sensitive resin composition of the embodiment of the present invention, and the pattern forming method of the embodiment of the present invention do not include impurities such as metal components, isomers, and residual monomers. The content of the impurities included in these materials is preferably 1 ppm or less, more preferably 100 ppt or less, and still more preferably 10 ppt by mass or less, and particularly preferably, the impurities are not substantially included (no higher than a detection limit of a measurement device).

Examples of a method for removing impurities such as metals from the various materials include filtration using a filter. As for the filter pore diameter, the pore size is preferably 10 nm or less, more preferably 5 nm or less, and still more preferably 3 nm or less. As for the materials of a filter, a polytetrafluoroethylene-made filter, a polyethylene-made filter, and a nylon-made filter are preferable. As the filter, a filter which had been washed with an organic solvent in advance may be used. In the step of filtration using a filter, plural kinds of filters connected in series or in parallel may be used. In a case of using the plural kinds of filters, a combination of filters having different pore diameters and/or materials may be used. In addition, various materials may be filtered plural times, and the step of filtering plural times may be a circulatory filtration step. As the filter, a filter having a reduced amount of elutes as disclosed in JP2016-201426A is preferable.

In addition to the filtration using a filter, removal of impurities by an adsorbing material may be performed, or a combination of filtration using a filter and an adsorbing material may be used. As the adsorbing material, known adsorbing materials can be used, and for example, inorganic adsorbing materials such as silica gel and zeolite, and organic adsorbing materials such as activated carbon can be used. Examples of the metal adsorbing agent include those disclosed in JP2016-206500A.

In addition, as a method for reducing the impurities such as metals included in various materials, metal content selects the less material as a raw material constituting the various materials, performing filtering using a filter of the raw material constituting the various materials, equipment the inner and a method such as performing distillation under conditions suppressing as much as possible equal to contamination is lined with TEFLON (registered trademark). Preferred conditions in the filtering using a filter to be performed on the raw material constituting the various materials are similar to the above-mentioned conditions.

In order to prevent impurities from being incorporated, it is preferable that various materials are stored in the container described in US2015/0227049A, JP2015-123351A, or the like.

A method for improving the surface roughness of a pattern may be applied to a pattern formed by the pattern forming method of the embodiment of the present invention. Examples of the method for improving the surface roughness of a pattern include the method of treating a resist pattern by plasma of a hydrogen-containing gas disclosed in US2015/0104957A. In addition, known methods as described in JP2004-235468A, US2010/0020297A, and Proc. of SPIE Vol. 8328 83280N-1 "EUV Resist Curing Technique for LWR Reduction and Etch Selectivity Enhancement" may be applied.

In addition, a pattern formed by the method can be used as a core material (core) of the spacer process disclosed in JP1991-270227A (JP-H03-270227A) and US2013/0209941A, for example.

[Method for Manufacturing Electronic Device]

In addition, the present invention further relates to a method for manufacturing an electronic device, including the above-described pattern forming method. An electronic device manufactured by the method for manufacturing an electronic device of an embodiment of the present invention is suitably mounted on electric or electronic equipment (for example, home electronics, office automation (OA)-related equipment, media-related equipment, optical equipment, and telecommunication equipment).

EXAMPLES

Hereinbelow, the present invention will be described in more detail with reference to Examples. The materials, the amounts of materials used, the proportions, the treatment details, the treatment procedure, or the like shown in the Examples below may be modified if appropriate as long as the modifications do not depart from the spirit of the present invention. Therefore, the scope of the present invention should not be construed as being limited to the Examples shown below.

<Resin>

With regard to the resins used, the structures and contents thereof (molar ratios), the weight-average molecular weights (Mw), and the dispersities (Mw/Mn) of the repeating units are shown.

Moreover, the weight-average molecular weights (Mw) and the dispersities (Mw/Mn) of the resins were measured by means of GPC (carrier: tetrahydrofuran (THF)) (an amount in terms of polystyrene). In addition, the contents of the repeating units were measured by means of $^{13}C$-nuclear magnetic resonance (NMR).

(A-1)
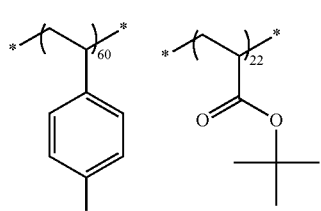
Mw: 18000
Mw/Mn: 1.6
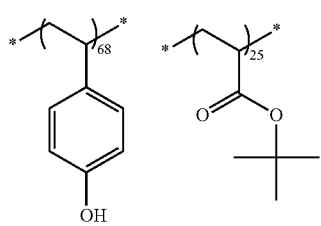
(A-2)
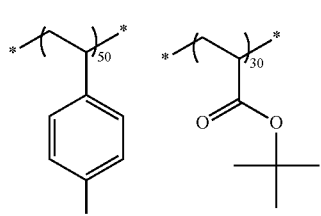
(A-3)
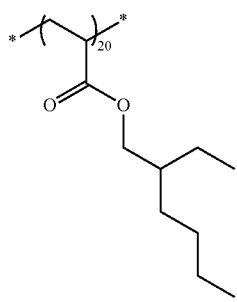
Mw: 24000
Mw/Mn: 1.5
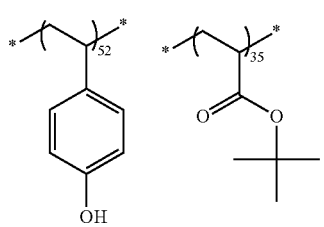
(A-4)
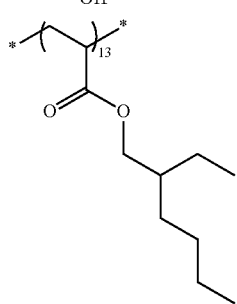
Mw: 16000
Mw/Mn: 1.6
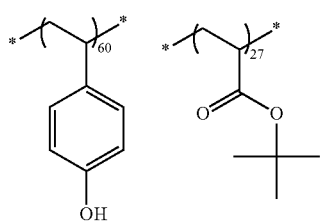
(A-5)
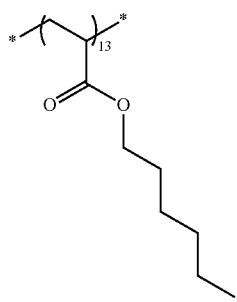
Mw: 18000
Mw/Mn: 1.6

(A-6)
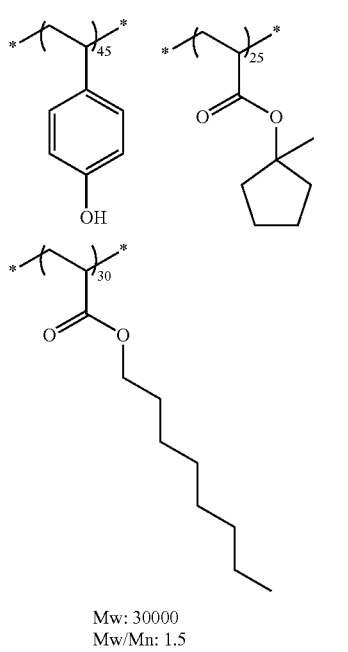
Mw: 30000
Mw/Mn: 1.5
(A-7)
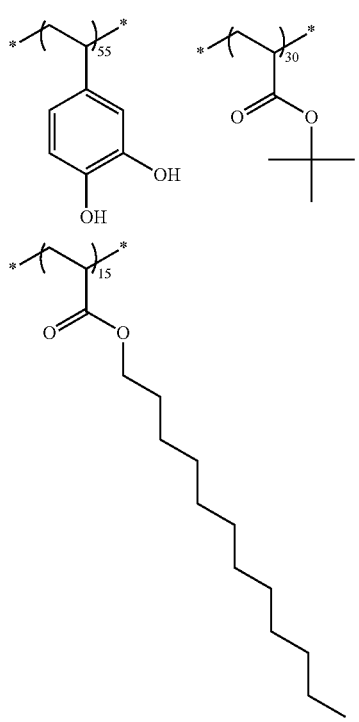
Mw: 30000
Mw/Mn: 1.5
(A-8)
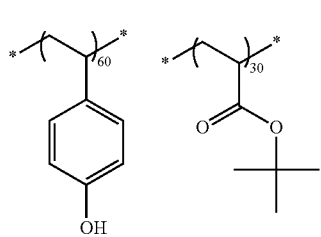
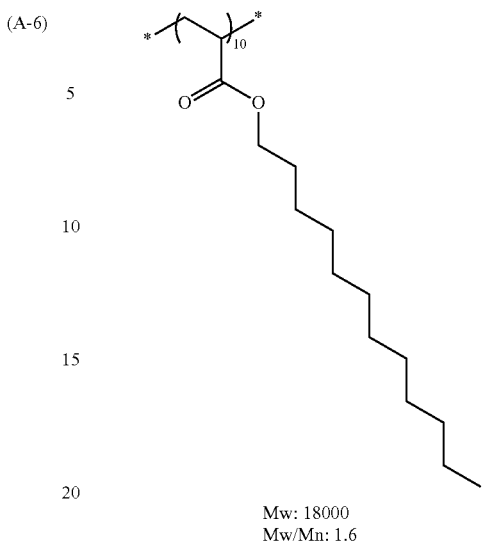
Mw: 18000
Mw/Mn: 1.6
(A-9)
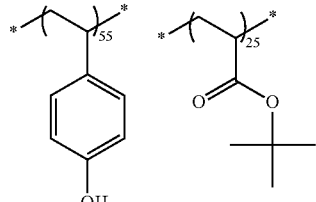
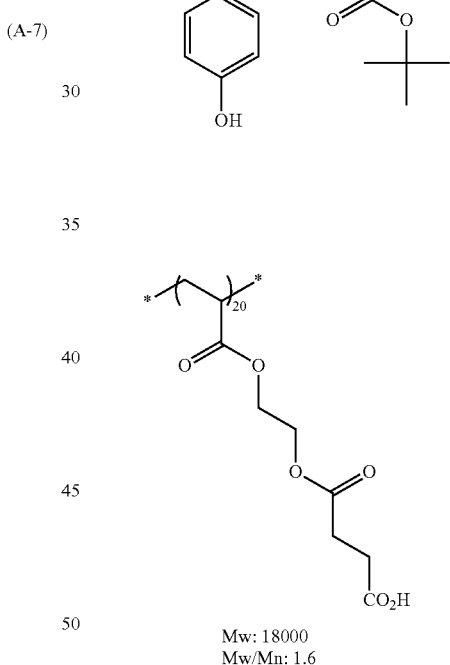
Mw: 18000
Mw/Mn: 1.6
(A-10)
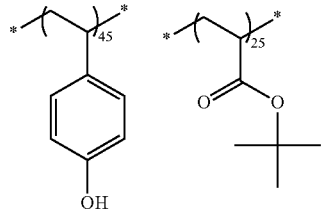

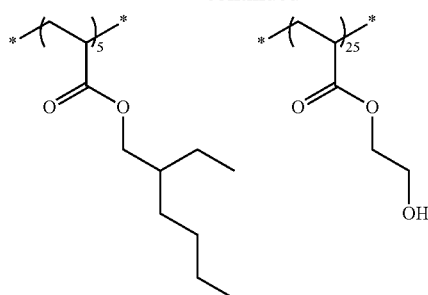
Mw: 19000
Mw/Mn: 1.6
(A-11)
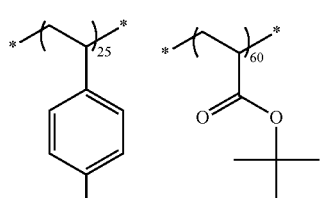
Mw: 19000
Mw/Mn: 1.6
(A-12)
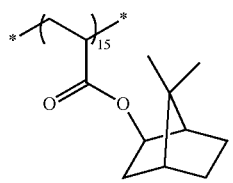
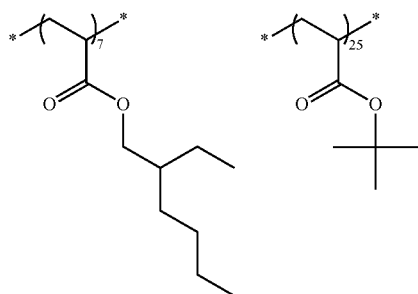
Mw: 19000
Mw/Mn: 1.6
(A-13)
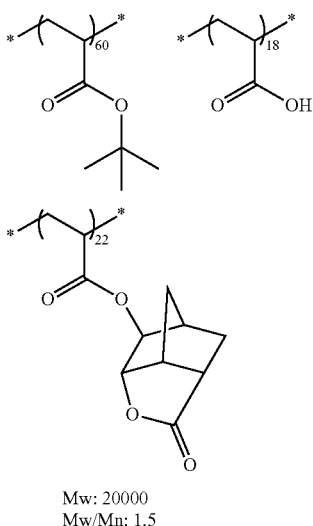
Mw: 20000
Mw/Mn: 1.5
(A-14)
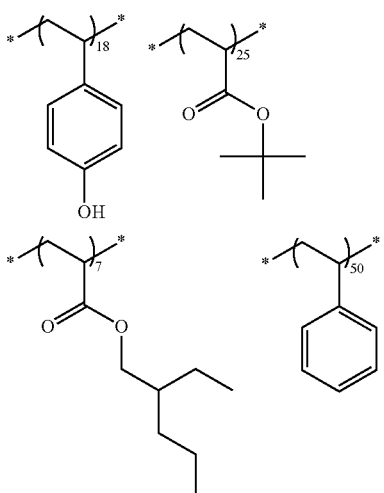
Mw: 18000
Mw/Mn: 1.6
(A-15)
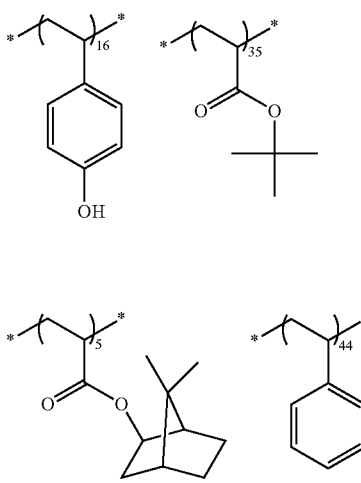
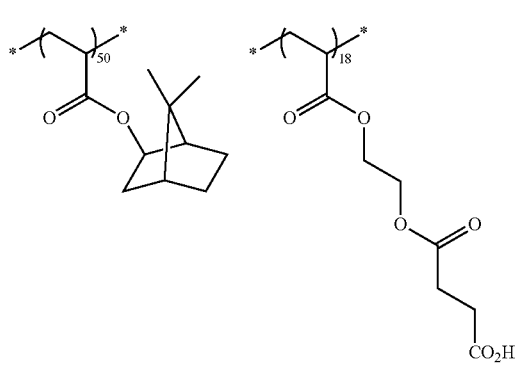
Mw: 18000
Mw/Mn: 1.4

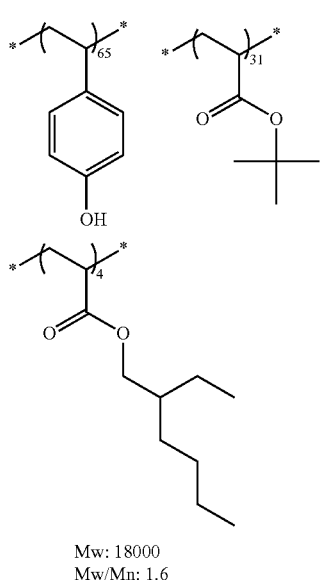
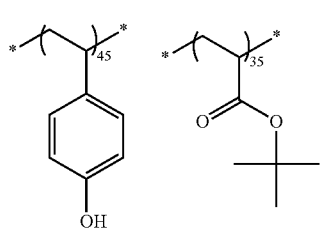
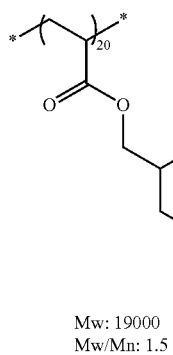
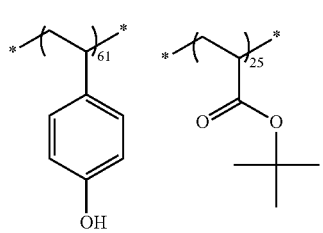
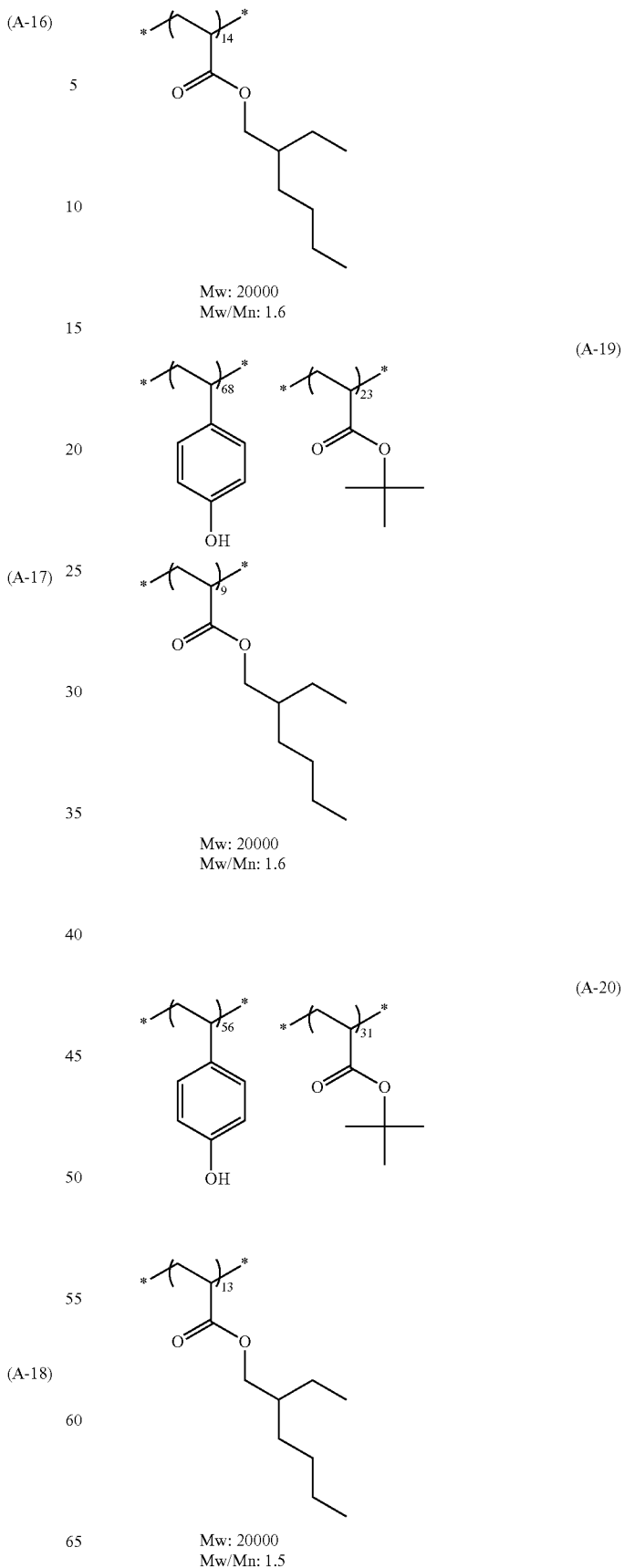

(A-21)
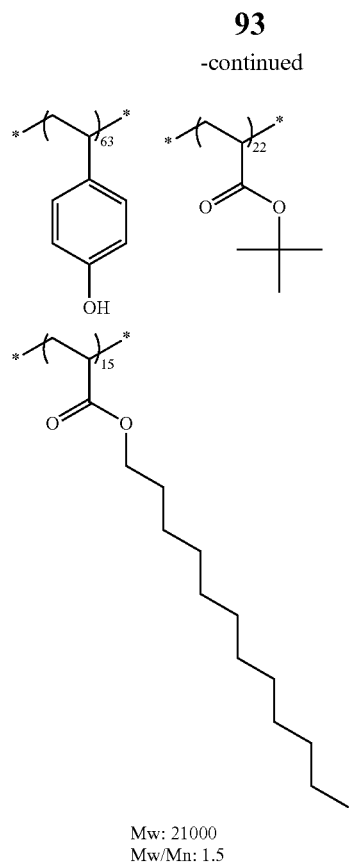
Mw: 21000
Mw/Mn: 1.5
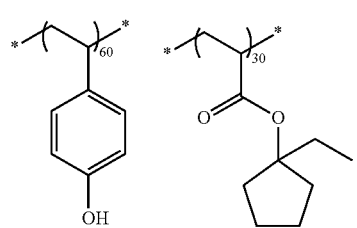
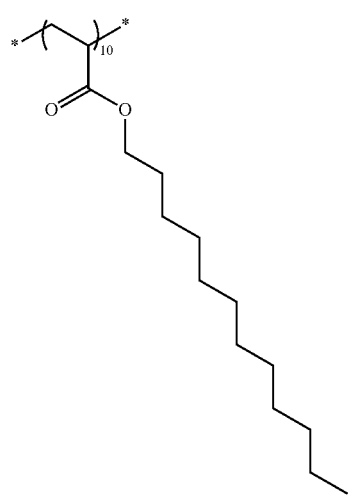
Mw: 13000
Mw/Mn: 1.7
(A-23)
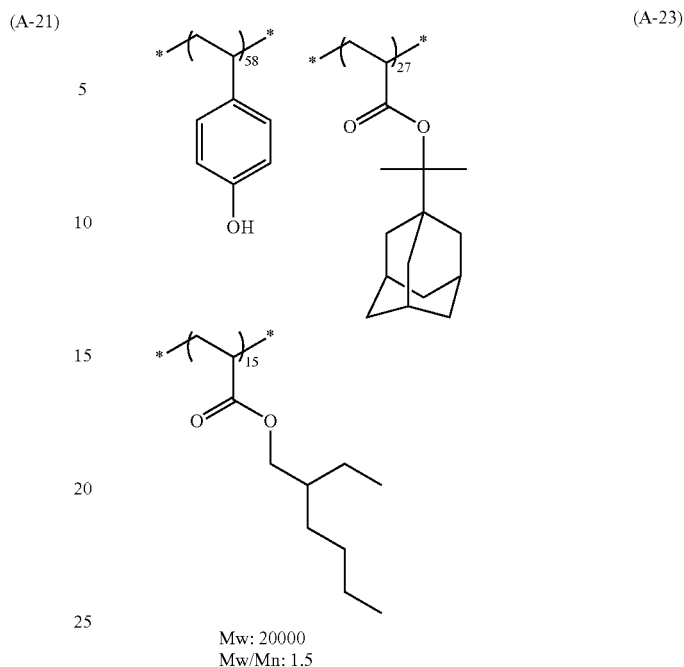
Mw: 20000
Mw/Mn: 1.5
(A-22)
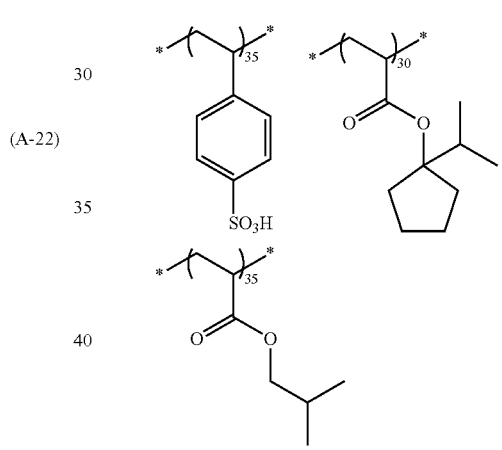
Mw: 12000
Mw/Mn: 1.8
(A-24)
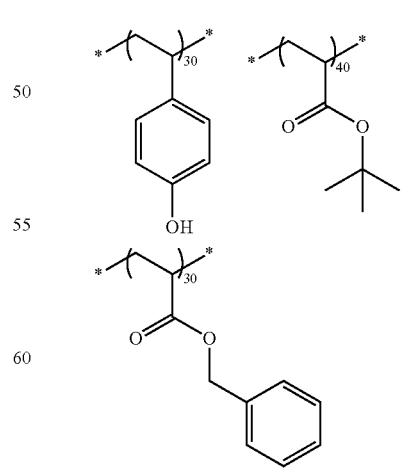
Mw: 25000
Mw/Mn: 1.6
(A-25)

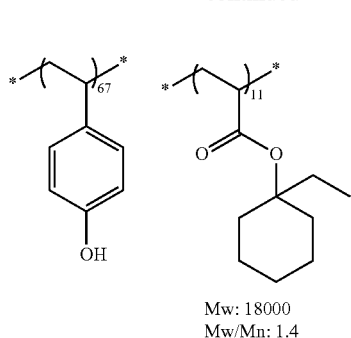
(AX-1)

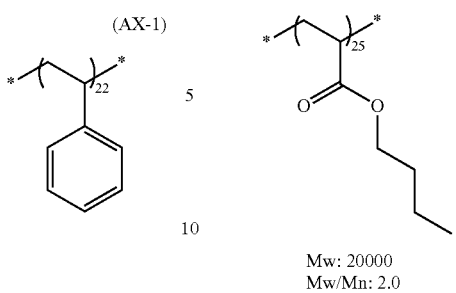

Mw: 20000
Mw/Mn: 2.0

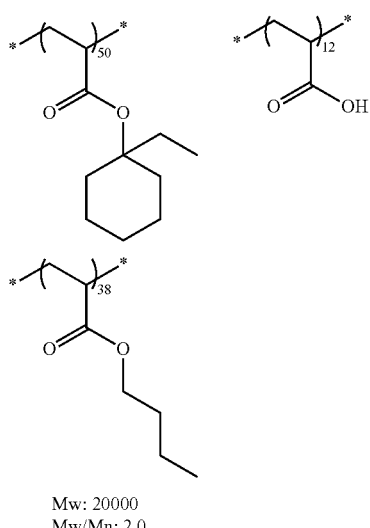
(AX-2)

The glass transition temperatures (Tg) and the Hansen solubility parameters (HSP) of the respective resins are shown in Table 1. Further, among the repeating units included in the respective resins, a repeating unit derived from a monomer allowing a homopolymer formed from the corresponding monomer to have the lowest glass transition temperature (Tg) or a repeating unit having the lowest Hansen solubility parameter (HSP) was defined as a "repeating unit a", and with regard to the repeating unit a of each resin, the values of Tg and HSP of the homopolymer to be formed as above are shown in Table 1.

TABLE 1

| Resin | Resin Tg (° C.) | Resin HSP [(J/cm$^3$)$^{0.5}$] | Repeating unit α Tg (° C.) of homopolymer as formed from the monomer | Repeating unit α HSP [(J/cm$^3$)$^{0.5}$] |
|---|---|---|---|---|
| (A-1) | 126.3 | 19.4 | −10.0 | 16.5 |
| (A-2) | 142.9 | 19.9 | −10.0 | 16.5 |
| (A-3) | 128.3 | 18.7 | −10.0 | 16.5 |
| (A-4) | 123.8 | 19.3 | −54.0 | 17.3 |
| (A-5) | 133.1 | 19.6 | −5.0 | 16.9 |
| (A-6) | 109.5 | 18.6 | −20.0 | 16.3 |
| (A-7) | 108.6 | 20.2 | −65.0 | 15.7 |
| (A-8) | 134.0 | 19.1 | −65.0 | 15.7 |
| (A-9) | 121.5 | 20.7 | 9.0 | 21.9 |
| (A-10) | 113.9 | 20.7 | −10.0 | 16.5 |
| (A-11) | 128.1 | 17.7 | 180.0 | 17.0 |
| (A-12) | 140.2 | 17.9 | −10.0 | 16.5 |
| (A-13) | 141.6 | 18.3 | 238.0 | 20.2 |
| (A-14) | 118.9 | 18.2 | −10.0 | 16.5 |
| (A-15) | 143.4 | 17.9 | 180.0 | 17.0 |
| (A-16) | 142.5 | 19.8 | −10.0 | 16.5 |
| (A-17) | 111.4 | 18.7 | −10.0 | 16.5 |
| (A-18) | 130.4 | 19.5 | −10.0 | 16.5 |
| (A-19) | 141.2 | 20.0 | −10.0 | 16.5 |
| (A-20) | 127.4 | 19.3 | −10.0 | 16.5 |
| (A-21) | 115.7 | 19.3 | −65.0 | 15.7 |
| (A-22) | 133.2 | 19.5 | −23.0 | 16.7 |
| (A-23) | 141.2 | 18.7 | −50.0 | 16.7 |
| (A-24) | 132.3 | 22.3 | 48.0 | 16.5 |
| (A-25) | 128.8 | 18.6 | 54.0 | 18.7 |
| (AX-1) | 165.4 | 20.4 | 110.0 | 18.3 |
| (AX-2) | 98.0 | 17.9 | −54.0 | 17.3 |
| (AX-3) | 147.7 | 19.1 | 54.0 | 18.7 |
| (AX-4) | 112.5 | 19.5 | −54.0 | 17.3 |

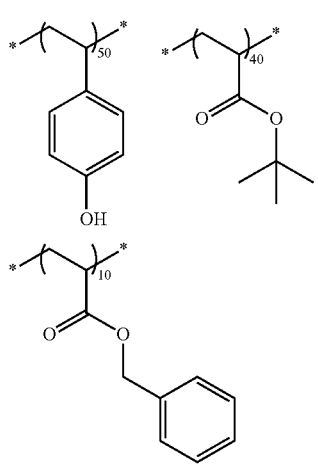
(AX-3)

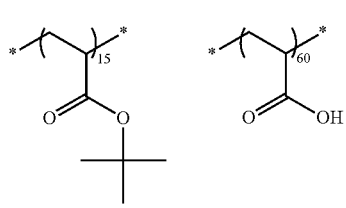
(AX-4)

Furthermore, the "repeating units α" of the respective resins shown Table 1 are shown in Tables 2 to 4 below.

TABLE 2

| Resin | Repeating unit α |
|---|---|
| (A-1), (A-2), (A-3), (A-10), (A-12), (A-14), (A-16), (A-17), (A-18), (A-19), (A-20) | 2-ethylhexyl acrylate structure |
| (A-4), (AX-2), (AX-4) | butyl acrylate structure |
| (A-5) | heptyl acrylate structure |
| (A-6) | octyl/nonyl acrylate structure |

TABLE 2-continued

| Resin | Repeating unit α |
|---|---|
| (A-7), (A-8), (A-21) | long-chain alkyl acrylate structure |

TABLE 3

| Resin | Repeating unit α |
|---|---|
| (A-9) | acrylate with –O–CH$_2$CH$_2$–O–C(=O)–CH$_2$CH$_2$–CO$_2$H side chain |
| (A-11), (A-15) | bornyl acrylate structure |
| (A-13) | norbornane lactone acrylate structure |

TABLE 3-continued

| Resin | Repeating unit α |
|---|---|
| (AX-1) | (vinyl-phenyl structure) |
| (AX-3) | (acrylate benzyl ester structure) |

TABLE 4

| Resin | Repeating unit α |
|---|---|
| (A-22) | (acrylate long-chain alkyl ester structure) |
| (A-23) | (acrylate 2-ethylhexyl ester structure) |
| (A-24) | (acrylate isobutyl ester structure) |
| (A-25) | (acrylate benzyl ester structure) |

<Acid Generator>

The structures of the acid generators (compounds (C-1) to (C-13)) used are shown below.

(C-1) — sulfonium salt with $C_4F_9SO_3^-$ (C-2) — triphenylsulfonium $C_4F_9SO_3^-$ (C-3) — sulfonium salt with adamantyl difluoroacetate sulfonate ($^-O_3S$–CF$_2$–C(O)O–adamantyl-CH$_2$)

(C-4) — sulfonium salt with perfluoropropanesulfonyl decahydroisoquinoline amide ($^-O_3S$–CF$_2$CF$_2$CF$_2$–S(O)$_2$–N(decahydroisoquinoline))

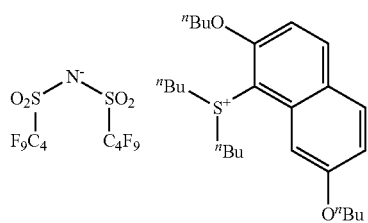 (C-5)
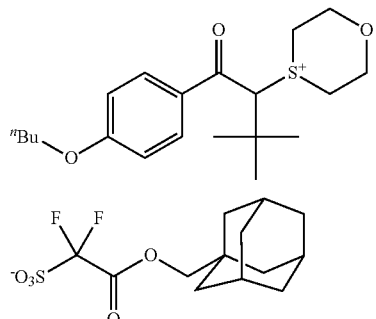 (C-6)
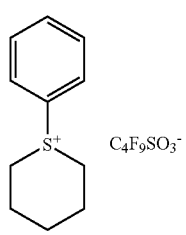 (C-7)
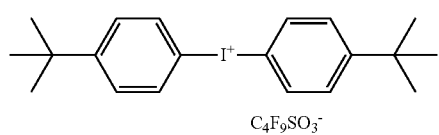 (C-8)
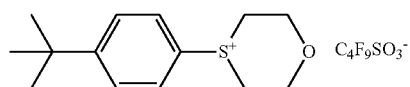 (C-9)
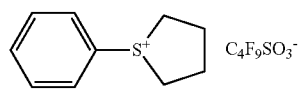 (C-10)
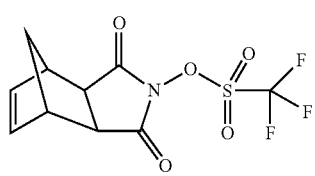 (C-11)
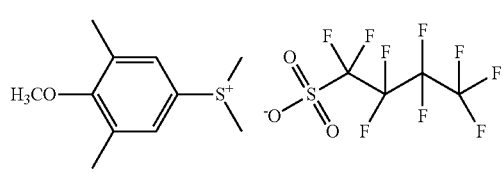 (C-12)
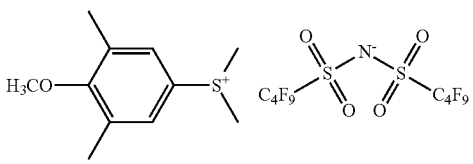 (C-13)
<Acid Diffusion Control Agent>
The acid diffusion control agents used are shown below.
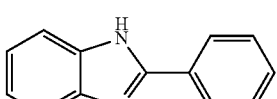 (D-1)
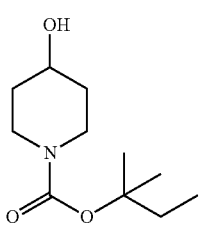 (D-2)
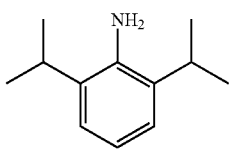 (D-3)
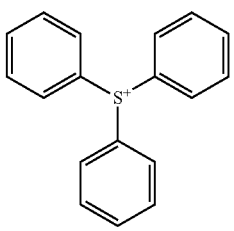 (D-4)
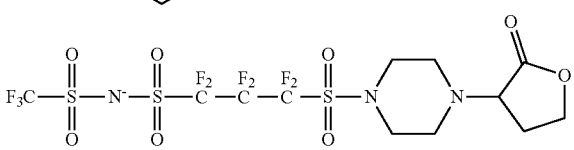
Triethylamine (D-5)
Triethanolamine (D-6)
Triisopropanolamine (D-7)
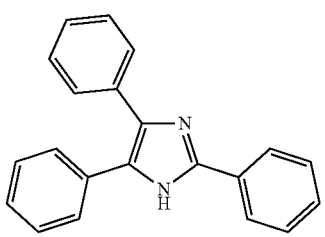 (D-8)

(D-9), (D-10), (D-11) [chemical structures]

<Surfactant>
The surfactant used is shown below.

(E-1) [chemical structure]

(E-2): MEGAFACE R-41 (manufactured by DIC Corporation)

(E-3): KF-53 (manufactured by Shin-Etsu Chemical Co., Ltd.)

<Other Additives>
Other additives used are shown below.

F-1, F-2, F-3, F-4, F-5, F-6, F-7, F-8, F-9, F-10 [chemical structures]

As F-10, LUTONAL M40 manufactured by BASF was used.

<Solvent>
The solvents used are shown below.
S-1: Propylene glycol monomethyl ether acetate (PGMEA)
S-2: Propylene glycol monomethyl ether (PGME)
S-3: Ethyl lactate (EL)
S-4: Ethyl 3-ethoxypropionate (EEP)
S-5: 2-Heptanone (MAK)
S-6: Methyl 3-methoxypropionate (MMP)
S-7: 3-Methoxybutyl acetate
S-8: Butyl acetate <Preparation of Actinic Ray-Sensitive or Radiation-Sensitive Resin Composition>

The respective components shown in Tables 5 to 8 below were mixed such that they reached the concentrations (% by mass) of the solid content described in Tables 5 to 8 below, thereby obtaining a solution. Then, the obtained solution was filtered through a polyethylene filter having a pore size of 3 μm to prepare actinic ray-sensitive or radiation-sensitive resin compositions (resist compositions) res-1 to res-89, and res-1X to res-4X. In addition, in the resist composition, the solid content means all components excluding a solvent. The obtained resist composition was used in Examples and Comparative Examples.

Moreover, in Tables 5 to 8 below, the contents (% by mass) of the respective components excluding a solvent mean contents with respect to the total solid content. In addition, a content ratio (% by mass) with respect to the total solvent of the solvents used are described in Tables 5 to 8 below.

TABLE 5

|  | Resist composition | Resin Type | Resin Content (% by mass) | Acid generator Type | Acid generator Content (% by mass) | Acid diffusion control agent Type | Acid diffusion control agent Content (% by mass) | Surfactant Type | Surfactant Content (% by mass) |
|---|---|---|---|---|---|---|---|---|---|
| Example 1 | res-1 | A-1 | 96.85 | C-1 | 2.9 | D-2 | 0.2 | E-1 | 0.05 |
| Example 2 | res-2 | A-2 | 97.35 | C-4 | 2.5 | D-4 | 0.1 | E-1 | 0.05 |
| Example 3 | res-3 | A-3 | 96.75 | C-3 | 3.1 | D-2 | 0.1 | E-1 | 0.05 |
| Example 4 | res-4 | A-4 | 97.40 | C-2 | 2.5 | D-2 | 0.1 | — | — |
| Example 5 | res-5 | A-5 | 97.15 | C-1 | 2.7 | D-3 | 0.1 | E-1 | 0.05 |
| Example 6 | res-6 | A-6 | 96.65 | C-3 | 3.1 | D-1 | 0.2 | E-1 | 0.05 |
| Example 7 | res-7 | A-7 | 97.00 | C-1 | 2.9 | D-4 | 0.1 | — | — |
| Example 8 | res-8 | A-8 | 96.75 | C-3 | 3.1 | D-2 | 0.1 | E-1 | 0.05 |
| Example 9 | res-9 | A-9 | 96.85 | C-1 | 2.9 | D-2 | 0.2 | E-1 | 0.05 |
| Example 10 | res-10 | A-10 | 97.15 | C-1 | 2.7 | D-3 | 0.1 | E-1 | 0.05 |
| Example 11 | res-11 | A-11 | 96.85 | C-1 | 2.9 | D-2 | 0.2 | E-1 | 0.05 |
| Example 12 | res-12 | A-12 | 97.15 | C-1 | 2.7 | D-3 | 0.1 | E-1 | 0.05 |
| Example 13 | res-13 | A-13 | 97.55 | C-5 | 2.3 | D-4 | 0.1 | E-1 | 0.05 |
| Example 14 | res-14 | A-14 | 97.15 | C-1 | 2.7 | D-3 | 0.1 | E-1 | 0.05 |
| Example 15 | res-15 | A-15 | 96.85 | C-1 | 2.9 | D-2 | 0.2 | E-1 | 0.05 |
| Example 16 | res-16 | A-16 | 97.35 | C-4 | 2.5 | D-4 | 0.1 | E-1 | 0.05 |
| Example 17 | res-17 | A-17 | 96.96 | C-4 | 2.8 | D-4 | 0.2 | E-1 | 0.04 |
| Example 18 | res-18 | A-18 | 96.59 | C-3 | 3.1 | D-2 | 0.3 | E-1 | 0.01 |
| Example 19 | res-19 | A-19 | 97.40 | C-2 | 2.5 | D-2 | 0.1 | — | — |
| Example 20 | res-20 | A-20 | 97.05 | C-1 | 2.8 | D-2 | 0.1 | E-1 | 0.05 |
| Example 21 | res-21 | A-21 | 95.55 | C-3 | 4.1 | D-2 | 0.3 | E-1 | 0.05 |
| Example 22 | res-22 | A-22 | 97.35 | C-4 | 2.5 | D-4 | 0.1 | E-1 | 0.05 |
| Example 23 | res-23 | A-23 | 96.75 | C-3 | 3.1 | D-2 | 0.1 | E-1 | 0.05 |

|  | Other additives Type | Other additives Content (% by mass) | Solvent Solvent 1 | Solvent Content ratio (% by mass) of solvent 1 | Solvent Solvent 2 | Solvent Content ratio (% by mass) of solvent 2 | Concentration (% by mass) of solid content |
|---|---|---|---|---|---|---|---|
| Example 1 | — | — | S-1 | 60 | S-2 | 40 | 39 |
| Example 2 | — | — | S-1 | 100 | — | — | 33 |
| Example 3 | — | — | S-1 | 80 | S-2 | 20 | 31 |
| Example 4 | — | — | S-1 | 50 | S-5 | 50 | 28 |
| Example 5 | — | — | S-1 | 70 | S-2 | 30 | 33 |
| Example 6 | — | — | S-1 | 80 | S-3 | 20 | 31 |
| Example 7 | — | — | S-5 | 60 | S-6 | 40 | 28 |
| Example 8 | — | — | S-1 | 80 | S-2 | 20 | 31 |
| Example 9 | — | — | S-1 | 60 | S-2 | 40 | 39 |
| Example 10 | — | — | S-1 | 70 | S-2 | 30 | 33 |
| Example 11 | — | — | S-1 | 60 | S-2 | 40 | 39 |
| Example 12 | — | — | S-1 | 80 | S-2 | 20 | 36 |
| Example 13 | — | — | S-4 | 50 | S-7 | 50 | 39 |
| Example 14 | — | — | S-1 | 80 | S-2 | 20 | 36 |
| Example 15 | — | — | S-1 | 60 | S-2 | 40 | 39 |
| Example 16 | — | — | S-1 | 100 | — | — | 33 |
| Example 17 | — | — | S-1 | 100 | — | — | 33 |
| Example 18 | — | — | S-1 | 30 | S-2 | 70 | 32 |
| Example 19 | — | — | S-1 | 50 | S-5 | 50 | 33 |
| Example 20 | — | — | S-1 | 60 | S-2 | 40 | 36 |
| Example 21 | — | — | S-1 | 80 | S-2 | 20 | 32 |
| Example 22 | — | — | S-1 | 100 | — | — | 31 |
| Example 23 | — | — | S-1 | 40 | S-2 | 60 | 32 |

TABLE 6

| | Resist composition | Resin Type | Resin Content (% by mass) | Acid generator Type | Acid generator Content (% by mass) | Acid diffusion control agent Type | Acid diffusion control agent Content (% by mass) | Surfactant Type | Surfactant Content (% by mass) |
|---|---|---|---|---|---|---|---|---|---|
| Example 24 | res-24 | A-1 | 88.57 | C-4 | 1.3 | D-2 | 0.04 | E-1 | 0.09 |
| Example 25 | res-25 | A-1 | 83.72 | C-4 | 1.1 | D-2 | 0.1 | E-1 | 0.08 |
| Example 26 | res-26 | A-1 | 88.61 | C-3 | 1.3 | D-2 | 0.03 | E-1 | 0.06 |
| Example 27 | res-27 | A-1 | 83.79 | C-3 | 1.1 | D-2 | 0.02 | E-1 | 0.09 |
| Example 28 | res-28 | A-1 | 88.49 | C-1 | 1.4 | D-2 | 0.04 | E-1 | 0.07 |
| Example 29 | res-29 | A-1 | 83.67 | C-1 | 1.2 | D-2 | 0.08 | E-1 | 0.05 |
| Example 30 | res-30 | A-1 | 88.62 | C-1 | 1.3 | D-2 | 0.02 | E-1 | 0.06 |
| Example 31 | res-31 | A-1 | 83.69 | C-4 | 1.2 | D-2 | 0.03 | E-2 | 0.08 |
| Example 32 | res-32 | A-1 | 88.57 | C-3 | 1.3 | D-2 | 0.04 | E-2 | 0.09 |
| Example 33 | res-33 | A-1 | 83.79 | C-3 | 1.1 | D-2 | 0.1 | E-2 | 0.01 |
| Example 34 | res-34 | A-1 | 88.66 | C-1 | 1.3 | D-2 | 0.02 | E-2 | 0.02 |
| Example 35 | res-35 | A-1 | 83.74 | C-1 | 1.1 | D-2 | 0.11 | E-2 | 0.05 |
| Example 36 | res-36 | A-21 | 93.64 | C-4 | 1.3 | D-2 | 0.03 | E-1 | 0.03 |
| Example 37 | res-37 | A-21 | 93.62 | C-4 | 1.3 | D-2 | 0.07 | E-1 | 0.01 |
| Example 38 | res-38 | A-21 | 93.46 | C-3 | 1.4 | D-2 | 0.06 | E-1 | 0.08 |
| Example 39 | res-39 | A-21 | 93.50 | C-3 | 1.4 | D-2 | 0.05 | E-1 | 0.05 |
| Example 40 | res-40 | A-24 | 86.88 | C-1 | 2.9 | D-2 | 0.18 | E-1 | 0.04 |
| Example 41 | res-41 | A-6 | 86.71 | C-3 | 3.1 | D-1 | 0.16 | E-1 | 0.03 |
| Example 42 | res-42 | A-8 | 81.78 | C-3 | 3.1 | D-2 | 0.1 | E-1 | 0.02 |
| Example 43 | res-43 | A-25 | 87.14 | C-1 | 2.7 | D-3 | 0.1 | E-1 | 0.06 |
| Example 44 | res-44 | A-1 | 88.50 | C-6 | 1.4 | D-2 | 0.02 | E-2 | 0.08 |
| Example 45 | res-45 | A-13 | 97.55 | C-7 | 2.3 | D4 | 0.1 | E-1 | 0.05 |

| | Other additives Type | Other additives Content (% by mass) | Solvent 1 | Solvent Content ratio (% by mass) of solvent 1 | Solvent 2 | Solvent Content ratio (% by mass) of solvent 2 | Concentration (% by mass) of solid content |
|---|---|---|---|---|---|---|---|
| Example 24 | F-2 | 10 | S-1 | 50 | S-2 | 50 | 42 |
| Example 25 | F-4 | 15 | S-1 | 50 | S-2 | 50 | 43 |
| Example 26 | F-2 | 10 | S-1 | 50 | S-2 | 50 | 43 |
| Example 27 | F-4 | 15 | S-1 | 50 | S-2 | 50 | 41 |
| Example 28 | F-2 | 10 | S-1 | 50 | S-2 | 50 | 42 |
| Example 29 | F-4 | 15 | S-1 | 50 | S-2 | 50 | 44 |
| Example 30 | F-2 | 10 | S-1 | 50 | S-2 | 50 | 42 |
| Example 31 | F-4 | 15 | S-1 | 50 | S-2 | 50 | 43 |
| Example 32 | F-2 | 10 | S-1 | 50 | S-2 | 50 | 41 |
| Example 33 | F-4 | 15 | S-1 | 50 | S-2 | 50 | 45 |
| Example 34 | F-2 | 10 | S-1 | 50 | S-2 | 50 | 40 |
| Example 35 | F-4 | 15 | S-1 | 50 | S-2 | 50 | 43 |
| Example 36 | F-2 | 5 | S-1 | 50 | S-2 | 50 | 42 |
| Example 37 | F-4 | 5 | S-1 | 50 | S-2 | 50 | 41 |
| Example 38 | F-2 | 5 | S-1 | 50 | S-2 | 50 | 42 |
| Example 39 | F-4 | 5 | S-1 | 50 | S-2 | 50 | 43 |
| Example 40 | F-1 | 10 | S-1 | 60 | S-2 | 40 | 39 |
| Example 41 | F-3 | 10 | S-1 | 80 | S-3 | 20 | 31 |
| Example 42 | F-5 | 15 | S-1 | 80 | S-2 | 20 | 31 |
| Example 43 | F-1 | 10 | S-1 | 40 | S-2 | 60 | 36 |
| Example 44 | F-2 | 10 | S-1 | 50 | S-2 | 50 | 42 |
| Example 45 | — | — | S-4 | 50 | S-7 | 50 | 39 |

TABLE 7

| | Resist composition | Resin Type | Resin Content (% by mass) | Acid generator Type | Acid generator Content (% by mass) | Acid diffusion control agent Type | Acid diffusion control agent Content (% by mass) | Surfactant Type | Surfactant Content (% by mass) |
|---|---|---|---|---|---|---|---|---|---|
| Example 46 | res-46 | A-1 | 83.69 | C-6 | 1.2 | D-2 | 0.03 | E-2 | 0.08 |
| Example 47 | res-47 | A-1 | 90.57 | C-6 | 1.3 | D-2 | 0.04 | E-1 | 0.09 |
| Example 48 | res-48 | A-1 | 83.72 | C-6 | 1.1 | D-2 | 0.1 | E-1 | 0.08 |
| Example 49 | res-49 | A-1 | 92.50 | C-6 | 1.4 | D-1 | 0.02 | E-2 | 0.08 |
| Example 50 | res-50 | A-1 | 83.69 | C-6 | 1.2 | D-8 | 0.03 | E-2 | 0.08 |
| Example 51 | res-51 | A-1 | 85.57 | C-6 | 1.3 | D-9 | 0.04 | E-1 | 0.09 |
| Example 52 | res-52 | A-1 | 83.72 | C-6 | 1.1 | D-10 | 0.1 | E-1 | 0.08 |
| Example 53 | res-53 | A-1 | 97.84 | C-8 | 2 | D-5 | 0.07 | — | — |
| Example 54 | res-54 | A-1 | 97.84 | C-2 | 2 | D-5 | 0.07 | — | — |
| Example 55 | res-55 | A-1 | 97.84 | C-7 | 2 | D-5 | 0.07 | — | — |

TABLE 7-continued

| | | | | | | | | | |
|---|---|---|---|---|---|---|---|---|---|
| Example 56 | res-56 | A-1 | 97.84 | C-8 | 2 | D-6 | 0.07 | — | — |
| Example 57 | res-57 | A-1 | 97.84 | C-8 | 2 | D-7 | 0.07 | — | — |
| Example 58 | res-58 | A-1 | 93.16 | C-8 | 2 | D-5 | 0.06 | — | — |
| Example 59 | res-59 | A-1 | 93.16 | C-8 | 2 | D-5 | 0.06 | — | — |
| Example 60 | res-60 | A-1 | 98.93 | C-8 | 1 | D-5 | 0.03 | — | — |
| Example 61 | res-61 | A-21 | 97.84 | C-8 | 2 | D-5 | 0.07 | — | — |
| Example 62 | res-62 | A-21 | 97.84 | C-2 | 2 | D-5 | 0.07 | — | — |
| Example 63 | res-63 | A-21 | 97.84 | C-7 | 2 | D-5 | 0.07 | — | — |
| Example 64 | res-64 | A-21 | 97.84 | C-8 | 2 | D-6 | 0.07 | — | — |
| Example 65 | res-65 | A-21 | 97.84 | C-8 | 2 | D-7 | 0.07 | — | — |
| Example 66 | res-66 | A-21 | 93.16 | C-8 | 2 | D-5 | 0.06 | — | — |
| Example 67 | res-67 | A-21 | 93.16 | C-8 | 2 | D-5 | 0.06 | — | — |
| Example 68 | res-68 | A-21 | 98.93 | C-8 | 1 | D-5 | 0.03 | — | — |

| | Other additives | | Solvent | | | | |
|---|---|---|---|---|---|---|---|
| | Type | Content (% by mass) | Solvent 1 | Content ratio (% by mass) of solvent 1 | Solvent 2 | Content ratio (% by mass) of solvent 2 | Concentration (% by mass) of solid content |
| Example 46 | F-4 | 15 | S-1 | 50 | S-2 | 50 | 43 |
| Example 47 | F-2 | 8 | S-1 | 50 | S-2 | 50 | 42 |
| Example 48 | F-4 | 15 | S-1 | 50 | S-2 | 50 | 43 |
| Example 49 | F-2 | 6 | S-1 | 50 | S-2 | 50 | 42 |
| Example 50 | F-4 | 15 | S-1 | 50 | S-2 | 50 | 43 |
| Example 51 | F-2 | 13 | S-1 | 50 | S-2 | 50 | 42 |
| Example 52 | F-4 | 15 | S-1 | 50 | S-2 | 50 | 43 |
| Example 53 | F-6 | 0.088 | S-1 | 20 | S-2 | 80 | 40 |
| Example 54 | F-6 | 0.088 | S-1 | 20 | S-2 | 80 | 40 |
| Example 55 | F-6 | 0.088 | S-1 | 20 | S-2 | 80 | 40 |
| Example 56 | F-6 | 0.088 | S-1 | 20 | S-2 | 80 | 40 |
| Example 57 | F-6 | 0.088 | S-1 | 20 | S-2 | 80 | 40 |
| Example 58 | F-6/F-7 | 0.08/4.7 | S-1 | 20 | S-2 | 80 | 40 |
| Example 59 | F-6/F-8 | 0.08/4.7 | S-1 | 20 | S-2 | 80 | 40 |
| Example 60 | F-6 | 0.045 | S-1 | 20 | S-2 | 80 | 40 |
| Example 61 | F-6 | 0.088 | S-1 | 20 | S-2 | 80 | 40 |
| Example 62 | F-6 | 0.088 | S-1 | 20 | S-2 | 80 | 40 |
| Example 63 | F-6 | 0.088 | S-1 | 20 | S-2 | 80 | 40 |
| Example 64 | F-6 | 0.088 | S-1 | 20 | S-2 | 80 | 40 |
| Example 65 | F-6 | 0.088 | S-1 | 20 | S-2 | 80 | 40 |
| Example 66 | F-6/F-7 | 0.08/4.7 | S-1 | 20 | S-2 | 80 | 40 |
| Example 67 | F-6/F-8 | 0.08/4.7 | S-1 | 20 | S-2 | 80 | 40 |
| Example 68 | F-6 | 0.045 | S-1 | 20 | S-2 | 80 | 40 |

TABLE 8

| | Resist composition | Resin | | Acid generator | | Acid diffusion control agent | | Surfactant | |
|---|---|---|---|---|---|---|---|---|---|
| | | Type | Content (% by mass) | Type | Content (% by mass) | Type | Content (% by mass) | Type | Content (% by mass) |
| Example 69 | res-69 | A-1 | 78.60 | C-9 | 1.3 | D-2 | 0.02 | E-2 | 0.08 |
| Example 70 | res-70 | A-1 | 87.10 | C-10 | 1.8 | D-2 | 0.02 | E-2 | 0.08 |
| Example 71 | res-71 | A-1 | 95.50 | C-8 | 1.4 | D-2 | 0.02 | E-2 | 0.08 |
| Example 72 | res-72 | A-1 | 92.70 | C-2 | 2.2 | D-2 | 0.02 | E-2 | 0.08 |
| Example 73 | res-73 | A-1 | 96.80 | C-7 | 1.1 | D-2 | 0.02 | E-2 | 0.08 |
| Example 74 | res-74 | A-1 | 91.10 | C-4 | 1.8 | D-5 | 0.02 | E-2 | 0.08 |
| Example 75 | res-75 | A-1 | 86.80 | C-4 | 2.1 | D-6 | 0.02 | E-2 | 0.08 |
| Example 76 | res-76 | A-1 | 92.40 | C-4 | 1.5 | D-7 | 0.02 | E-2 | 0.08 |
| Example 77 | res-77 | A-1 | 93.30 | C-4 | 1.6 | D-2 | 0.02 | E-2 | 0.08 |
| Example 78 | res-78 | A-1 | 93.40 | C-4 | 1.5 | D-2 | 0.02 | E-2 | 0.08 |
| Example 79 | res-79 | A-1 | 89.00 | C-4 | 0.9 | D-2 | 0.02 | E-2 | 0.08 |
| Example 80 | res-80 | A-1 | 97.93 | C-11 | 2 | D-1 | 0.07 | — | — |
| Example 81 | res-81 | A-1 | 97.93 | C-11 | 2 | D-1 | 0.07 | — | — |
| Example 82 | res-82 | A-1 | 95.48 | C-12/C-13 | 1.2/1.2 | D-11 | 0.02 | E-3 | 0.1 |
| Example 83 | res-83 | A-1 | 95.48 | C-12/C-13 | 1.2/1.2 | D-11 | 0.02 | E-3 | 0.1 |
| Example 84 | res-84 | A-1 | 90.40 | C-11 | 1.5 | D-2 | 0.02 | E-2 | 0.08 |
| Example 85 | res-85 | A-1 | 89.50 | C-12/C-13 | 1.2/1.2 | D-2 | 0.02 | E-2 | 0.08 |
| Example 86 | res-86 | A-1 | 87.40 | C-4 | 1.5 | D-11 | 0.02 | E-2 | 0.08 |
| Example 87 | res-87 | A-1 | 90.50 | C-6 | 1.4 | D-2 | 0.02 | E-3 | 0.08 |

TABLE 8-continued

| | | | | | | | | | |
|---|---|---|---|---|---|---|---|---|---|
| Example 88 | res-88 | A-1 | 88.50 | C-6 | 1.4 | D-2 | 0.02 | E-2 | 0.08 |
| Example 89 | res-89 | A-1 | 93.50 | C-6 | 1.4 | D-2 | 0.02 | E-2 | 0.08 |
| Comparative Example 1 | rea-1X | AX-1 | 97.35 | C-4 | 2.5 | D-4 | 0.1 | E-1 | 0.05 |
| Comparative Example 2 | res-2X | AX-2 | 97.15 | C-1 | 2.7 | D-3 | 0.1 | E-1 | 0.05 |
| Comparative Example 3 | res-3X | AX-3 | 96.85 | C-1 | 2.9 | D-2 | 0.2 | E-1 | 0.05 |
| Comparative Example 4 | res-4X | AX-4 | 96.85 | C-1 | 2.9 | D-2 | 0.2 | E-1 | 0.05 |

| | Other additives | | Solvent | | | | Concentration |
|---|---|---|---|---|---|---|---|
| | Type | Content (% by mass) | Solvent 1 | Content ratio (% by mass) of solvent 1 | Solvent 2 | Content ratio (% by mass) of solvent 2 | (% by mass) of solid content |
| Example 69 | F-2 | 20 | S-1 | 50 | S-2 | 50 | 42 |
| Example 70 | F-2 | 11 | S-1 | 50 | S-2 | 50 | 42 |
| Example 71 | F-2 | 3 | S-1 | 50 | S-2 | 50 | 42 |
| Example 72 | F-2 | 5 | S-1 | 50 | S-2 | 50 | 42 |
| Example 73 | F-2 | 2 | S-1 | 50 | S-2 | 50 | 42 |
| Example 74 | F-2 | 7 | S-1 | 50 | S-2 | 50 | 42 |
| Example 75 | F-2 | 11 | S-1 | 50 | S-2 | 50 | 42 |
| Example 76 | F-2 | 6 | S-1 | 50 | S-2 | 50 | 42 |
| Example 77 | F-2 | 5 | S-1 | 50 | S-2 | 50 | 42 |
| Example 78 | F-2 | 5 | S-1 | 50 | S-2 | 50 | 42 |
| Example 79 | F-2 | 10 | S-1 | 50 | S-2 | 50 | 42 |
| Example 80 | — | — | S-1 | 50 | S-5 | 80 | 40 |
| Example 81 | — | — | S-1 | 50 | S-8 | 80 | 40 |
| Example 82 | F-9 | 2 | S-2 | 70 | S-3 | 30 | 40 |
| Example 83 | F-10 | 2 | S-2 | 70 | S-3 | 30 | 40 |
| Example 84 | F-2 | 8 | S-1 | 50 | S-2 | 50 | 42 |
| Example 85 | F-2 | 8 | S-1 | 50 | S-2 | 50 | 42 |
| Example 86 | F-2 | 11 | S-1 | 50 | S-2 | 50 | 42 |
| Example 87 | F-2 | 8 | S-1 | 50 | S-2 | 50 | 42 |
| Example 88 | F-9 | 10 | S-1 | 50 | S-2 | 50 | 42 |
| Example 89 | F-10 | 5 | S-1 | 50 | S-2 | 50 | 42 |
| Comparative Example 1 | — | — | S-1 | 100 | — | — | 33 |
| Comparative Example 2 | — | — | S-1 | 80 | S-2 | 20 | 36 |
| Comparative Example 3 | — | — | S-1 | 60 | S-2 | 40 | 39 |
| Comparative Example 4 | — | — | S-1 | 60 | S-2 | 40 | 39 |

<Pattern Formation and Various Evaluations>

Pattern Formation (Examples 1 to 89 and Comparative Examples 1 to 4)

The resist composition prepared above was added dropwise to an 8-inch Si substrate (manufactured by Advanced Materials Technology (hereinafter also referred to as a "substrate")) in the state where the substrate was stationary, which had been subjected to a hexamethyldisilazane treatment, using a spin coater "ACT-8" manufactured by Tokyo Electron Limited, while not being provided with an antireflection layer. After the dropwise addition, the substrate was rotated while maintaining the rotation speed at 500 rpm for 3 seconds, at 100 rpm for 2 seconds, at 500 rpm for 3 seconds, and at 100 rpm for 2 seconds again, and thereafter, the rotation speed was raised to a film thickness-setting rotation speed (1,200 rpm), which was maintained for 60 seconds. Thereafter, drying under heating was performed on a hot plate at 150° C. for 60 seconds to form a positive-tone resist film having a film thickness of 9.2 μm. This resist film was subjected to pattern exposure through a mask having a space width of 1 μm and a line width of 5 μm, using a KrF excimer laser scanner (manufactured by ASML, PAS5500/850C, wavelength of 248 nm). After the irradiation, the resist film was baked at 110° C. for 60 seconds, immersed in an aqueous 2.38%-by-mass tetramethylammonium hydroxide (TMAH) solution for 60 seconds, then rinsed with pure water for 30 seconds, and dried to form a line-and-space pattern.

According to the procedure, a pattern wafer for evaluation, having a substrate and a pattern formed on a surface of the substrate, was obtained.

1 inch corresponds to 25.4 milliliters.

<Performance Evaluation>

Performance evaluation of the pattern was carried out using the obtained pattern wafer for evaluation.

(Performance Evaluation 1: Evaluation of Cross-Sectional Rectangularity of Pattern)

The cross-sectional shape of the pattern was observed with a scanning electron microscope (SEM) (9380II manufactured by Hitachi High-Technologies Corporation), and thus, a case where a side face is substantially vertically steep is defined as A, a case where a side surface is slightly tapered is defined as B, a case where a side surface is wavy is defined as C, and in particular, a case where a side surface is wavy is defined as D. The results are shown in the section of "Rectangularity" in Tables 9 to 11 below.

(Performance Evaluation 2: Evaluation of Resolution)

While changing the exposure dose using the above-mentioned mask, the space width of the obtained resist pattern was observed. By taking the finest space width of the space widths of the obtained resist pattern as an index for resolution evaluation, the space widths are described in the section of "resolution (μm)" in Tables 9 to 11 below.

(Performance Evaluation 3: Evaluation of Film Peeling after Vacuum Treatment)

A pattern wafer for evaluation was placed in a pressure-resistant vessel and subjected to a vacuum treatment (left to stand at 0.01 Torr for 15 minutes). The wafer after the vacuum treatment was observed with an optical microscope (scanning confocal laser microscope manufactured by Olympus Co., Ltd., model number: LEXT OLS3100 used in an optical microscope mode), and the film peeling on the surface of the wafer was observed. A case where film peeling was observed in many positions with the number of positions being more than 100, was counted as D, a case where film peeling was observed in 6 to 100 positions was counted as C, a case where film peeling was observed in 2 to 5 positions was counted as B, a case where film peeling was observed in one position was counted as A, and a case where film peeling was observed in zero place was counted as S. The results are shown in the section of "Film peeling after vacuum treatment" in Tables 9 to 11 below.

1 Torr corresponds to about 133.322 Pa.

TABLE 9

| | Rectangularity | Resolution (μm) | Film peeling after vacuum treatment |
|---|---|---|---|
| Example 1 | A | 1.6 | B |
| Example 2 | B | 1.4 | A |
| Example 3 | A | 1.2 | B |
| Example 4 | B | 1.9 | A |
| Example 5 | B | 1.2 | A |
| Example 6 | A | 1.5 | A |
| Example 7 | A | 1.1 | S |
| Example 8 | A | 1.2 | S |
| Example 9 | C | 1.4 | A |
| Example 10 | B | 1.5 | B |
| Example 11 | B | 1.3 | C |
| Example 12 | A | 1.7 | C |
| Example 13 | C | 1.3 | C |
| Example 14 | A | 1.7 | B |
| Example 15 | B | 1.6 | B |
| Example 16 | A | 1.3 | B |
| Example 17 | B | 1.1 | S |
| Example 18 | A | 1.2 | S |
| Example 19 | A | 1.3 | B |
| Example 20 | B | 1.1 | A |
| Example 21 | A | 1.3 | S |
| Example 22 | A | 1.1 | A |
| Example 23 | B | 1.2 | S |
| Example 24 | A | 1.1 | S |
| Example 25 | A | 1.1 | S |
| Example 26 | A | 1.1 | S |
| Example 27 | A | 1.1 | S |
| Example 28 | A | 1.1 | S |
| Example 29 | A | 1.1 | S |
| Example 30 | A | 1.1 | S |
| Example 31 | A | 1.1 | S |
| Example 32 | A | 1.1 | S |
| Example 33 | A | 1.1 | S |
| Example 34 | A | 1.1 | S |
| Example 35 | A | 1.1 | S |

TABLE 10

| | Rectangularity | Resolution (μm) | Film peeling after vacuum treatment |
|---|---|---|---|
| Example 36 | A | 1.1 | S |
| Example 37 | A | 1.1 | S |
| Example 38 | A | 1.1 | S |
| Example 39 | A | 1.1 | S |
| Example 40 | C | 1.1 | B |
| Example 41 | A | 1.1 | A |
| Example 42 | A | 1.1 | S |
| Example 43 | C | 1.1 | C |
| Example 44 | A | 1.1 | S |
| Example 45 | C | 1.4 | C |
| Example 46 | A | 1.1 | S |
| Example 47 | A | 1.1 | S |
| Example 48 | A | 1.1 | S |
| Example 49 | A | 1.1 | S |
| Example 50 | A | 1.1 | S |
| Example 51 | A | 1.1 | S |
| Example 52 | A | 1.1 | S |
| Example 53 | B | 1.8 | S |
| Example 54 | B | 1.8 | S |
| Example 55 | B | 1.8 | S |
| Example 56 | B | 1.8 | S |
| Example 57 | B | 1.8 | S |
| Example 58 | B | 1.8 | S |
| Example 59 | B | 1.8 | S |
| Example 60 | B | 1.8 | S |
| Example 61 | B | 1.8 | S |
| Example 62 | B | 1.8 | S |
| Example 63 | B | 1.8 | S |
| Example 64 | B | 1.8 | S |
| Example 65 | B | 1.8 | S |
| Example 66 | B | 1.8 | S |
| Example 67 | B | 1.8 | S |
| Example 68 | B | 1.8 | S |
| Example 69 | B | 1.8 | S |
| Example 70 | B | 1.8 | S |

TABLE 11

| | Rectangularity | Resolution (μm) | Film peeling after vacuum treatment |
|---|---|---|---|
| Example 71 | B | 1.8 | S |
| Example 72 | B | 1.8 | S |
| Example 73 | B | 1.8 | S |
| Example 74 | A | 1.1 | S |
| Example 75 | A | 1.1 | S |
| Example 76 | A | 1.1 | S |
| Example 77 | A | 1.1 | S |
| Example 78 | A | 1.1 | S |
| Example 79 | A | 1.1 | S |
| Example 80 | B | 1.8 | S |
| Example 81 | B | 1.8 | S |
| Example 82 | B | 1.8 | S |
| Example 83 | B | 1.8 | S |
| Example 84 | B | 1.8 | S |
| Example 85 | B | 1.8 | S |
| Example 86 | A | 1.1 | S |
| Example 87 | A | 1.1 | S |
| Example 88 | A | 1.1 | S |
| Example 89 | A | 1.1 | S |
| Comparative Example 1 | B | 2.4 | C |
| Comparative Example 2 | D | 1.7 | B |
| Comparative Example 3 | A | 1.6 | D |
| Comparative Example 4 | A | 2.5 | B |

As seen from the results in Tables 9 to 11, it could be seen that in a case where the resist compositions of Examples are used for formation of a resist film having a film thickness of 2 μm or more, the cross-sectional rectangularity of a pattern is excellent, the film peeling after a vacuum treatment is suppressed, and thus, the resolution is excellent.

According to the present invention, it is possible to provide an actinic ray-sensitive or radiation-sensitive resin composition, which is used for formation of a film having a film thickness of 2 μm or more, and has excellent cross-sectional rectangularity of a pattern, suppressed film peeling after a vacuum treatment, and excellent resolution; a resist film formed with the actinic ray-sensitive or radiation-sensitive resin composition; and a pattern forming method and a method for manufacturing an electronic device, each using the actinic ray-sensitive or radiation-sensitive resin composition.

Although the present invention has been described in detail and with reference to specific embodiments, it is obvious to those skilled in the art that various changes or modifications can be made without departing from the spirit and scope of the present invention.

What is claimed is:

1. An actinic ray-sensitive or radiation-sensitive resin composition comprising a resin (A),
   wherein the resin (A) includes a repeating unit having an acidic group, a repeating unit having an acid-decomposable group, and a repeating unit B1 derived from a monomer allowing a homopolymer formed therefrom to have a glass transition temperature of 50° C. or lower,
   the content of the repeating unit having an acidic group is 15% by mole or more with respect to all the repeating units in the resin (A),
   the content of the repeating unit having an acid-decomposable group is more than 20% by mole with respect to all the repeating units in the resin (A),
   the glass transition temperature of the resin (A) is 145° C. or lower,
   the actinic ray-sensitive or radiation-sensitive resin composition further comprises a photoacid generator which is a compound represented by General Formula (ZI-4) or General Formula (ZII):

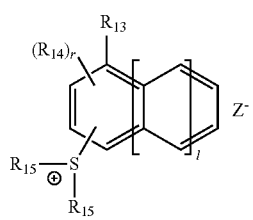

(ZI-4)

wherein in General Formula (ZI-4),
l represents an integer of 0 to 2,
r represents an integer of 0 to 8,
$R_{13}$ represents a hydrogen atom, a fluorine atom, a hydroxyl group, an alkyl group, a cycloalkyl group, an alkoxy group, an alkoxycarbonyl group, or a group having a monocyclic or polycyclic cycloalkyl skeleton, provided that the groups other than the hydroxyl group may have a substituent,
each $R_{14}$ independently represents an alkyl group, a cycloalkyl group, an alkoxy group, an alkylsulfonyl group, a cycloalkylsulfonyl group, an alkylcarbonyl group, an alkoxycarbonyl group, or an alkoxy group having a monocyclic or polycyclic cycloalkyl skeleton, provided that these groups may have a substituent, each $R_{15}$ independently represents an alkyl group, a cycloalkyl group, or a naphthyl group, provided that these groups may have a substituent, and further provided that two $R_{15}$'s may be bonded to each other to form a ring, and in a case where two $R_{15}$'s are bonded to form a ring, the ring skeleton may include a heteroatom, and $Z^-$ represents an anion,

(ZII)

wherein in General Formula (ZII), $R_{204}$ and $R_{205}$ each independently represents an aryl group, an alkyl group, or a cycloalkyl group, provided that the aryl group of each of $R_{204}$ and $R_{205}$ may be an aryl group having a heterocyclic structure, and further provided that the aryl group, the alkyl group, and the cycloalkyl group of each of $R_{204}$ and $R_{205}$ may each independently have a substituent, and $Z^-$ represents an anion, and the actinic ray-sensitive or radiation-sensitive resin composition is used for formation of a film having a film thickness of 2 μm or more.

2. The actinic ray-sensitive or radiation-sensitive resin composition according to claim 1,
   wherein the acidic group is a carboxyl group, a phenolic hydroxyl group, or a sulfo group.

3. The actinic ray-sensitive or radiation-sensitive resin composition according to claim 1,
   wherein at least one of the repeating units contained in the resin (A) has an aromatic ring.

4. The actinic ray-sensitive or radiation-sensitive resin composition according to claim 1,
   wherein the content of the repeating unit having an acidic group is 45% by mole or more with respect to all the repeating units in the resin (A).

5. The actinic ray-sensitive or radiation-sensitive resin composition according to claim 1,
   wherein the Hansen solubility parameter of the resin (A) is 20.5 $(J/cm^3)^{0.5}$ or less.

6. The actinic ray-sensitive or radiation-sensitive resin composition according to claim 1,
   wherein the resin (A) has a repeating unit C1 having a Hansen solubility parameter of 19.5 $(J/cm^3)^{0.5}$ or less.

7. The actinic ray-sensitive or radiation-sensitive resin composition according to claim 6,
   wherein the repeating unit C1 is a repeating unit derived from a monomer allowing a homopolymer formed therefrom to have a glass transition temperature of −20° C. or lower.

8. The actinic ray-sensitive or radiation-sensitive resin composition according to claim 6,
   wherein the repeating unit C1 is a repeating unit derived from a monomer having a Hansen solubility parameter of 16.0 $(J/cm^3)^{0.5}$ or less.

9. The actinic ray-sensitive or radiation-sensitive resin composition according to claim 6,
wherein the repeating unit C1 is a repeating unit represented by General Formula (1-2),

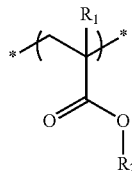

(1-2)

in General Formula (1-2), $R_1$ represents a hydrogen atom, a halogen atom, or an alkyl group, and $R_2$ represents a non-acid-decomposable chained alkyl group having 4 or more carbon atoms, which may include a heteroatom.

10. The actinic ray-sensitive or radiation-sensitive resin composition according to claim 6,
wherein the content of the repeating unit C1 is 5% by mole or more with respect to all the repeating units in the resin (A).

11. The actinic ray-sensitive or radiation-sensitive resin composition according to claim 1,
wherein the resin (A) has a repeating unit BC1 having a Hansen solubility parameter of 19.5 $(J/cm^3)^{0.5}$ or less and derived from a monomer allowing a homopolymer formed therefrom to have a glass transition temperature of 50° C. or lower.

12. The actinic ray-sensitive or radiation-sensitive resin composition according to claim 11,
wherein the repeating unit BC1 is a repeating unit derived from a monomer allowing a homopolymer formed therefrom to have a glass transition temperature of –20° C. or lower.

13. The actinic ray-sensitive or radiation-sensitive resin composition according to claim 11,
wherein the repeating unit BC1 is a repeating unit derived from a monomer having a Hansen solubility parameter of 16.0 $(J/cm^3)^{0.5}$ or less.

14. The actinic ray-sensitive or radiation-sensitive resin composition according to claim 11,
wherein the repeating unit BC1 is a repeating unit represented by General Formula (1-2),

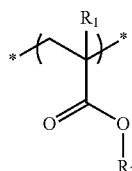

(1-2)

in General Formula (1-2), $R_1$ represents a hydrogen atom, a halogen atom, or an alkyl group, and $R_2$ represents a non-acid-decomposable chained alkyl group having 4 or more carbon atoms, which may include a heteroatom.

15. The actinic ray-sensitive or radiation-sensitive resin composition according to claim 11,
wherein the content of the repeating unit BC1 is 5% by mole or more with respect to all the repeating units in the resin (A).

16. The actinic ray-sensitive or radiation-sensitive resin composition according to claim 1,
wherein the repeating unit B1 is a repeating unit derived from a monomer allowing a homopolymer formed therefrom to have a glass transition temperature of –20° C. or lower.

17. The actinic ray-sensitive or radiation-sensitive resin composition according to claim 1,
wherein the repeating unit B1 is a repeating unit derived from a monomer having a Hansen solubility parameter of 16.0 $(J/cm^3)^{0.5}$ or less.

18. The actinic ray-sensitive or radiation-sensitive resin composition according to claim 1,
wherein the repeating unit B1 is a repeating unit represented by General Formula (1-2),

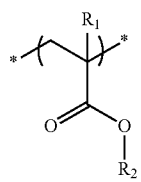

(1-2)

in General Formula (1-2), $R_1$ represents a hydrogen atom, a halogen atom, or an alkyl group, and $R_2$ represents a non-acid-decomposable chained alkyl group having 4 or more carbon atoms, which may include a heteroatom.

19. The actinic ray-sensitive or radiation-sensitive resin composition according to claim 1,
wherein the content of the repeating unit B1 is 5% by mole or more with respect to all the repeating units in the resin (A).

20. The actinic ray-sensitive or radiation-sensitive resin composition according to claim 1,
wherein the resin (A) contains a repeating unit represented by General Formula (1-2), a repeating unit represented by General Formula (1-3), and a repeating unit represented by General Formula (1-4),

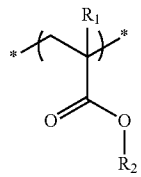

(1-2)

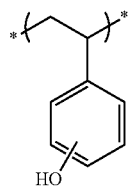

(1-3)

-continued (1-4)

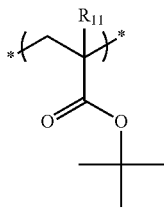

in General Formula (1-2), $R_1$ represents a hydrogen atom, a halogen atom, or an alkyl group, and $R_2$ represents a non-acid-decomposable chained alkyl group having 4 or more carbon atoms, which may include a heteroatom, and in General Formula (1-4), $R_{11}$ represents a hydrogen atom, a halogen atom, or an alkyl group.

21. The actinic ray-sensitive or radiation-sensitive resin composition according to claim 1, further comprising a compound that generates an acid upon irradiation with actinic rays or radiation, represented by General Formula (ZI-3),

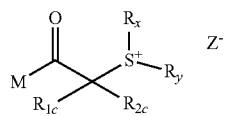

(ZI-3)

in General Formula (ZI-3), M represents an alkyl group, a cycloalkyl group, or an aryl group, in a case where M has a ring structure, the ring structure may include at least one of an oxygen atom, a sulfur atom, an ester bond, an amide bond, or a carbon-carbon double bond, $R_{1c}$ and $R_{2c}$ each independently represents a hydrogen atom, an alkyl group, a cycloalkyl group, a halogen atom, a cyano group, or an aryl group, $R_{1c}$ and $R_{2c}$ may be bonded to each other to form a ring, $R_x$ and $R_y$ each independently represents an alkyl group, a cycloalkyl group, or an alkenyl group, $R_x$ and $R_y$ may be bonded to each other to form a ring, at least two selected from M, $R_{1c}$, or $R_{2c}$ may be bonded to each other to form a ring structure, the ring structure may include a carbon-carbon double bond, and $Z^-$ represents an anion.

22. A pattern forming method comprising:
a resist film forming step of forming a resist film with the actinic ray-sensitive or radiation-sensitive resin composition according to claim 1;
an exposing step of exposing the resist film; and
a developing step of developing the exposed resist film with a developer.

23. A method for manufacturing an electronic device, the method comprising the pattern forming method according to claim 22.

24. A resist film having a film thickness of 2 μm or more, the resist film formed with the actinic ray-sensitive or radiation-sensitive resin composition according to claim 1.

* * * * *